US012390640B2

United States Patent
Covalin et al.

(10) Patent No.: US 12,390,640 B2
(45) Date of Patent: Aug. 19, 2025

(54) ELECTRICAL STIMULATION METHODS AND DEVICES FOR IMPROVING BLOOD MANAGEMENT

(71) Applicant: Spark Biomedical, Inc., Dallas, TX (US)

(72) Inventors: Alejandro Covalin, Los Angeles, CA (US); Christopher Czura, Oyster Bay, NY (US); Navid Khodaparast, Dallas, TX (US)

(73) Assignee: Spark Biomedical, Inc., Dallas, TX (US)

(*) Notice: Subject to any disclaimer, the term of this patent is extended or adjusted under 35 U.S.C. 154(b) by 0 days.

(21) Appl. No.: 18/926,706

(22) Filed: Oct. 25, 2024

(65) Prior Publication Data

US 2025/0041598 A1    Feb. 6, 2025

Related U.S. Application Data

(63) Continuation-in-part of application No. 18/583,160, filed on Feb. 21, 2024.

(60) Provisional application No. 63/535,996, filed on Aug. 31, 2023, provisional application No. 63/447,162, filed on Feb. 21, 2023.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01)

(58) Field of Classification Search
CPC .......................... A61N 1/36034; A61N 1/0456
See application file for complete search history.

(56) References Cited

U.S. PATENT DOCUMENTS

| | | | |
|---|---|---|---|
| 6,735,476 | B2 | 5/2004 | Mellen |
| 8,729,129 | B2 | 5/2014 | Tracey et al. |
| 10,912,712 | B2 | 2/2021 | Tracey et al. |
| 11,260,229 | B2 * | 3/2022 | Manogue ........... A61N 1/36053 |

(Continued)

FOREIGN PATENT DOCUMENTS

| | | |
|---|---|---|
| RU | 2239408 C2 * | 11/2004 |
| WO | WO2021011165 A1 | 1/2021 |

OTHER PUBLICATIONS

Spark Biomedical, Inc., "Transcutaneous Auricular Neurostimulation (tAN™) To Aid In The Reduction Of Symptoms Associated With Opioid Withdrawal", Sparrow Clinical Whitepaper, Version: MKT-005-V1, 2021, 8 pages.

(Continued)

*Primary Examiner* — Carl H Layno
*Assistant Examiner* — Maria Catherine Anthony
(74) *Attorney, Agent, or Firm* — Finch & Maloney PLLC

(57) ABSTRACT

In an illustrative embodiment, methods and system for increasing coagulation potential and/or triggering a higher platelet activation rate in a subject via auricular neurostimulation include contacting skin of the subject with one or more therapeutic electrodes, each electrode positioned in a respective region of nerve structures of the auriculotemporal nerve (ATN), nerve structures connected to the ATN, nerve structures of the auricular branch of the vagus nerve (ABVN), or nerve structures connected to the ABVN, applying, to the electrodes, one or more stimulation patterns.

23 Claims, 21 Drawing Sheets

(56) References Cited

U.S. PATENT DOCUMENTS

| | | |
|---|---|---|
| 2009/0287035 A1 | 11/2009 | Dietrich et al. |
| 2014/0135886 A1 | 5/2014 | Cook et al. |
| 2014/0206945 A1 | 7/2014 | Liao |
| 2015/0335876 A1 | 11/2015 | Jeffery et al. |
| 2019/0134390 A1 | 5/2019 | Shimada et al. |
| 2019/0321623 A1 | 10/2019 | Huston et al. |
| 2020/0238085 A1 | 7/2020 | Khodaparast et al. |
| 2021/0213286 A1 | 7/2021 | Covalin et al. |
| 2022/0192580 A1 | 6/2022 | Toth et al. |
| 2022/0212012 A1 | 7/2022 | Manogue |
| 2022/0305260 A1 | 9/2022 | Covalin et al. |

OTHER PUBLICATIONS

International Search Report and Written Opinion corresponding to PCT/US2024/016737 mailed Aug. 20, 2024.
International Search Report and Written Opinion corresponding to PCT/US2024/031287 mailed Oct. 28, 2024.

\* cited by examiner

ELECTRICAL STIMULATION METHODS AND DEVICES FOR IMPROVING BLOOD MANAGEMENT

RELATED APPLICATIONS

This application is a continuation-in-part of and claims priority to U.S. patent application Ser. No. 18/583, 160 entitled "Electrical Stimulation Methods and Devices for Improving Blood Management" and filed Feb. 21, 2024, which claims priority to: U.S. Provisional Patent Application No. 63/447,162 entitled "Electrical Stimulation Methods and Devices for Improving Blood Management" and filed Feb. 21, 2023; and U.S. Provisional Patent Application No. 63/535,996 entitled "Electrical Stimulation Methods and Devices for Improving Blood Management" and filed Aug. 31, 2023. This application is related to the following prior patent applications by Spark Biomedical, Inc. directed to stimulation therapies and stimulation devices: U.S. Pat. No. 10,967,182, entitled "Devices and Methods for Reducing Inflammation Using Electrical Stimulation" and issued Apr. 6, 2021, and U.S. Pat. No. 11,351,370 entitled "Devices and Methods for Treating Cognitive Dysfunction and Depression Using Electrical Stimulation" and issued Jun. 7, 2022. All above identified applications are hereby incorporated by reference in their entireties.

BACKGROUND

Improper blood management can be life threatening. After an injury occurs, the amount of blood lost must be minimized.

Close to 20 years ago, vagal stimulation was proposed by the inventors of U.S. Pat. No. 8,729,129, including inventor Christopher Czura of the present application, as a potential solution to inducing a shorter bleeding time as well as a lower bleeding volume in humans. The inventors published mouse data derived from trials using implantable vagus stimulation. Interestingly, although they were able to show a bleeding reduction, they were unable to show a significant change in prothrombin time (PT) (see, e.g., FIG. 5 of U.S. Pat. No. 8,729,129). PT assesses the time takes platelets to coagulate. That is, they were unable to show an increase coagulation activity/coagulation rate or what we are calling the coagulation potential (CPot—as used herein meaning the potential ability to speed up coagulation; in particular, at an injury site). In 2017, inventors including the same individuals named in U.S. Pat. No. 8,729,129 proposed, in an application eventually granted as U.S. Pat. No. 10,912,712, a non-invasive approach using mechanical stimulation purported to achieve similar results. However, as in the previous patent, the only data presented in relation to bleeding modulation in U.S. Pat. No. 10,912,712 was obtained in rodents using implantable electrostimulation. Again in 2019, inventors including two of same individuals named in U.S. Pat. No. 8,729,129 proposed the use of both invasive and non-invasive trigeminal stimulation to achieve bleeding control in a further application recently granted as U.S. Pat. No. 11,660,443. As in the earlier patents listed above, only data collected from rodent trials using subdermal electrodes was presented. A few months later, a patent application assigned to the same institution and naming a different inventor proposed the combined use of trigeminal and vagal stimulation to control bleeding, resulting in the grant of U.S. Pat. No. 11,260,229. In contrast to the previous applications, no data was presented in this last application.

Additionally, despite a long-felt need in the medical community for bleeding control and ongoing publication on the topic of bleeding control using neural stimulation, not only has no commercial solution appeared but, to the knowledge of the present inventors, no human subject data demonstrating significant bleeding control results has been published prior to the data presented within this application. Instead, only small animal experiments exist to date to the inventors' knowledge, the studies involving major neck surgery to access the vagus nerve and stimulate it using an implantable electrode in direct contact with the nerve. Due to the invasive nature of these studies, they were not readily replicable on human subjects.

In every bleeding or potential bleeding scenario, the loss of blood volume must be minimized; furthermore, when bleeding volume is such that it could lead to hypovolemia, then perfusion and oxygenation of tissues, in particular brain tissue, must be enhanced to prevent permanent damage and possible death. Furthermore, some hemorrhages, whether or not they lead to hypovolemia, may lead to sepsis. For example, risk of sepsis is increased by some postpartum hemorrhage treatments as well as in patients with intracerebral hemorrhage. Both hypovolemia and sepsis lead to high levels of systemic inflammation with pro-inflammatory cytokines being released into circulation. In cases of sepsis, not only perfusion and oxygenation of tissue is important but also a reduction of inflammation and circulating pro-inflammatory cytokines is needed to avoid further complications as well as organ damage or failure. Moreover, sepsis can actually lead to hypovolemia. This being said, the leading cause of sepsis is not hemorrhage but infection. Sepsis is an extremely costly and resource-intense condition; for example, in the United Kingdom it has been estimated that sepsis patient account for about one third of hospital bed-days and just below half (~45%) of Intensive Care Unit (ICU) bed-days. In the U.S., at an average of more than $18,000 per hospital stay and an annual cost of $24 billion, sepsis is the most costly condition. Sepsis represents 13% of all U.S. hospital expenditures although it only accounts for approximately 3.5% of hospital stays.

The inventors recognized a need for new systems and methods designed to mitigate blood loss following an injury while increasing oxygenation and/or perfusion of brain tissue when blood loss is large and/or blood flow is significantly impacted. Further, the inventors recognized the need to achieve lower systemic inflammation during blood loss mitigation as well as within a septic episode. Additionally, the inventors recognized the need to mitigate the possibility of bleeding in a prophylactic manner before any bleeding occurs by increasing an individual's coagulation potential. Advantageously, the new systems and methods can be easily and rapidly applied in a non-invasive manner, at a home, in a clinical setting, and/or in field environments.

SUMMARY OF ILLUSTRATIVE EMBODIMENTS

Some people use the term hypovolemia to describe both the whole body fluids as well as a decrease in vascular fluid volume. In the present description, hypovolemia is used to describe the latter scenario. Furthermore, hypovolemia is classified according to severity; however, in the present document, hypovolemia is used to describe a significant loss of blood volume such that tissue oxygenation and perfusion is such that may lead to organ dysfunction or failure.

Sepsis can be described as an immune overreaction leading the release of pro-inflammatory cytokines and to systemic inflammation. As with hypovolemia, sepsis is also classified depending on severity. If untreated, sepsis tends to progress increasing in severity and can lead to organ dysfunction or failure. Interestingly, as it is explained later, reducing sepsis and achieving hemostasis faster can be attained by modulating spleen activity.

In one aspect, the present disclosure relates to systems and methods for incrementing the coagulation potential (CPot) in a mammal, including humans.

In some embodiments, a transient increase in the coagulation potential is produced by triggering spleen activity to treat an acute scenario. For example, spleen activity may be triggered by activating the splenic nerve via stimulation of vagal descending or vagal efferent nerve fibers (VEF). The splenic nerve and/or, directly, the spleen could also be stimulated in a non-invasive manner using ultrasound (e.g., focus or confocal ultrasound/high intensity ultrasound). The acute scenario, in some examples, can include injury potentially leading to significant blood loss, a surgical or other medical procedure including significant likelihood of bleeding, a medical procedure having a likelihood of bleeding during a recovery stage, and/or temporary systemic conditions such as nosebleeds, abnormal uterine bleeding, and/or heavy menstrual bleeding including menorrhagia.

In some implementations, systems and methods described herein for stimulating the spleen directly and/or indirectly (e.g., via VEF, the splenic nerve, and/or the splenic ganglion) are used in a preventive/prophylactic fashion. In illustration, stimulation may be performed prior to an anticipated event, for example prior to the menstrual cycle, or prior to a surgical procedure, such as during a period of time leading up to the event and during the event itself as well as after the event, to prevent or minimize future bleeding. The stimulation, for example, may be provided prior to and/or during surgery in part to overcome an effect of an anticoagulant drug in the system of the patient. In this manner, stimulation may provide the benefit of accelerating approval time for a patient in need of surgery who has been taking anticoagulant medication, such as for treatment of blood clots.

In some implementations, systems and methods described herein for stimulating the spleen directly and/or indirectly (e.g., via VEF, the splenic nerve, and/or the splenic ganglion) are used in a corrective/therapeutic fashion. For example, stimulation may provide the benefit of protection to a patient having emergency surgery without opportunity to wean anticoagulant medication from his or her system. In another example, stimulation may be performed after surgery to accelerate coagulation and thereby shorten a post-surgical recovery time, such as a time for wound (e.g., surgical access site) closure. In some scenarios, the surgical team may use a combination of hemostatic approaches, for example, by applying VEF stimulation along with another available hemostat(s). In some scenarios, non-invasive VEF stimulation maybe used to identify people that respond to therapy (responders) by showing an increase in Cpot prior to utilizing an invasive approach (e.g., implanting electrodes to stimulate the vagus and/or the splenic nerve).

In certain embodiments in which a transient increase in coagulation potential is desired in a therapeutic scenario, such as in a post-bleeding application or in a pre-surgical scenario, direct and/or indirect stimulation of the spleen is started as soon as possible and sustained as needed to speed up the ongoing coagulation process and thus limit blood loss. In this type of scenario, stimulation may be continuously applied until bleeding stops. After bleeding has ceased, stimulation may continue to be applied, as in the prophylactic scenarios described above, to prevent further bleeding. Upon stopping stimulation, the coagulation potential would gradually go back to its pre-stimulation levels.

In some embodiments, direct and/or indirect spleen stimulation (e.g., via VEF, the splenic nerve, and/or the splenic ganglion) is performed to achieve a sustained increase in the coagulation potential to treat a chronic scenario, such as the ones previously described. Further, spleen stimulation, in some embodiments, is performed to achieve a sustained increase in the coagulation potential in scenarios in which a chronic coagulation deficiency exists like in the case of people suffering from hemophilia (e.g., hemophilia A, B, or C), von Willebrand Disease (vWD), as well as other clotting factor related deficiencies (e.g., Factor I deficiency, Factor II deficiency, Factor V deficiency, Factor VII deficiency, Factor X deficiency, Factor XII deficiency, or Factor XIII deficiency) and/or other chronic conditions such as Bernard-Soulier syndrome and Glanzmann thrombasthenia.

In some embodiments involving chronic coagulation deficiency, non-invasive indirect and/or direct stimulation of the spleen can be applied by a clinician while exploring the viability of an implantable solution. For example, the stimulation may be performed in a clinical environment to test whether a patient is responsive to the stimulation therapy. If the viability study is successful, the patient may be offered the option to receive an implantable device rather than relying upon the external stimulation therapies as described herein. The viability study may involve multiple stimulation therapy sessions. The multiple therapy sessions may include multiple electrode placements, multiple stimulation patterns, multiple stimulation intensities, and/or multiple stimulation session durations to assess patient response to VEF stimulation.

In some embodiments, stimulation of the spleen (e.g., directly and/or indirectly) is applied to achieve a transient anti-inflammatory response, for example in a preventive/prophylactic or corrective/therapeutic fashion. In a preventive/prophylactic application, for example, VEF, splenic ganglia, celiac ganglia, and/or spleen stimulation can be applied before a scheduled event from which a pro-inflammatory response is expected, such as before a scheduled surgical procedure or extraneous physical activity, like in the case of a baseball pitcher who may expect an inflammatory response after pitching. In a corrective/therapeutic application, for example when an inflammatory response has already begun, such as in the case of trauma, infection, or a sepsis or potential sepsis scenario, VEF, splenic ganglia, celiac ganglia, and/or spleen stimulation can be applied as soon as possible and sustained as needed to trigger, maintain, and/or speed up the anti-inflammatory response. In these types of scenarios, the stimulation can be continuously applied until the desired response is obtained, and after as in the prophylactic scenarios described above to prevent further inflammation.

In one aspect, by stimulating trigeminal branches the present disclosure relates to triggering an increase in cerebral blood flow either by increasing blood pressure and/or by increasing blood vessel patency; herein referred to as a pressor response. For example, the pressor response may be triggered to transiently treat or prevent hypovolemic damage to tissue including brain tissue, in a scenario when a large volume of blood has been lost or when there is a potential for a large blood volume to be lost. In illustration, triggering the pressor response may be beneficial in scenarios involving a penetrating and/or non-compressible injury (e.g., a bullet or knife wound, a large cut, or in an internal bleeding scenario such as gastrointestinal bleeding). The stimulation, for example, may be applied as soon as possible, and sustained as needed to trigger, maintain, and/or speed up the desired response.

In one aspect, the present disclosure relates to triggering a trigemino-parasympathetic response (TPSr) by stimulating Arnold's nerve (a.k.a. the auricular branch of the vagus nerve—ABVN) and/or the auriculotemporal nerve (ATN). In another aspect, the present disclosure relates to triggering an increase CPot via modulation of VEF activity by stimulating Arnold's nerve and/or the ATN. In some embodiments, both a TPSr as well as an increase in CPot are triggered. The triggered TPSr and/or the increase in CPot, for example, may be used to transiently treat or prevent hypovolemic tissue damage to different organs including the brain in a scenario in which a large volume of blood has been lost or when there is a potential for a large blood volume to be lost. In illustration, triggering the TPSr and/or an increase in CPot may be beneficial in scenarios involving a penetrating and/or non-compressible injury (e.g., a bullet or knife wound or an internal bleeding scenario). The stimulation, for example, may be applied as soon as possible, and sustained as needed to trigger, maintain, and/or speed up the desired response.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
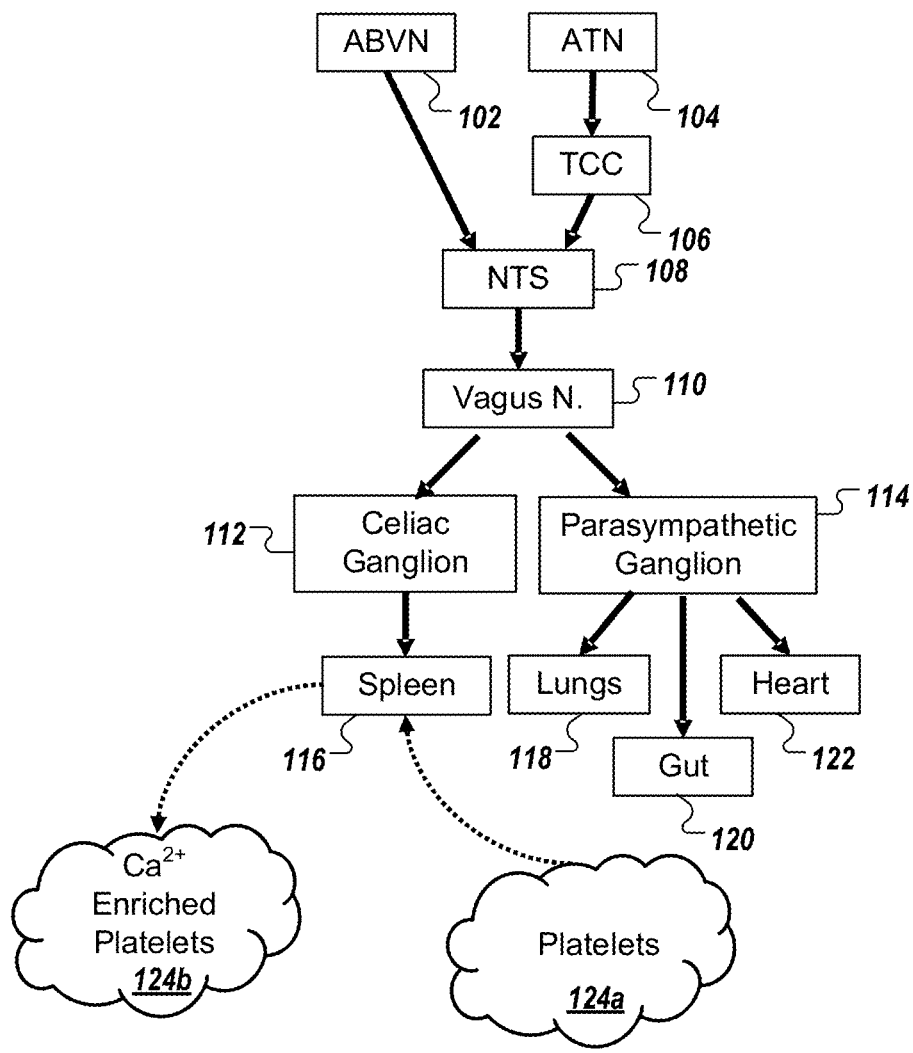
FIG. 1 is a block diagram of an example anti-inflammatory pathway.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Although hypovolemia has been used to describe both the whole-body fluids as well as a decrease in vascular fluid volume, in the present disclosure, the term hypovolemia references the latter definition. Generally, hypovolemia is classified according to severity; however, in the present disclosure, hypovolemia applies to circumstances involving a significant loss of blood volume involving tissue oxygenation and/or perfusion effects that may lead to organ dysfunction or failure.

Sepsis can be described as an immune overreaction leading to the release of pro-inflammatory cytokines and to systemic inflammation. As with hypovolemia, sepsis is also classified depending on severity. If untreated, sepsis tends to progress increasingly in severity and can lead to organ dysfunction or failure which in some cases can result in death. As explained later, reducing sepsis and achieving hemostasis faster can be attained by modulating spleen activity.

Hemostasis

Hemostasis, the process by which bleeding is stopped, is generally triggered by molecules that become exposed to circulating blood at a site of vascular injury. Sub-endothelial collagen (SEndC) and Tissue Factor (TF, aka coagulation Factor 3 or fIII) are examples of such molecules. While circulating platelets (i.e., thrombocytes) bind to exposed SEndC, TF binds to a particular circulating molecule called coagulation Factor 7 (fVII). The interaction between TF and fVII leads to the activation of fVII (fVIIa) and to the formation of the TF-fVIIa complex, which is called the Extrinsic Tenase (i.e., Extrinsic Xase). This TF-fVIIa complex initiates what is known as the coagulation cascade by activating coagulation Factor 10 (fX) and coagulation Factor 9 (fIX) into fXa and fIXa respectively (see below). Platelets adhering directly or indirectly to SEndC start to aggregate and form the initial plug to stop the bleeding. This plug is known as the platelet plug or thrombus. The platelet plug is then reinforced by the adherence and crosslinking of fibrin. The process leading to the formation of the platelet plug is commonly referred to as primary hemostasis whereas the process leading to the reinforcement of it by crosslinked fibrin (i.e., activated coagulation factor 1 or fIa) is known as secondary hemostasis. Platelets are anucleate blood cells mainly produced in bone marrow from megakaryocytes. Under normal conditions about 100 billion platelets are produced daily, leading to a concentration in blood that ranges between 150 to 400 million per milliliter. Platelets enter the vasculature circuit and, in humans, circulate for approximately 7 to 10 days before being removed by the liver and the spleen. Interestingly, as they circulate, they pool in the spleen where about a third of all circulating platelets are located at any given time. In humans, platelets transit time through the spleen is approximately 30 minutes.

Platelets contain, amongst others, mitochondria and two types of granules, the alpha granules ($\alpha G$) and the dense or delta granules ($\delta G$). Ionized calcium ($Ca^{2+}$ aka coagulation Factor 4 or fIV), a key component for coagulation, is stored inside the platelet at least within the mitochondria, the Dense Tubular System (DTS), as well as within the delta granules. Platelets circulate in the blood in an inactivated state and as such they do not aggregate; however, platelets become activated when they bind to exposed SEndC following an injury.

Platelets bind to SEndC directly via either the GP VI or the GP Ia/IIa receptors or indirectly through von Willebrand factor (vWF) via GP Ib-V-IX receptor. An activated platelet undergoes a shape change and secretes through its membrane the contents of its granules. The contents of the alpha granules include, among other components, fibrinogen (a.k.a. coagulation factor 1 or fI), platelet-derived growth factor (PDGF), vWF, TGF beta, coagulating Factor 5 (fV), platelet factor 4 (Pf4), and insulin-like growth factor 1 (IGF1). Delta granules ($\delta G$) contain, among other components, $Ca^{2+}$, ADP, ATP, and serotonin (5-HT). Activated platelets promote changes to membrane receptors GP IIb/IIIa (aka integrin $\alpha IIb\beta 3$) such that these receptors can bind to vWF as well as to fibrinogen. In addition, Thromboxane A2 (TxA2) is secreted from activated platelets. TxA2, and ADP activate circulating platelets which begin to aggregate with other activated platelets via GP IIb/IIIa-vWF-GP IIb/IIIa and GP IIb/IIIa-fibrinogen-GP IIb/IIIa bridges. This aggregation gives rise to platelet accumulation at the injury site generating the aforementioned platelet plug. This platelet plug, although weak, is the first step in limiting and eventually stopping blood from leaving the vascular system. Clot retraction is greatly influenced by the presence of the GP IIb/IIIa receptor on the platelet surface. Clot retraction assists in healing the wound by bringing the separated edges of the wound closer and closer together until the wound is healed. Thus, by promoting changes to the GP IIb/IIIa receptor, subjects that undergo therapy as described herein will enjoy the further benefit of accelerated time to heal.

As also mentioned earlier, the plug is then reinforced by fibrin fibers and further by the crosslinking of them by activated coagulation Factor 13 (fXIIIa). Fibrin is produced when circulating as well as platelet-secreted fibrinogen is converted into fibrin by thrombin (i.e., activated coagulation Factor2 or fIIa). In turn, thrombin is produced by cleavage from circulating prothrombin (a.k.a. coagulation factor 2—fII). Thrombin can be produced from prothrombin in relatively small amounts by fXa bound to platelet surfaces. Thrombin is not only able to turn fibrinogen into fibrin but it can also activate other platelets as well as convert fV, coagulation Factor VIII (fVIII), coagulation Factor XI (fXI), and coagulation Factor 13 (fXIII) into their activated forms (fVa, fVIIIa, fXIa, fXIIIa respectively). fVa binds to fXa on the platelet surface in a $Ca^{2+}$ dependent manner to form prothrombinase (fXa-fVa complex). The prothrombinase complex is capable of converting large quantities of prothrombin into thrombin. In fact, the prothrombinase complex cleaves thrombin from prothrombin at a rate that is hundreds of thousands of times faster (e.g., approximately 250,000 times) than fXa alone. Consequently, the presence of prothrombinase on the platelet surface greatly accelerates the coagulation process.

As stated before, fX can be activated into fXa by the Extrinsic Tenase; however, fX can also be activated by the Intrinsic Tenase, which is composed of fVIIIa and fIXa. In order for the Intrinsic Tenase to be assembled, both fVIII and fIX need to be activated. Thrombin can activate fVIII, and the Extrinsic Tenase and fXIa can activate fIX.

Figure 4:
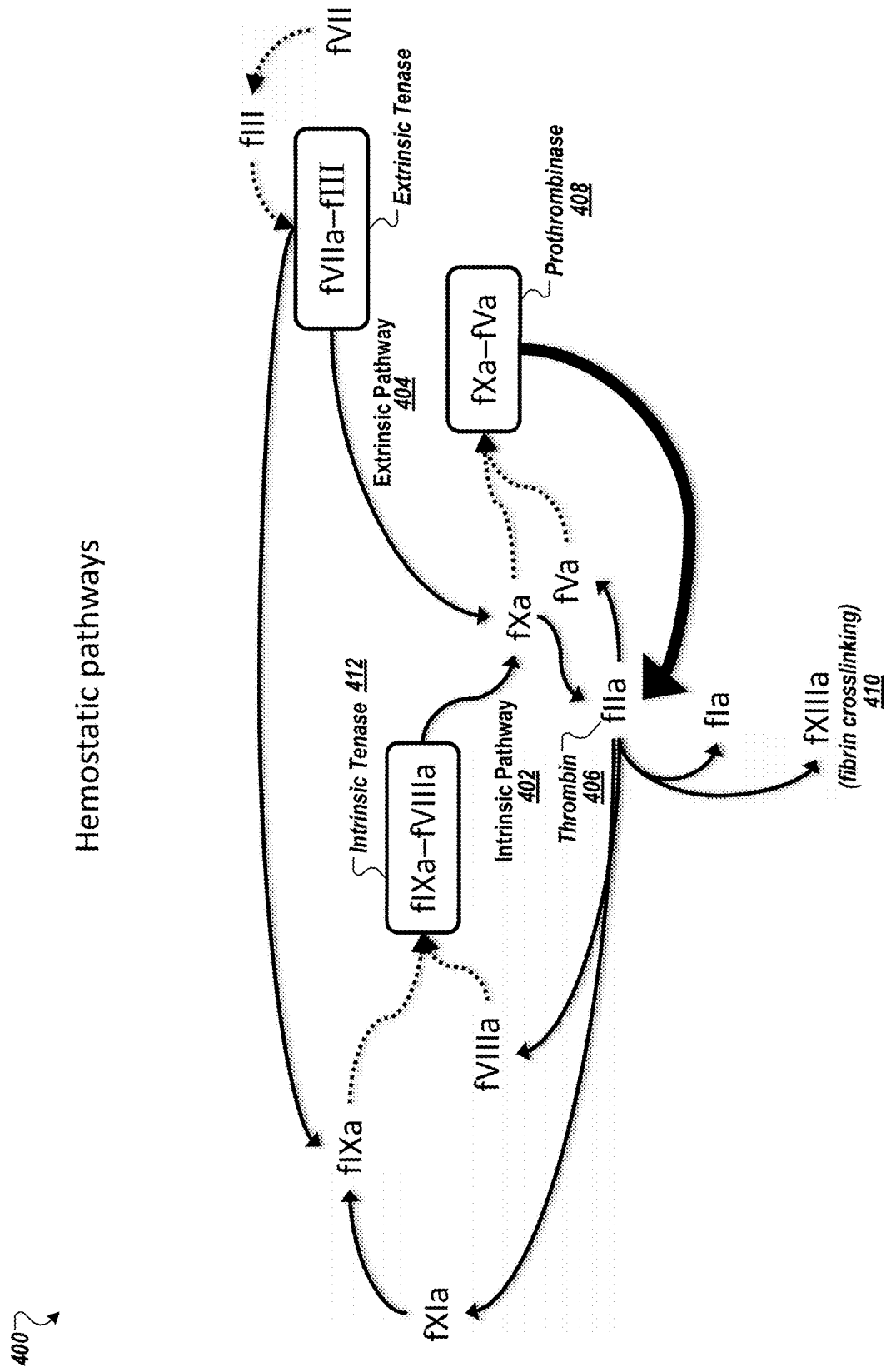
FIG. 4 is a block diagram of example hemostatic pathways.

The pathway in which fXa is activated by the Extrinsic Tenase is generally known as the Extrinsic Pathway, and that in which fXa is activated by the Intrinsic Tenase is called the Intrinsic Pathway. The coagulation steps after the activation of fXa until the fibrin crosslinking by fXIIIa are termed the Common Pathway. As it can be appreciated from the text as well as from FIG. 4, which depicts the hemostatic pathways 400, the role of thrombin is essential for hemostasis to take place.

Important to note is the remarkable quantitative difference between the Intrinsic Pathway 402 and Extrinsic Pathway 404. Under normal circumstances, compared to the Extrinsic Pathway 404, thrombin 406 is produced between 50 to 100 times faster via the Intrinsic Pathway 402. Thus, it would be reasonable to state that under normal conditions the Extrinsic Pathway 404 initiates the hemostatic process, but it is the Intrinsic Pathway 402 that gets it to the finish line.

Platelets are not homogeneous; they exhibit marked differences which become evident after platelet activation during hemostasis. One of the most consequential differences amongst platelets subpopulations is that some activated platelets become procoagulant (although under debate, some refer to them as procoagulant collagen- and thrombin-activated or COAT platelets) while others activate into noncoagulating platelets (pro-aggregatory platelets). Whereas most of the thrombin 406 is produced by procoagulant platelets, noncoagulating platelets are more prone to aggregate; thus, both types are needed for proper coagulation. Although there is large variability from subject to subject, on average, only 30% of activated platelets become procoagulant platelets.

In many or possibly all cases, procoagulant platelets swell and their phospholipid membrane becomes more negative due to exposure of phosphatidylserine (PS) on their membrane surface. Platelet membranes becoming more negative results in a significant increase in the binding affinity of prothrombinase to them; thus prothrombinase is much more likely to bind to procoagulant platelets (pCP) than to noncoagulating (nCP) ones. Since, as mentioned before, prothrombinase 408 can produce thrombin 406 up to two hundred and fifty thousand times (250,000 times) faster than fXa alone, it is clear that most of the thrombin 406 at or near the injury site will be produced on pCP.

Given the hemostatic processes discussed above, it is evident that even small increases in the pCP/nCP ratio can increase the rate of thrombin production at or near the injury site, thus accelerating platelet and fXIII activation as well as fibrin production. Thus, in addition to leading to faster platelet aggregation, increases in thrombin generation also leads to increases in the rate of fibrin binding and crosslinking 410 which altogether promotes shorter bleeding times and lower bleeding volumes.

Further, faster/higher production of thrombin 406 at the injury site can compensate deficits and limitations in the hemostasis process (e.g., bleeding/coagulation disorders), such as, for example, a lower production or a lack of Intrinsic Tenase 412 production due to deficiencies or lower than normal (including complete lack of) fVIII, fIX, or fXI, which is respectively the case in Hemophilia A, Hemophilia B, and Hemophilia C. Interestingly, studies have shown that, compared with healthy individuals, the levels of pCP is significantly lower in individuals suffering from hemophilia. As mentioned earlier, vWF facilitates platelet adhesion to endothelial tissue at an injury site as well as it supports platelet-to-platelet adhesion after platelet activation at or near an injury site. In addition, vWF serves as a carrier for fVIII in plasma in the form of a vWF-fVIII complex. Consequently, lower amounts of circulating/available fVIII are also seen in vWD type 2N. Since a faster/higher production of thrombin 406 leads to a higher platelet activation rate, and thus to a higher fibrinogen release rate, another circumstance leading to a deficiency and/or limitation in the hemostasis process that could be compensated by faster/higher production of thrombin 406 at or near the injury site is when there is a lower platelet adhesion and aggregation due to a lower count or lack of available or fully functional vWF such as for example, in vWD type 1, type 2A, type 2M, and type 3. Yet another example in which higher/faster thrombin production can compensate existing deficiencies in hemostasis is in the case of vWD type 2B, which leads to both lower adhesion/aggregation of platelets as well as a lower platelet count. By compensating it is not suggested that in any of the cases the hemostasis process would be restored to what would be expected in a normal subject (e.g., where deficits and limitations are not present). Instead, the term compensate is used to refer to a significantly faster hemostasis process than that which otherwise occurs in light of the deficiencies and limitations without the extra amount of thrombin present. One manner in which this compensation may occur is by locally increasing the ratio of procoagulant/anticoagulant activity at or near the injury site.

A strong activation is necessary for a platelet to activate as a procoagulant platelet (pCP); however, this is not sufficient. Experiments using double agonist (e.g., collagen and thrombin) have been shown to produce a small percentage of platelet activation into procoagulant types. Some have suggested that the COAT acronym is inaccurate since not only is activation by both collagen and thrombin insufficient to provide a considerable boost in platelet activation into procoagulant types, but it is also not unique. It is not unique in the sense that a very large concentration of thrombin can also activate platelets into procoagulant types. Several elements have been identified as contributing factors to determining whether or not, upon activation, a platelet becomes procoagulant. Some of these elements include platelet age, size, number of mitochondria, number as well as content of granules, and baseline $Ca^{2+}$ concentration. Interestingly, under similar circumstances, younger platelets are more likely to become procoagulant than older ones (as stated earlier, in humans, platelets circulate for about 7 to 10 days before being removed by the liver and/or spleen).

Data from a recent study by Abbasian and colleagues showed that the cytosolic $Ca^{2+}$ concentration ($[Ca^{2+}]_{cyt}$) in pCP was at least 50 times higher than the $[Ca^{2+}]_{cyt}$ in nCP (>100 nM vs. 1-2 nM). See Abbasian, Nima, et al. "Supramaximal calcium signaling triggers procoagulant platelet formation." Blood Advances 4.1 (2020): 154-164. Most platelets can activate as pCP if treated with $Ca^{2+}$; however, in general, most platelets activate as nPC if stimulated with some platelet activators. This suggests that $[Ca^{2+}]_{cyt}$ is one, if not the most significant, factor in determining if a platelet activates as a pCP or as a nCP.

Platelets have several transmembrane $Ca^{2+}$ channels which allow $Ca^{2+}$ exchange between extracellular and intracellular spaces (see table below). More than one of these channels or a combination of them could be activated to allow a net positive $Ca^{2+}$ influx, thus incrementing the total amount of $Ca^{2+}$ in the platelet. Within the platelet, this $Ca^{2+}$ is usually taken by one or various mechanisms into internal storages, amongst which are the mitochondria, the dense tubular system (DTS), lysosomes, and the δG. A high $[Ca^{2+}]_{cyt}$ could lead to platelet activation, which if it happens at a location other than at an injury site, may lead to an undesired thrombotic event. Thus, it is important that $Ca^{2+}$ is sequestered into internal (e.g., intracellular) storages such that it is only released into the cytosolic space upon an injury-related activation. This could be achieved in different ways; for example, by inducing an influx of $Ca^{2+}0$ into the platelet by activating one of the transmembrane $Ca^{2+}$ channels and temporarily or transiently blocking or partially blocking the mechanisms responsible for the release of $Ca^{2+}$ from internal storages into the cytosolic space. This rise in baseline $Ca^{2+}$ (e.g., total intracellular pre-activation $Ca^{2+}$ not in the cytosolic space) can increase the likelihood of higher $[Ca^{2+}]_{cyt}$ upon activation, thereby incrementing the overall probability for platelets to activate as pCP, leading to a higher coagulation potential. In the event of an injury, a higher coagulation potential translates, on an individual basis, to a higher thrombin production at the injury site. A higher than otherwise production of thrombin at an injury site translates into a faster and localized platelet activation as well as fibrin adhesion and crosslinking onto the thrombus. Therefore, a higher coagulation potential can result in a faster coagulation process leading to lower bleeding volumes and shorter bleeding times.

TABLE 1

Platelet Transmembrane Calcium Channels
Platelet Transmembrane Calcium Channel Table

| Channel | Calcium flow |
|---|---|
| α7-Nicotinic Acetylcholine Receptor (nAChRα7) | IN |
| calcium-release activated calcium modulator 1 (CRACM1 or Orai1) | IN |
| Canonical Transient Receptor Potential 6 (TRPC6) | IN |
| Purinergic receptor, P2X1 | IN |
| Na$^+$/Ca$^{2+}$ exchanger | IN |
| plasma membrane Ca$^{2+}$ ATPases (PMCAs) | OUT |

As shown by Schedel and colleagues, platelets express the α7-Nicotinic Acetylcholine Receptor (nAChRα7). See Schedel, Angelika, et al. "Human platelets express functional α7-nicotinic acetylcholine receptors." Arteriosclerosis, thrombosis, and vascular biology 31.4 (2011): 928-934. Since the autonomic nervous system (ANS) can control the release of Acetylcholine (ACh), and given that the nAChRα7 is a transmembrane $Ca^{2+}$ channel, the presence of nAChRα7 on the platelet membrane suggests that platelet $Ca^{2+}$ influx can be modulated by the ANS. Further, since Bennett, et al. showed that ACh inhibits platelet activation, it follows that ACh can be used to increase $Ca^{2+}$ via the nAChRα7 while preventing platelet activation. See Bennett J A, Ture S K, Schmidt R A, Mastrangelo M A, Cameron S J, Terry L E, Yule D I, Morrell C N, Lowenstein C J. Acetylcholine Inhibits Platelet Activation. J Pharmacol Exp Ther. 2019 May; 369(2):182-187. For example, as illustrated in FIG. 1, platelets 124a circulating in the spleen 116 may be enriched to produce $Ca^{2+}$ enriched platelets 124b by activating VEF, triggering cells in the celiac ganglion 112. The splenic ganglion and/or the spleen 116, in another example, may be stimulated directly and/or indirectly to enrich the platelets 124a circulating in the spleen 116 to produce $Ca^{2+}$ enriched platelets 124b.

For simplicity, we are referring to singular ganglion, however, both left and right celiac ganglia are connected and thus activity in one ganglion affect the activity on the other, thus although, in the present document, activity in one ganglion is most often reference, it should be understood that any reference to a certain ganglion encompasses reference to both right and left ganglia when they exist.

Interestingly, the sympathetic and parasympathetic fibers interact at the celiac ganglia, where both can influence the activity of postganglionic sympathetic fibers enervating the spleen. In particular, sympathetic preganglionic efferent fibers (SPgF) normally coming from the T5-T9 spinal cord levels leave the spine as the spinal root that becomes the greater splanchnic nerve and synapse onto postganglionic neurons at the celiac ganglion. The SPgF release ACh as they synapse on their target at the celiac ganglia. Fibers leaving the celiac ganglia form what is known as the celiac plexus, fibers from which continue as the splenic plexus. The splenic nerve, which arises from fibers in the splenic plexus, enervates the spleen. The activity of the SPgF is modulated, amongst other things, by activity in the RVLM, which in turn is modulated by activity in both the TCC and the LC. It is worth noting that the ABVN also connects to trigeminal regions, in particular to the trigeminal spinal nucleus, which for purposes of the present document is considered part of the TCC. Consequently, activation of SPgf via, amongst others, activity in the TCC and/or in the LC and/or the activation of the VEF can modulate the production of $Ca^{2+}$ enriched platelets via a common pathway following their interaction at the celiac ganglia.

Figure 3A:
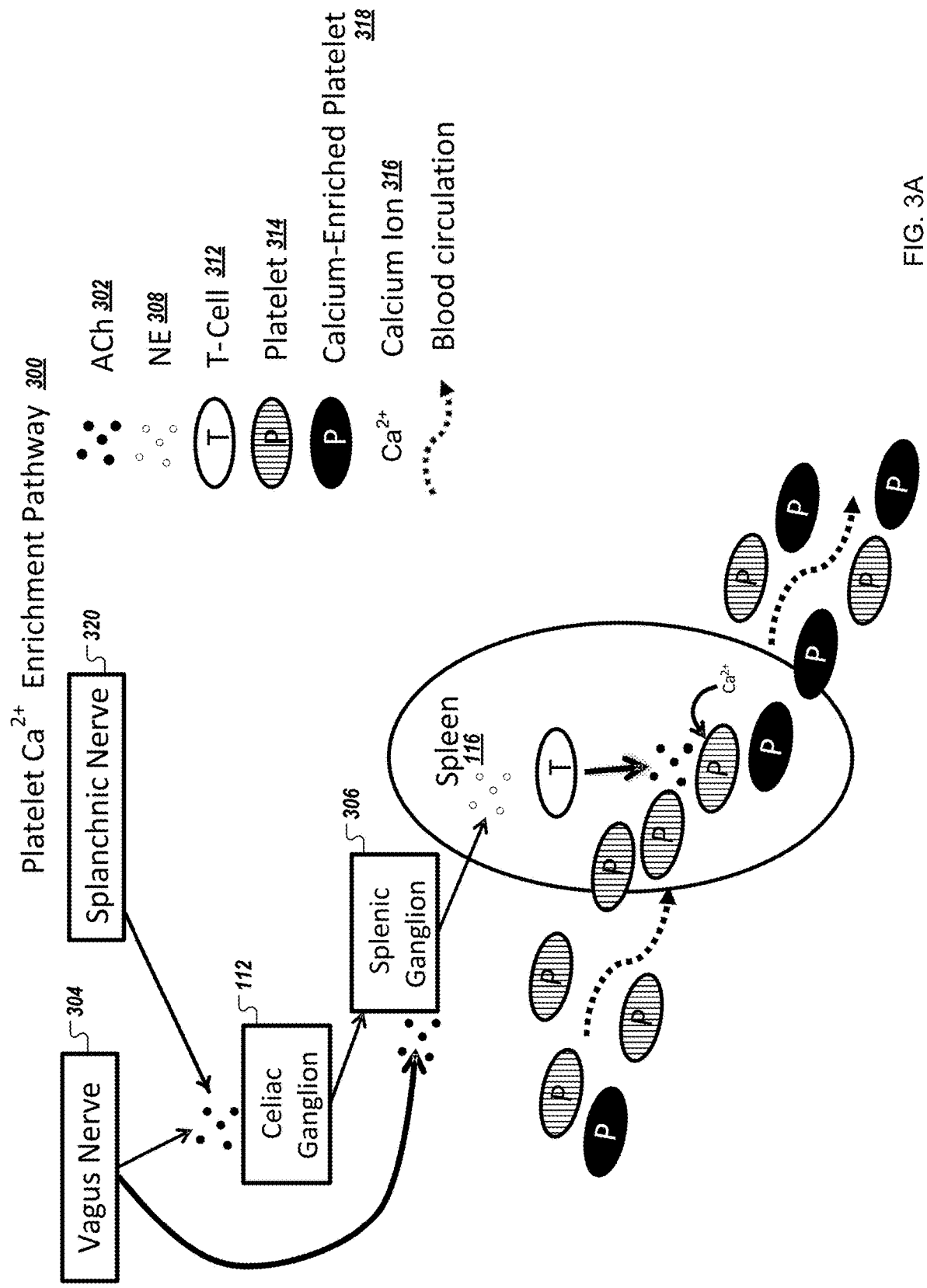
FIG. 3A is a block diagram of an example platelet calcium-enrichment pathway.

Turning to FIG. 3A, an example block diagram of a platelet $Ca^{2+}$ enrichment pathway 300 is illustrated. Acetylcholine (ACh) 302, a natural agonist of the nAChRα7, is an important neurotransmitter that modulates many aspects in the ANS. Increasing activity in the parasympathetic branch of the ANS (e.g., the parasympathetic nervous system— PNS), for example by activating VEF 304, can trigger the release of ACh 302 in the celiac ganglion 112 and/or in the splenic ganglion 306. The same is true when increasing the activity of the splanchnic nerves 320 synapsing on the celiac ganglion 112, as they too release ACh 302. Innervation of the spleen 116 is carried out via neural connections between the splenic ganglion 306 and their targets in the spleen 116, where norepinephrine (NE) 308 is released. Interestingly, Rosas-Ballina showed that NE 308 released in the spleen 116 activates T-cells 312 which in turn releases ACh 302. See Rosas-Ballina et al. Acetylcholine-synthesizing T cells relay neural signals in a vagus nerve circuit. Science. 2011 Oct. 7; 334(6052):98-101. doi: 10.1126/science.1209985. Epub 2011 Sep. 15. PMID: 21921156; PMCID: PMC4548937. This ACh 302, upon reaching the nAChRα7 on the platelets 314 which are slowly circulating through the spleen 116, can trigger a $Ca^{2+}$ 316 influx into the platelets 314 effectively increasing their baseline $Ca^{2+}$ 316 and resulting in calcium-enriched platelets 318, which may also be referred to herein as primed platelets. This detailed description refers to the celiac ganglion and to the splenic ganglion 306; however, the splenic ganglion 306 is sometimes considered an extension of the celiac ganglion 112. Further, it is understood that many ganglia form what is called a plexus (e.g., plexus 306). As such, for the purpose of the description herein, plexus and ganglion are interchangeable.

Figure 3B:
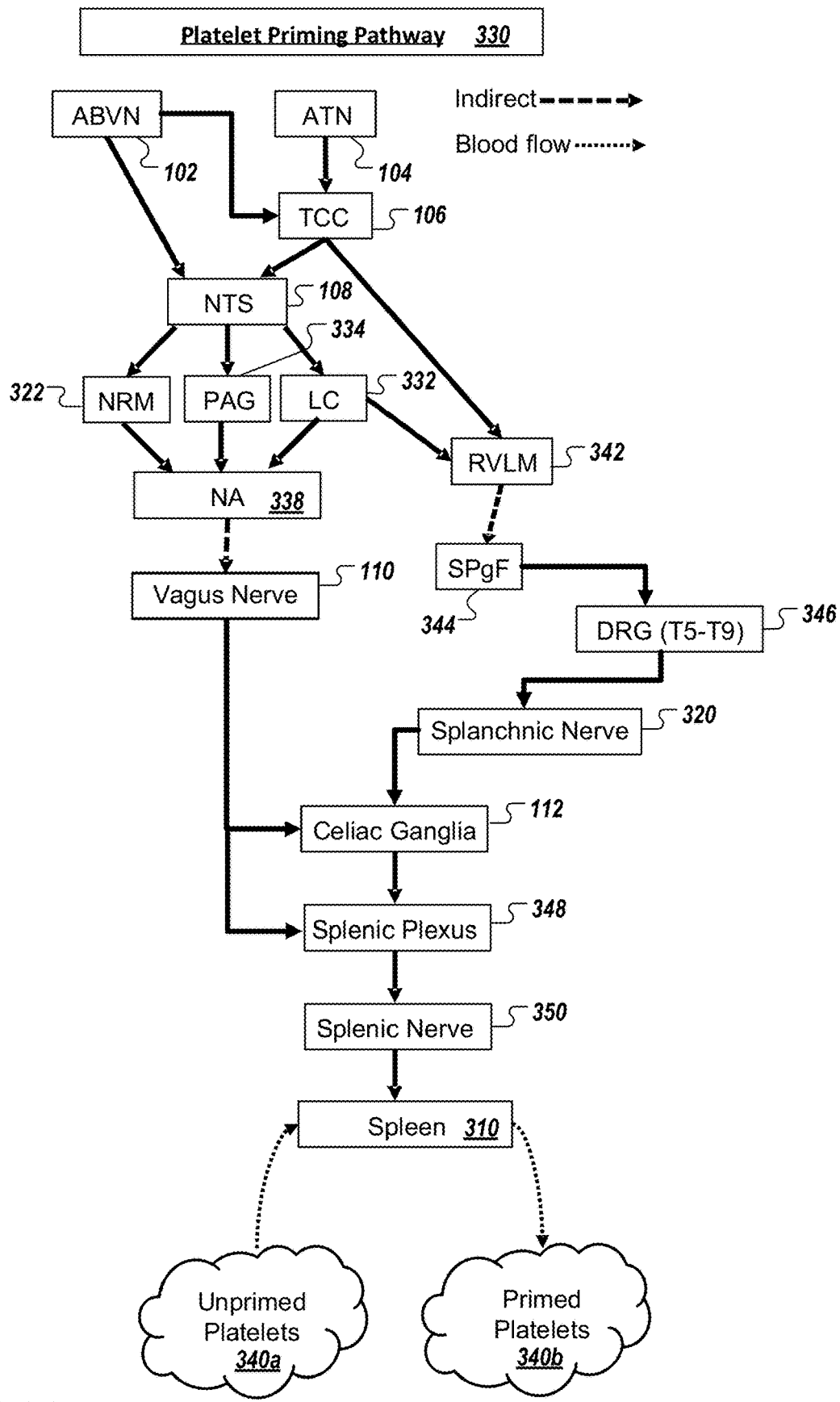
FIG. 3B is a block diagram of an example platelet priming pathway.

Turning to FIG. 3B, in some embodiments, platelets are primed via activation of a Platelet Priming Pathway 330 which stimulates activity in the spleen 310. In particular, the ABVN 102 and/or the ATN 104 may be stimulated which have projections to the NTS 108. As illustrated, the TCC 106 receives afferent connections from the ATN 104 and projects to the NTS 108 as well as to the RVLM 342, while the ABVN 102 projects directly to the NTS 108.

As seen in FIG. 3B, certain platelet priming pathways also involve other nuclei or regions such as Locus Coeruleus (LC) 332, Periaqueductal Gray (PAG) 334, and nucleus raphe magnus (NRM) 322. Each of these nuclei or regions feed, in turn, to the nucleus ambiguous (NA) 338 which provides a pathway to the vagus nerve 110. Other regions also feeding the vagus nerve 110 are the dorsal motor nucleus of the vagus (DMV) (not illustrated) as well as the spinal trigeminal nucleus (herein considered part of the TCC 106). The indirect stimulation of the vagus nerve 110 via the various pathways allows the vagus nerve 110 to enervate the celiac ganglia 112 and/or the splenic plexus 348. The splenic nerve 350, which arises from fibers in the splenic plexus 348, enervates the spleen 310, thereby increasing platelet priming in the spleen 310, resulting in more unprimed platelets 340a being converted to primed platelets 340b. For example, stimulation using a low mid-range pulse at a low frequency on the Arnold's nerve, and/or a low mid-range pulse at a high frequency on the ATN for a short duration may lead to a noticeable increase in primed platelets, which, for example, could be assessed by a decrease in PT.

In another path illustrated in FIG. 3B, the LC 332 and TCC 106 each provide a pathway to the RVLM 342 which provides a pathway for indirectly stimulating the sympathetic preganglionic efferent fibers (SPgF) 344, which exit the spine via the dorsal root ganglion (DRG) at the T5-T9 level 346 to form the greater splanchnic nerve 320 leading to the stimulation of postganglionic nerves at the celiac ganglia 112, further triggering splanchnic nerve 320 activity. Since the splanchnic nerve 320 feeds to the celiac ganglia 112, as described in relation to the vagus nerve-related pathways above, the indirect stimulation of the SPgF 344 via the various pathways illustrated and described increases platelet priming in the spleen 310, resulting in more unprimed platelets 340a being converted to primed platelets 340b. As with the pathways via the vagus nerve 110, stimulation using a low mid-range pulse at a low frequency on the Arnold's nerve, and/or a low mid-range pulse at a high frequency on the ATN for a short duration may lead to a noticeable increase in primed platelets, which, for example, could be assessed by a decrease in PT.

Returning to FIG. 3A, given that platelets with higher baseline $Ca^{2+}$ 316 are more likely to activate as pCP, and thus increase the overall coagulation potential of the subject; it is evident that any situation in which a higher coagulation potential is desired will benefit from a method which, when applied to a subject, results in a net influx of $Ca^{2+}$ 316 into the platelets 314. Increasing the activity in VEF 304, as stated above, can trigger a cascade of events leading to a net influx of $Ca^{2+}$ 316 into platelets 314 while they are transiting through the spleen 116.

An individual's blood clotting ability may be assessed through diagnostic tools, such as thromboelastography (TEG). TEG evaluates blood clotting ability and identifies potential abnormalities detected during the clot formation process. The TEG results include reaction time (R-Time) quantifying the duration of time for blood to initiate its clotting cascade after addition of a clotting activator, kinetical time (K-Time) quantifying a duration for the clot, from initiation of the clotting cascade, to reach 20 mm of firmness, Alpha-angle quantifying the rate of fibrin cross-linking during coagulation, maximum amplitude (MA) quantifying overall strength of clotting in millimeters, and lysis at thirty minutes (LY30) quantifying resistance of clotted blood to breakdown (e.g., percentage breakdown a half hour after the time of MA).

TEG deficiencies, in some examples, can be indicative of hypofibrinogenemia (e.g., low fibrinogen levels), thrombocytopenia (e.g., low platelet count), or platelet dysfunction. When a patient's TEG analysis results in the identification of one or more deficiencies, transfusion therapy is often recommended (e.g., fresh frozen plasma, platelet transfusion, and/or cryoprecipitate transfusion).

There are many situations in which a higher coagulation potential is desired. These situations include both chronic (ongoing) circumstances as well as acute scenarios. As identified above, for example, people with conditions leading to a lower than normal and/or lower than desired coagulation potential, as with those suffering from hemophilia or von Willebrand Disease, would benefit from a higher coagulation potential. In another example, subjects taking medications to keep platelets from forming clots in locations other than at an injury site (e.g., anticoagulants or "blood thinners") could benefit from a higher coagulation potential, particularly in pre-surgical and surgical circumstances. In general, any patient or person undergoing a medical procedure in which bleeding is reasonably likely, such as going into surgery, would greatly benefit from a transient increase in their coagulation potential. An increase in the coagulation potential would reduce bleeding time, which in many cases, if not all, translates to overall shorter and less riskier procedures. In addition, increasing the coagulation potential in a surgical setting would limit blood loss. For example, limiting blood loss can stave off the need for blood transfusion and/or reduce the replacement volume needed when a blood transfusion is required; blood for transfusions is extremely costly and, in some cases, limited or unavailable. In an illustrative example involving maternal delivery, postpartum hemorrhage is one of the leading causes of maternal death worldwide. Further, a large amount of blood is lost during any vaginal delivery, and an even larger amount is lost in a caesarian section (C-section) delivery. There are many other surgical procedures in which the risk for large volume bleeding is high, and patients undergoing any such procedure would benefit from an increase in coagulation potential. Another condition in which limiting bleed volume is highly desired and would be vastly beneficial is in cases of abnormal uterine bleeding (AUB), including heavy menstrual bleeding (HMB), which in turn includes menorrhagia. This/these condition/s affect one in four women of reproductive age. Although fatalities from AUB, including HMB, are rare, in some cases, if left untreated it can lead to cancer predisposition. HMB can lead women to a severe anemic condition which could in turn lead to shortness of breath and increase the risk of cardiac complications. As suggested before, HMB is very common, and although it is estimated that a fourth of the women of reproductive age suffer from it, about a third of reproductive age women actually seek treatment for what they consider to be a heavier than desired menstrual bleeding. Thus, new interventions that can help reduce the amount of blood loss in HMB and in general in AUB are extremely desired and would be welcome by women and doctors alike, even if they are used as adjuvants.

Inflammation

Pro-inflammatory reactions are generally triggered when a potential for bodily damage is present such as, in some examples, an infection and/or when a bleeding injury occurs. Usually, this inflammatory response helps the body to heal. However, in many cases an overreacting inflammatory response occurs, triggering detrimental effects which can lead to organ failure and death. At least part of the inflammatory response is carried out by the spleen and, as such, modulating spleen activity can lead to a change in the inflammatory response. In particular, activating the parasympathetic system leads to an anti-inflammatory response in the spleen, leading to a reduction in circulating pro-inflammatory cytokines. Activation of the splenic nerve (e.g., directly and/or via vagal efferent fiber (VEF) activity) leads to the aforementioned anti-inflammatory response. In one example, a decrease in circulating pro-inflammatory cytokines can be achieved by modulating spleen activity via NTS descending pathways.

In some embodiments, the anti-inflammatory effect is provided via activation of an Anti-inflammatory Pathway 100 (a.k.a. the cholinergic anti-inflammatory pathway), as illustrated in FIG. 1. In particular, the ABVN 102 and/or the ATN 104 may be stimulated which have projections to the NTS 108; these projections elicit cholinergic anti-inflammatory effects via efferent pathways; mostly via the vagus nerve 110. As illustrated, the TCC 106 receives afferent connections from the ATN 104 and projects to the NTS 108. Modulation of the NTS 108 affects activity, via the vagus nerve 110, in efferent pathways through the celiac ganglion 112 and parasympathetic ganglion 114, which in turn modulates activity in the spleen 116, lungs 118, gut 120, and/or heart 122 such that an anti-inflammatory response is elicited. Systemic anti-inflammatory effects occur when the vagus nerve 110 indirectly mediates spleen 116 function, thereby reducing the amount of circulating pro-inflammatory cytokines. In addition, a local anti-inflammatory effect occurs at organs reached by the efferent pathways; for example, at the lungs 118, gut 120, and heart 122.

Hypovolemia

When blood circulation decreases to levels at which tissue perfusion can no longer provide proper oxygenation, organs proceed to malfunction up to a point where they begin to fail. Organ failure can lead to permanent damage and even to death. This is particularly true when the organ lacking proper oxygenation is the brain. The brain consumes a large percentage of the circulating oxygen in the body, especially when a person is at rest, thus making it highly vulnerable to low perfusion scenarios. There are brain regions (e.g., brain nuclei or brain areas) which modulate blood pressure as well as blood flow. Activation of such areas of the brain leads to higher blood flow. For example, activation of the Rostral Ventrolateral Medulla (RVLM) has been shown to have a pressor response (illustrated in FIG. 2A), which is one that leads to an increase in blood pressure, perfusion, and flow.

Figures 2A, 2B:
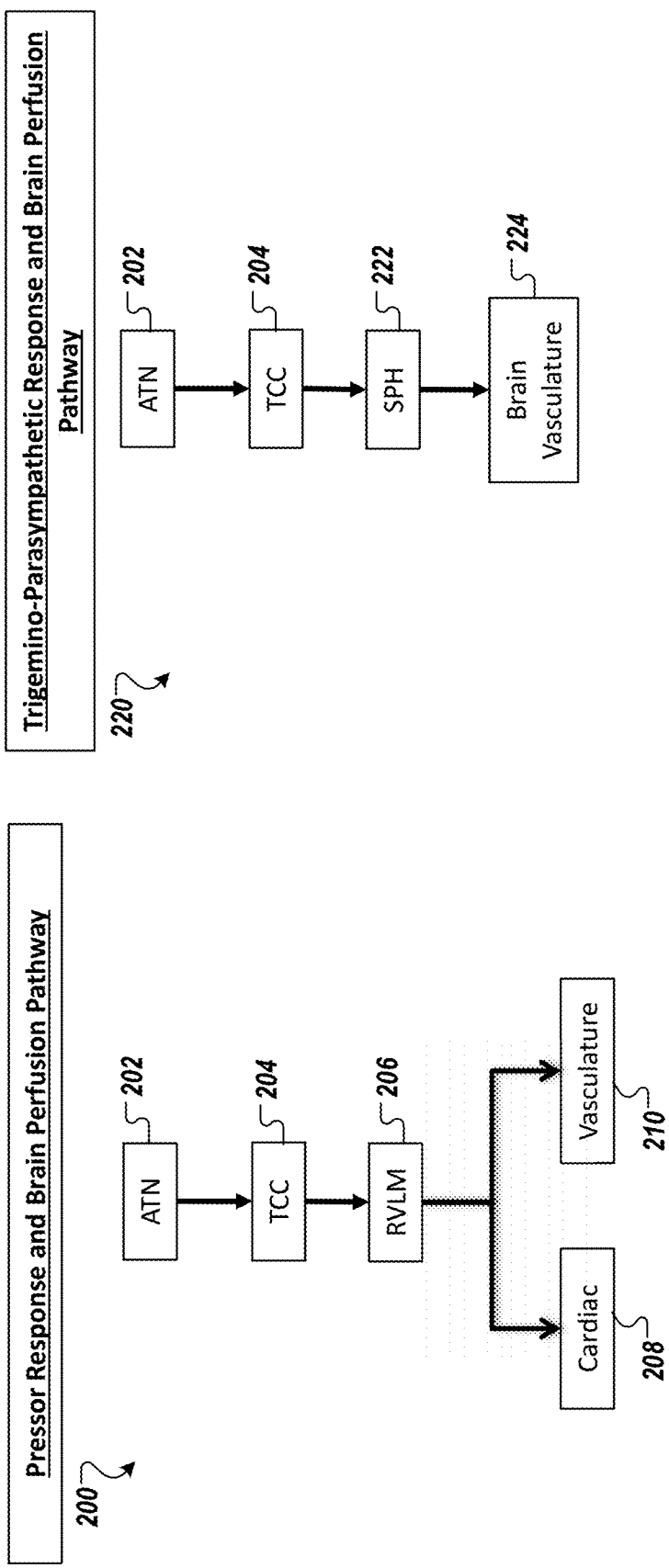
FIG. 2A is a block diagram of an example pressure response and brain perfusion pathway.
FIG. 2B is a block diagram of an example trigemino-parasympathetic response and brain perfusion pathway.

Turning to FIG. 2A, as illustrated in an example pressor response and brain profusion pathway 200, the RVLM 206 receives connections from several nuclei including the trigemino-cervical complex (TCC) 204 which in turn receives afferent connections from trigeminal branches. As illustrated, the TCC 204 receives afferent connections from the Auriculotemporal nerve (ATN) 202. The RVLM 206, in turn, modulates cardiac systems 208 (e.g., blood pressure) as well as vascular systems 210 (e.g., blood flow).

Besides the RVLM 206, activation of the trigemino-parasympathetic pathway 220 (illustrated in FIG. 2B) has been shown to vasodilate brain vasculature 224 at least in part by the release of ACh onto this vasculature 224 by sphenopalatine originating fibers (SPH) 222. The sphenopalatine nucleus (sphenopalatine ganglion) 222 also receives afferent fibers from trigeminal branches, in particular from the mandibular branch of the trigeminal nerve (V3) from which the ATN is part of.

Managing Bleeding

Figure 5:
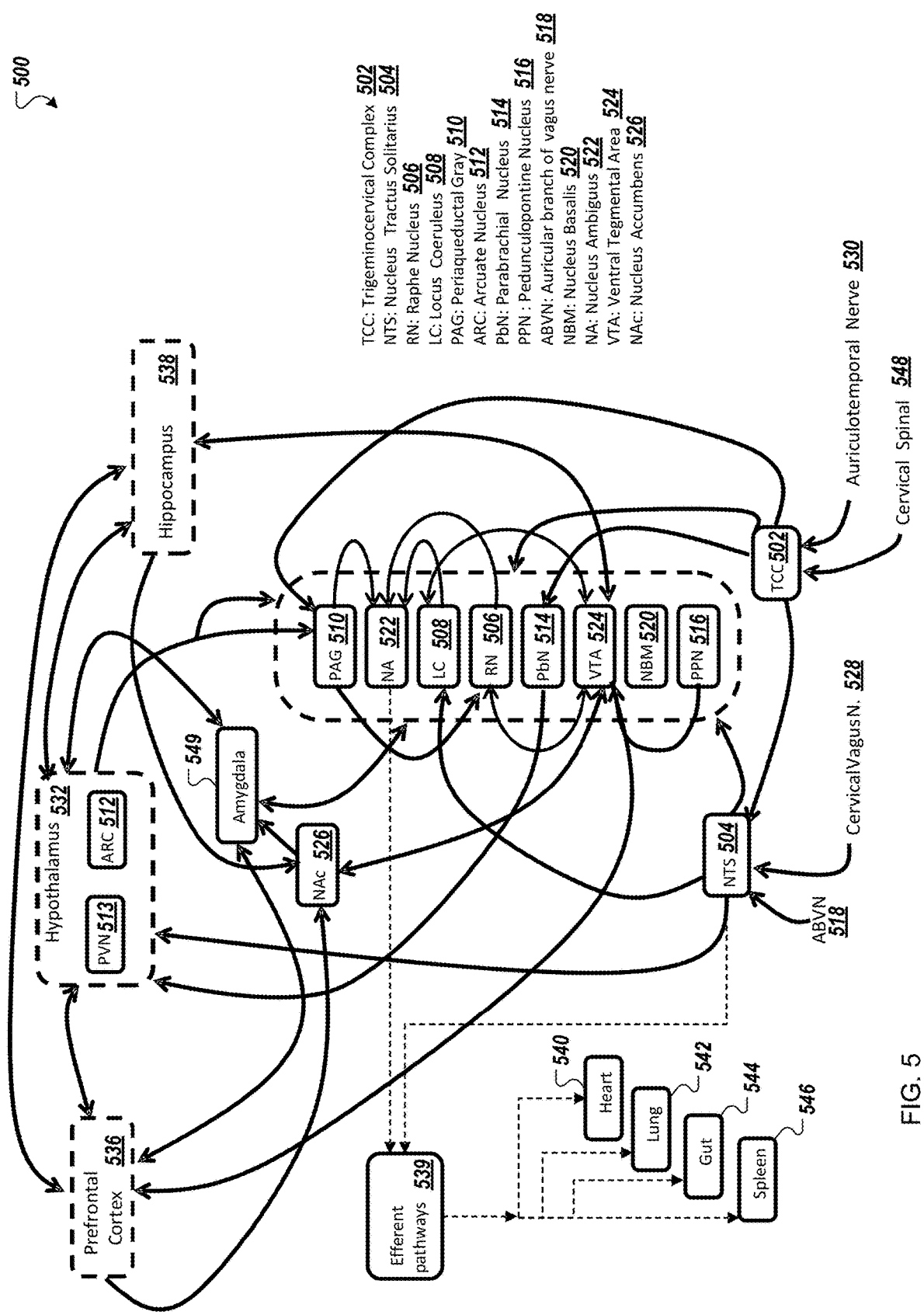
FIG. 5 is a block diagram identifying neural structures and pathways.

Activity in the VEF can be triggered by either directly activating the nerve fibers or by activating areas with direct and/or indirect connections to the nerve fibers. Turning to FIG. 5, for example, a functional diagram of neural structures and pathways 500 illustrates that activity in medullary structures such as in the Nucleus Tractus Soltari (NTS) 504, and the Nucleus Ambiguus (NA) 522 can trigger VEF activity via the efferent pathways 539. Amongst others, the NA 522 receives projections from the Periaqueductal Grey Area (PAG) 510. NTS 504 receives afferent connections from the TCC 502 as well as from ascending vagal branches. In turn, the TCC 502 receives afferent projections from trigeminal and cervical branches and projects to the PAG 510 and the RVLM. Activity in RVLM neurons can trigger the aforementioned pressor response, illustrated in FIG. 2A. Interestingly, not all activity in the TCC 502 leads to the trigemino-parasympathetic response that arises from sphenopalatine activity; studies suggest that it is the activation of the masseteric branch of the trigeminal nerve (MBTN) that leads to this response. One way to activate the MBTN branch is via the Auriculotemporal nerve (ATN) 202.

Activating the VEF can be achieved by stimulation via an invasive approach and/or via a non-invasive approach at various sites. Some invasive examples include using an implantable pulse generator (IPG) to stimulate cervical vagal fiber and/or utilizing needle electrodes to percutaneously stimulate vagal fibers as for example the ABVN and/or trigeminal fibers. A non-invasive approach may transcutaneously stimulate fibers of the ABVN as well as vagal cervical fibers; in addition, trigeminal fibers such as those corresponding to the maxillary, ophthalmic, and/or the mandibular trigeminal branches. In some examples, VEF activation can be accomplished by electrical, mechanical (e.g., ultrasound, pressure, massage, etc.), and/or light (e.g., laser and/or high intensity light) stimulation. Additionally, activation of the nAChRα7 on the platelets can be attained by chemical means such as local or systemic administration of a nAChRα7 agonist such as nicotine. A nAChRα7 agonist can be injected or applied non-invasively as for example using a transdermal/transcutaneous patch or in some cases by a specially designed oral dose. Furthermore, platelets express other calcium transmembrane channels; thus, one or more of these channels (e.g., the channels identified in Table 1 above) can be activated in order to increase the platelet intracellular baseline $Ca^{2+}$. For example, these channels can be activated chemically by their respective agonist and/or partial agonist in a similar fashion as described above for the nAChRα7. Channels through which $Ca^{2+}$ exits the platelet could be temporarily or partially blocked with, for example, partial antagonists to prevent or slow down $Ca^{2+}$ from flowing out of the platelet into the extracellular space and allowing it to be transported into internal storages within the platelet. In some or all cases, it would be desired and/or required that any such intervention increasing intracellular $Ca^{2+}$ be done such that platelets are not activated as $Ca^{2+}$ enters the intracellular space.

Under normal circumstances, high concentrations of cytosolic $Ca^{2+}$ can trigger platelet activation. In order to prevent thrombus formations at locations other than at the site of injury, platelet activation should be mainly localized to the injury site. Accordingly, it is preferred that $[Ca^{2+}]_{cyt}$ is kept relatively low until the time when the platelets need to be activated. However, when activated, a high $[Ca^{2+}]_{cyt}$ is needed for the platelet to activate as a pCP. One way of doing this is to allow the $Ca^{2+}$ to be kept in internal platelet storages to be released into the cytosolic space upon platelet activation.

A pressor response, as illustrated in FIG. 2A, can be achieved by invasive and/or non-invasive stimulation at various sites. In some examples, a pressor response can be triggered by electrical, mechanical (e.g., ultrasound, pressure, massage, etc.), and/or light (e.g., laser and/or high intensity light) stimulation.

A trigemino-parasympathetic response, as illustrated in FIG. 2B, can be achieved by invasive and/or non-invasive stimulation at various sites. In some examples, a trigemino-parasympathetic response can be triggered via electrical, mechanical (e.g., ultrasound, pressure, massage, etc.), and/or light (e.g., laser and/or high intensity light) stimulation.

TABLE 2

Example Stimulation Durations
Stimulation Duration Table

| | |
|---|---|
| Very Short Duration | 1-5 min. |
| Short Duration | 5-15 min. |
| Medium Duration | 15-60 min. |
| Long Duration | 1-5 hrs. |
| Very Long Duration | 5-24+ hrs. |

TABLE 3

Example Treatment Periods
Treatment Period Table

| | |
|---|---|
| Brief Period | <5 min. |
| Very Short Period | 5-15 min. |
| Short Period | 15-60 min. |
| Medium Period | 1-5 hrs. |
| Long Period | 5-24 hrs. |
| Very Long Period | 1-7 days |
| Extremely Long Period | 7-30+ Days |

Stimulations for generating one or more of the responses described herein to achieve a transient effect in a preventive/prophylactic scenario, such as generating a pressor response, a trigemino-parasympathetic response, and/or an increase in CPot, in some embodiments, is started a short period of time before the event and applied for a very short duration. For example, in the circumstance of an upcoming trauma, such as an emergency surgery, stimulation may begin only a brief period prior to the trauma (e.g., surgical procedure). In another embodiment stimulation is started a medium or long period of time before the event and can be intermittently and repeatedly applied for a very short or short duration. In illustration, in the event of avoiding hemorrhaging during delivery, a pregnant woman may be provided short durations of intermittent or periodic stimulation throughout the uncertain duration of labor. In another illustration, in the event of medical intervention, such as C-section, for example, the prophylactic treatment can stem unnecessary blood loss.

In some embodiments, repeated intermittent stimulations are applied at predetermined duty cycles. For example, a 30% ON/70% OFF duty cycle could be implemented as applying stimulation for three minutes ("ON") out of every ten minutes. In other non-limiting examples, the duty cycle may be configured to be a 30% ON/70% OFF duty cycle (e.g., 3 min ON/7 min OFF or 6 min ON/14 min OFF, etc.), a 50% ON/50% OFF duty cycle (e.g., 1 min ON/1 min OFF, or 5 min ON/5 min OFF, etc.), an 80% ON/20% OFF duty cycle (e.g., 4 min ON/1 min OFF, etc.) or a 97% ON/3% OFF duty cycle (e.g., 5 min ON 10 seconds OFF, etc.) In yet another illustrative example, a platelet donor may start stimulation seven or more days prior to her/him donating platelets, such that the donated platelets are primed platelets. The total amount of needed platelets to be donated may be significantly reduced when the donated platelets are primed platelets. In this case, for example, stimulation may be administered daily for repetitive short periods of time. In further examples, stimulation may be applied for a short duration, for a medium duration, for long duration, or for a very long duration. In another embodiment, stimulation can be started a long period of time before the event or a very long period of time before the event.

In preparation for a potentially dangerous scenario, for example a military operation, military personnel can start stimulation approximately three weeks or more before the actual operation while they train for it and stop stimulation once the operation finishes. In this case, stimulation could be applied daily for a single or multiple very short, short, or medium periods of time.

Stimulations for generating one or more of the responses described herein, such as generating a pressor response, a trigemino-parasympathetic response, and/or an increase in CPot, in some embodiments, are applied periodically, e.g., in repetitive patterns. In some examples, the stimulations may be applied 1 time every 10 minutes, 1 time every 30 minutes, 1 time every hour, 4 times per day, or once per day. The duration may vary based in part on frequency of the periodic stimulation. In some examples, stimulations may be applied once every ten minutes for a short duration, once every hour for a medium duration, or once per day for a long duration. In another embodiment, in order to reduce total blood loss and/or total monthly bleeding days, a female suffering from HMB/menorrhagia, including those with any coagulation disorder, could, for example, start stimulation a few days before starting her menstrual period and continue stimulation until the end of menstruation. In such a case, stimulation could be applied, for example, once daily for a very short or a short period of time. Other schedules are possible based on, in some examples, convenience, comfort, strength of desired effect, and/or potential severity of the outcome (e.g., likelihood of harm to the patient due to lack of/inadequate prophylactic treatment).

In circumstances in which the goal is to treat a chronic condition, in an illustrative embodiment, stimulation generating one or more of the responses described herein, such as generating an increase in CPot, a pressor response, and/or a trigemino-parasympathetic response, may be delivered in repetitive patterns for as long as needed. For example, stimulation can be applied daily or several times each day with a duration (e.g., very short, short, medium, long, or very long) based in part on relative frequency of treatment. In another example, an initial level of coagulation potential may be generated (e.g., "kick-started") in a person by applying stimulation at least daily for a first period of time, followed by less frequent treatments or a tapering off of frequency of treatments to maintain the coagulation potential at a desired level. For example, stimulation may be applied daily for a first period of time (e.g., between 5 and 10 days), followed by less frequent treatments (e.g., once or in some cases twice a week) to maintain the coagulation potential within a desired range. In another example, stimulation may be applied daily for a first period of time, then three times per week for a second period of time, then twice per week for a third period of time, followed by once per week to maintain the desired level of coagulation potential. In a further example, a therapy schedule involving initial stimulation applications per week (e.g., 7) for the first week followed by a different number of stimulation applications per week (e.g., 5) on the second week, etc. can be customized in order for a particular individual to maintain a desired coagulation potential. Additionally, durations of treatment may be modified per time period in any of the aforementioned examples.

Figure 7A:
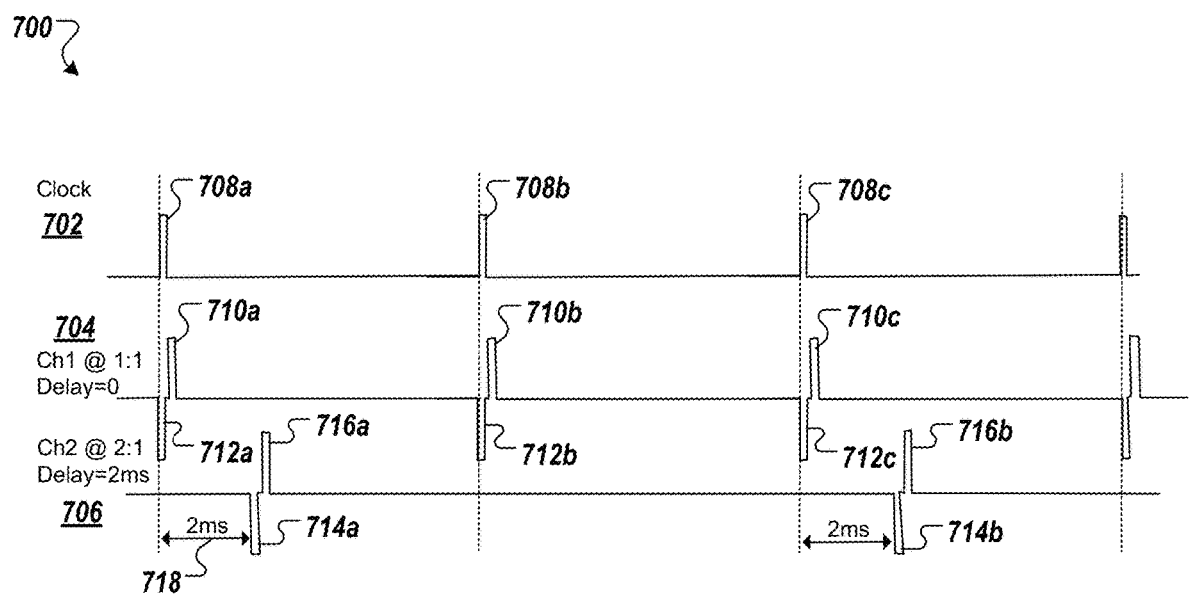
FIG. 7A and FIG. 7B illustrate timing diagrams of example processes for triggering stimulation.

In general, stimulation duration is defined by the time the device is actively delivering a stimulation therapy rather than by the actual time in which the stimulation is being generated. For example, the device can be activated (e.g., powered on) for one hour while stimulation is being applied at a particular frequency and with a particular pulse duration (e.g., pulse width), for example as illustrated in FIG. 7A and/or FIG. 7B. Further, the stimulation pulses can be applied following a particular duty cycle, for example 5 minutes delivering and 20 seconds not delivering, or 30 seconds delivering and 30 seconds not delivering, etc. Additional example duty cycles are illustrated in the timing diagrams of FIG. 7A and FIG. 7B.

Figure 6A:
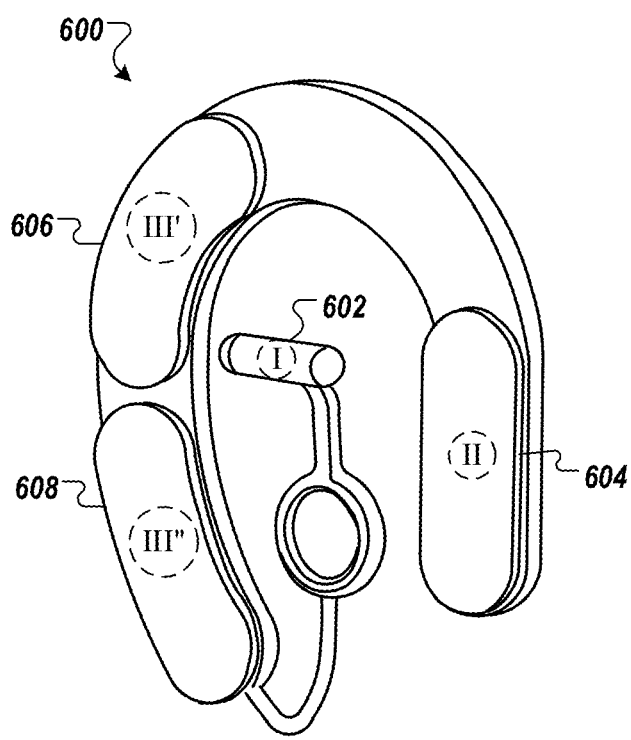
FIG. 6A and FIG. 6B are diagrams representing of an electrode configuration and an equivalent circuit for providing therapy according to a first example.
Figure 6B:
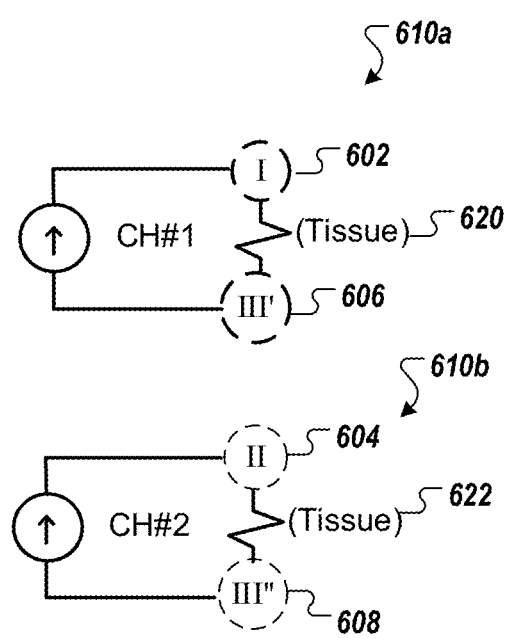
Figure 6C:
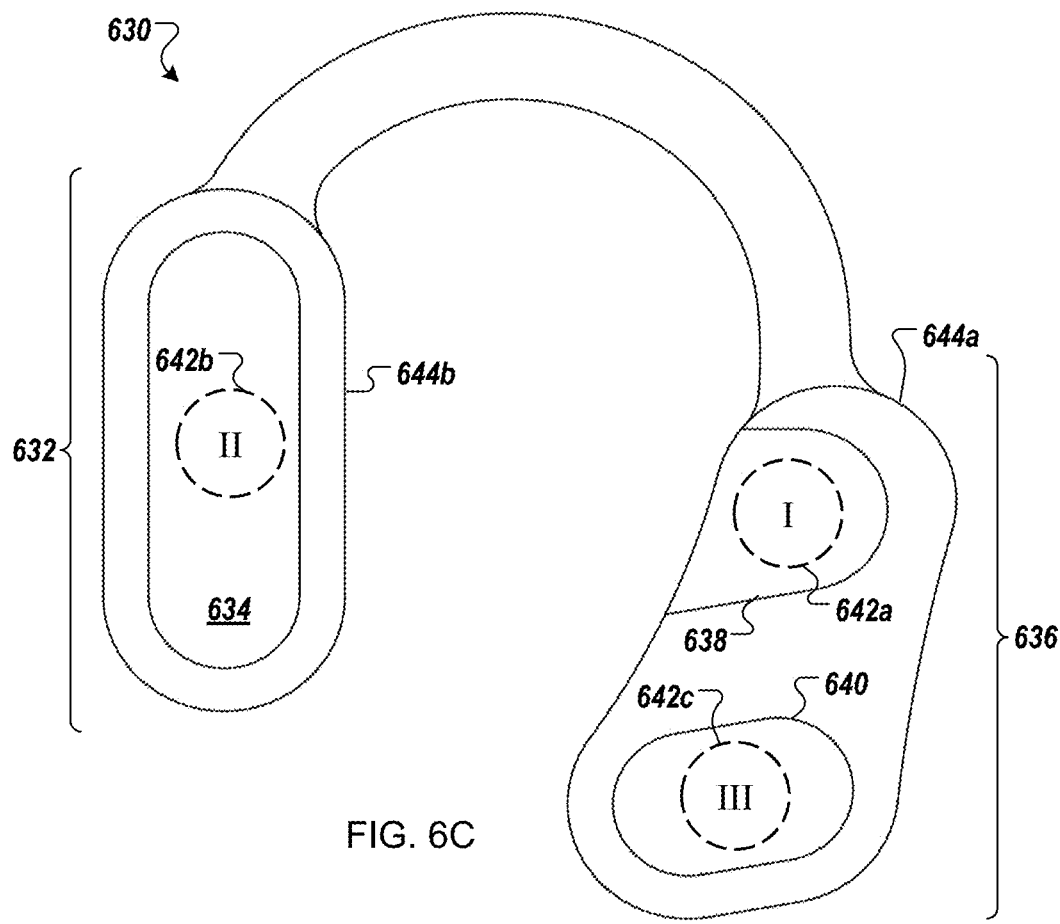
FIG. 6C and FIG. 6D are diagrams representing of an electrode configuration and an equivalent circuit for providing therapy according to a second example.

Turning to FIG. 6C, a WANS apparatus 630 includes a forward portion 632 including a conductive adhesive region 634 with a surrounding non-conductive adhesive region 644b and a rear portion 636 including conductive adhesive regions 638 and 640 with a surrounding non-conductive adhesive region 644a. The non-conductive adhesive regions 644a, 644b, for example, may provide extra adhesion for a robust skin/conductive adhesive contact. The conductive adhesive region 634 of the forward portion 632, for example, corresponds to a second electrode (II) 642b. Turning to the rear portion 636, the conductive adhesive region 638 corresponds to a first electrode (I) 642a, and the conductive adhesive region 640 corresponds to a third electrode (III) 642c. In some embodiments, the electrodes 642a-c and their corresponding conductive adhesive regions 634, 638, and 640 each have a similar shape and area. In other embodiments, the shape and/or surface area of each of the electrodes 642a-c and/or their corresponding conductive adhesive regions 634, 638, and 640 may differ, for example based on the underlying target nerve structures and/or the shape of the anatomy on which the electrodes 642a-c and their corresponding conductive adhesive regions 634, 638, and 640 are configured to be positioned.

Figure 10A:
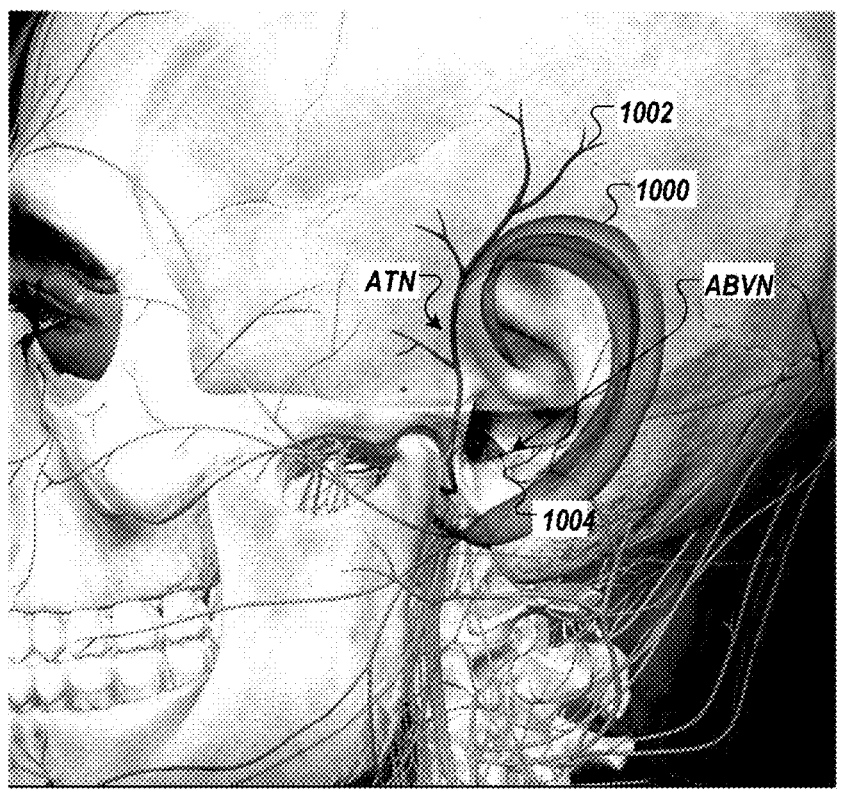
FIG. 10A through FIG. 10D, FIG. 11, and FIG. 12 illustrate example target nerve regions for directing therapy using a wearable auricular neurostimulator (WANS) apparatus.
Figure 10B:
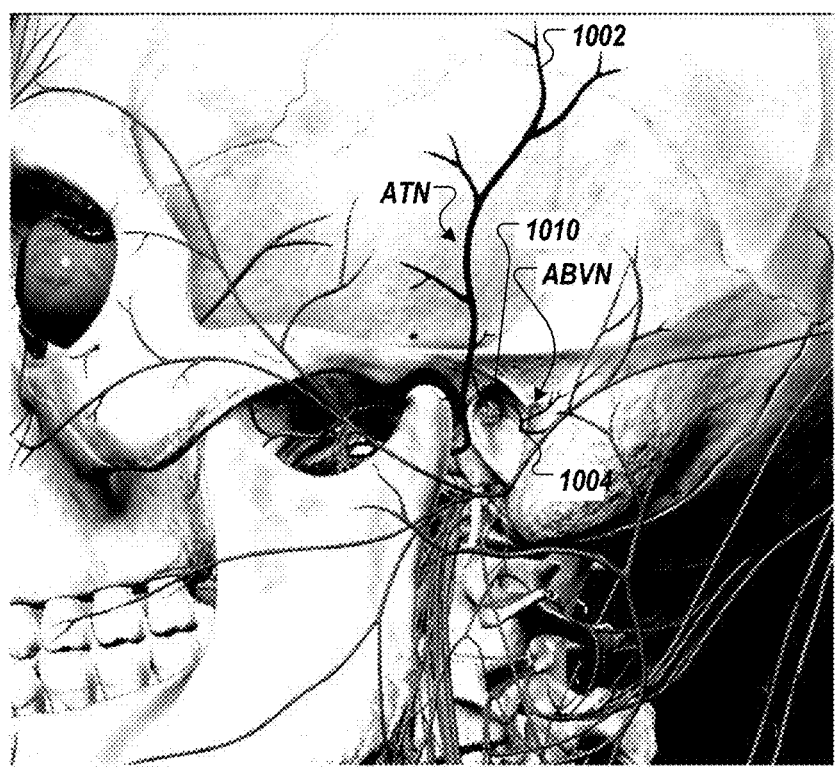

The conductive adhesive region 634, in some implementations, is configured to contact skin of a wearer in a region of nerve structures of the auriculotemporal nerve (ATN) and/or nerve structures connected to the ATN, such that delivery of therapeutic stimulation via the conductive adhesive region 634 modulates ATN activity. Turning to FIG. 10A and FIG. 10B, for example, ATN 1002 is illustrated in relation to an ear 1000 of a person (FIG. 10A), running generally in front of the ear 1000, as well as in relation, skeletally (FIG. 10B), to an ear canal 1010. In an illustrative example, an electrode in electrical communication with the conductive adhesive region 634 may be positioned in proximity to the temporomandibular joint.

Figure 10C:
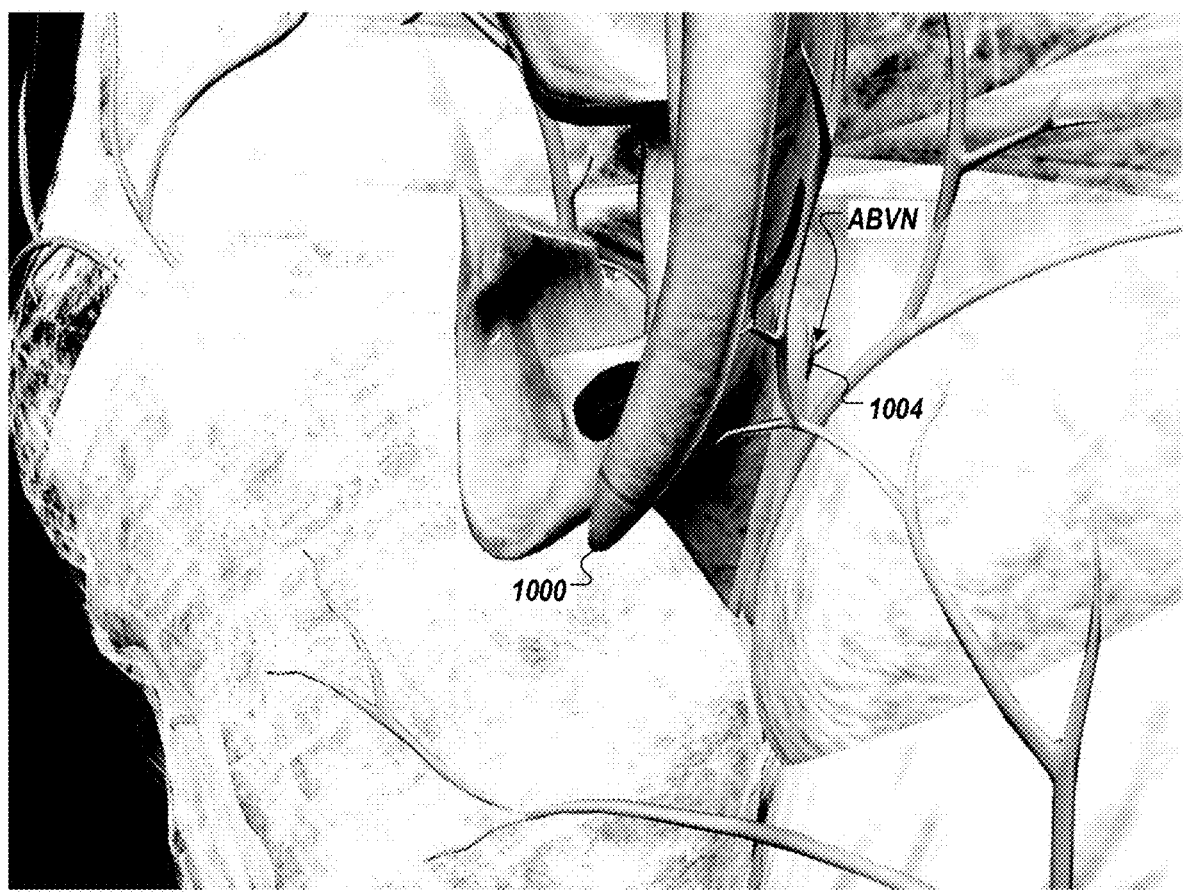
Figure 10D:
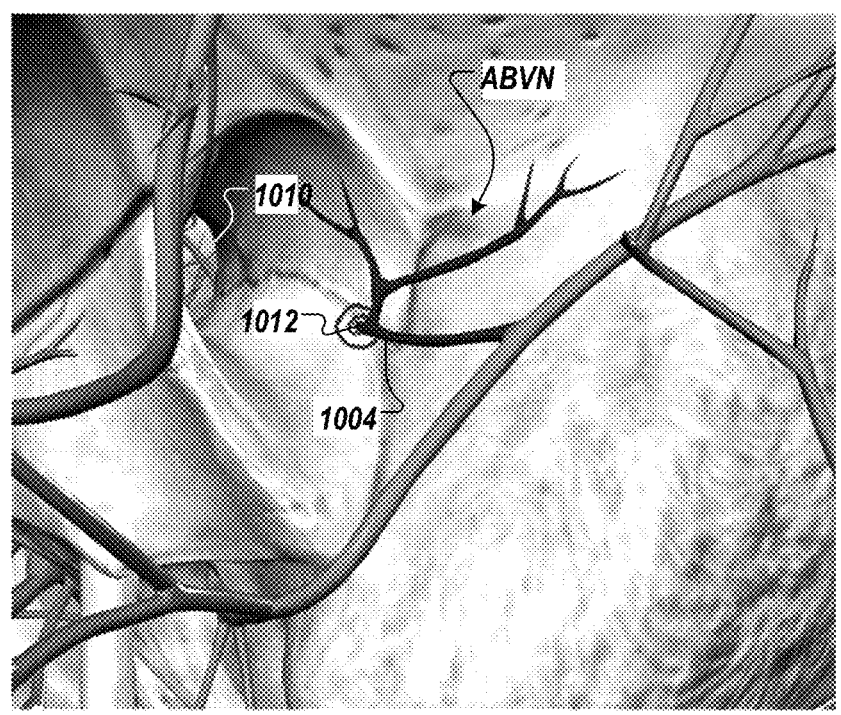
Figure 11:
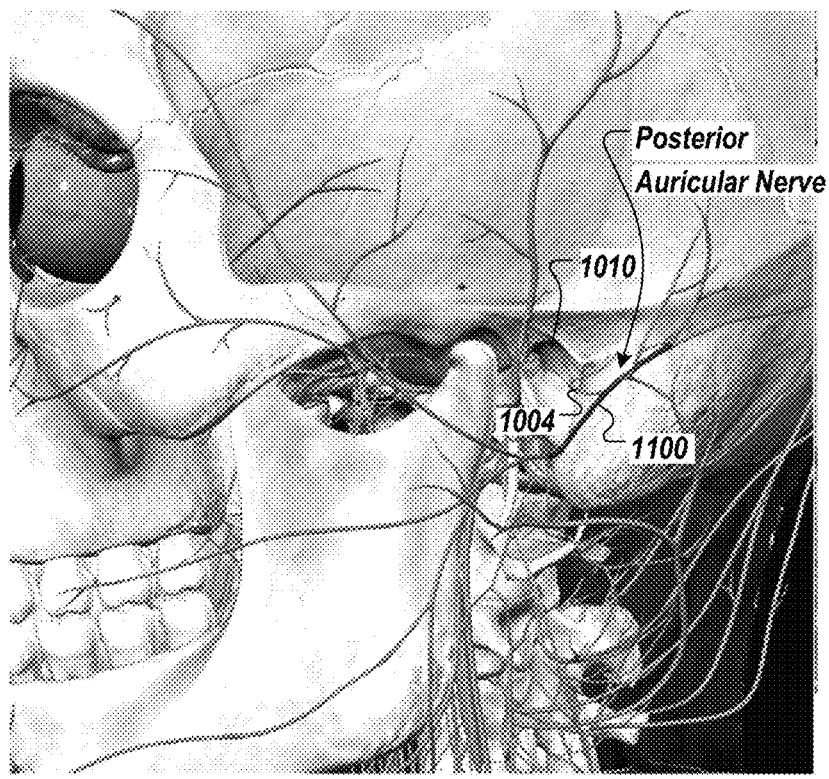

In some embodiments, the conductive adhesive region 638 is configured to contact skin of a wearer in a region of nerve structures of the auricular branch of the vagus nerve (ABVN) and/or nerve structure connected to the ABVN such that delivery of therapeutic stimulations via the conductive adhesive region 638 modulates ABVN activity. As shown in FIG. 10A through FIG. 10D for example, ABVN 1004 is illustrated as it surfaces (FIG. 10D) through the mastoid canaliculus (MsC) 1012 (a.k.a., Arnold's canal) and in relation to the ear 1000 (FIG. 10A), in relation to the ear canal 1010 (FIG. 10B) and in relation to the back of the ear (FIG. 10C). Turning to FIG. 11, posterior auricular nerve 1100 meets a branch of the ABVN, providing another target for ABVN stimulation. In an illustrative example, an electrode in electrical communication with the conductive adhesive region 638 may be positioned in proximity to the MsC.

The conductive adhesive region 640, in some embodiments, is configured to contact skin of the patient as a return electrode, thereby forming an electrical circuit across the tissue with the electrodes corresponding to each of the forward conductive adhesive region 634 and the rear conductive adhesive region 636. Although illustrated as a single return electrode (e.g., third electrode 642c) provided for both electrodes 642a and 642b corresponding to adhesive region 638 and adhesive region 634, in other embodiments, a different, separate return electrode may be provided for each electrode 642a, 642b. In further embodiments, three or more return electrode paths may be provided for the two positive electrodes. Other combinations are possible.

Figure 6D:
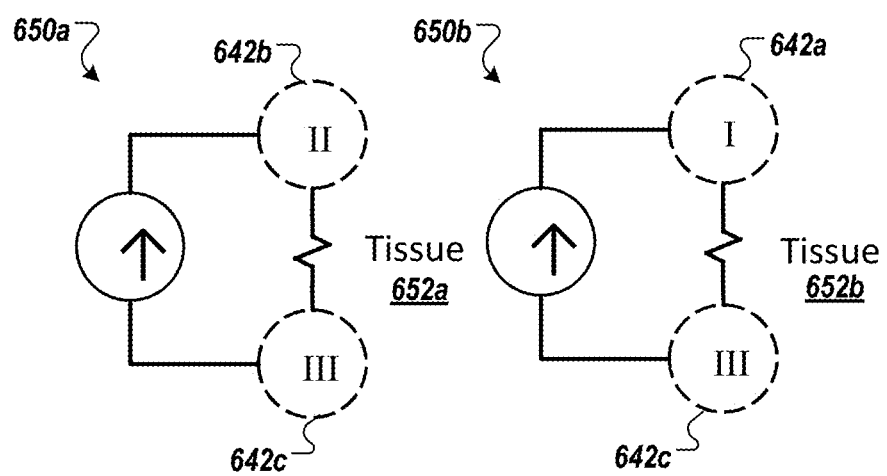
Figure 6E:
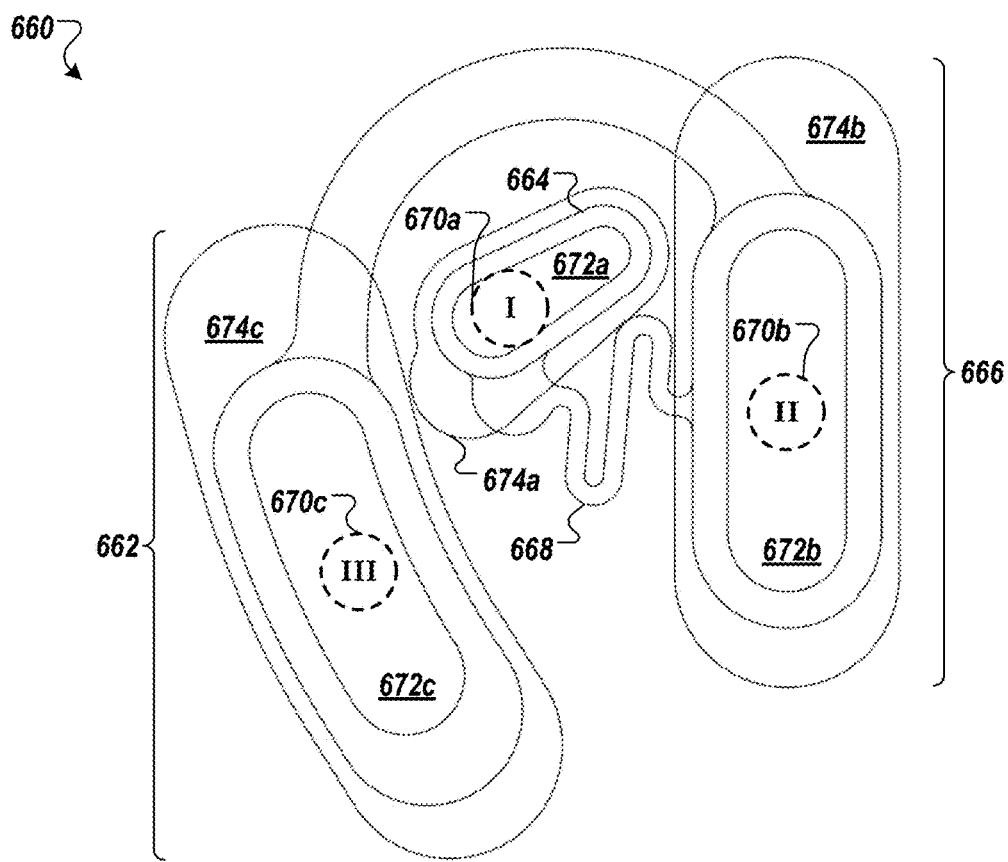
FIG. 6E and FIG. 6F are diagrams representing of an electrode configuration and an equivalent circuit for providing therapy according to a third example.

Turning to FIG. 6E, a wearable auricular neurostimulator (WANS) 660 includes a forward portion 666, a rear portion 662, and an on-ear portion 664, each portion including at least one electrode (e.g., electrodes 670a, 670b, and 670c). When donned by a wearer, the WANS 660 may be wrapped around the ear such that forward portion 666 is disposed in front of the ear and the rear portion 662 is disposed behind the ear. The on-ear portion 664, connected to the forward portion 666 by a flexible connector 668, may be frictionally and/or adhesively retained in a cymba region of the ear.

To increase engagement of the WANS 660 with tissue of the wearer and/or to enhance electrical communication between the tissue and the electrodes 670a-c, in some embodiments, each electrode 670a-c is disposed in electrical communication with a corresponding conductive adhesive region 672a-c. The conductive adhesive regions 672a-c may create an electrical communication path from an electrode positioned in or on the WANS 660 to skin of the wearer. To protect and maintain cleanliness of the conductive adhesive regions 672a-c prior to wearing, in some implementations, the WANS 660 is provided with one or more liners, such as the liners 674a-c. To provide robust skin contact, in some implementations, the conductive adhesive regions 672a-c are surrounded by one or more non-conductive adhesive regions. In some embodiments, the electrodes 670a-c and their corresponding conductive adhesive regions 672a-c have a similar shape and area. In other embodiments, the size and/or shape varies electrode-to-electrode and/or adhesive region-to-adhesive region, for example based on the targeted underlying nerve structures and/or the topography of the anatomy on which the particular electrode and adhesive region are configured to be positioned.

Figure 12:
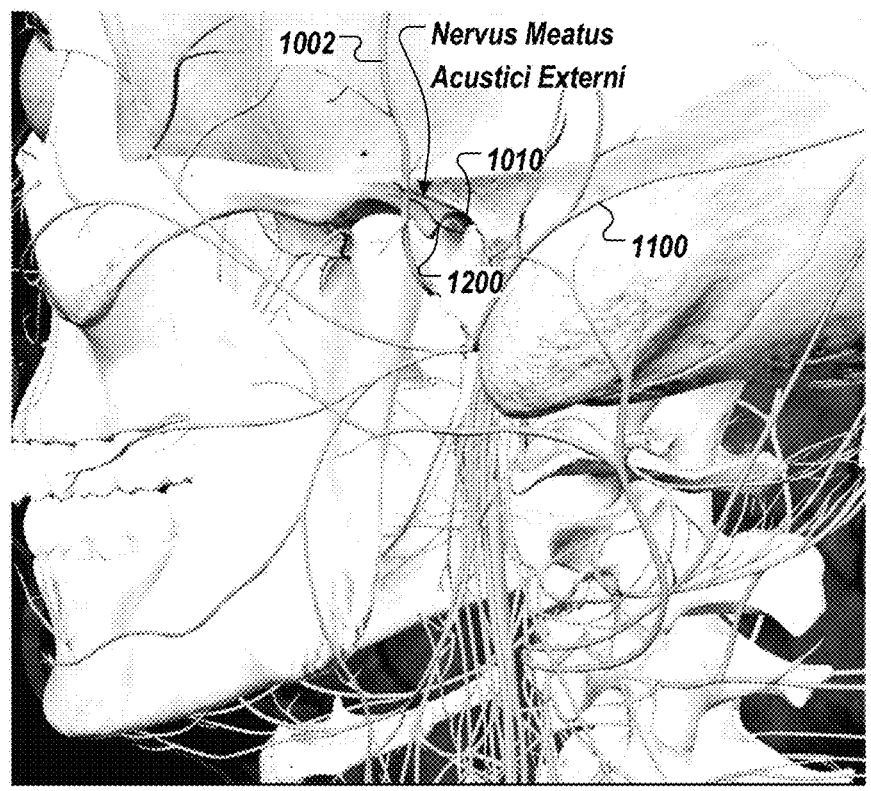

The conductive adhesive region 672a may be provided to create an electrical communication path from the electrode 670a positioned on the on-ear portion 664 of the WANS 660 to skin of the wearer in an anterior part of the ear canal. Turning to FIG. 12, such an electrode, for example, may be positioned to stimulate the nervus meatus acustici externi branch 1200 of the ATN 1002. In other embodiments, in order to stimulate branches of the ABVN, the conductive adhesive region 672a is positioned on the concha, on the cymba concha, or on the tragus.

Turning to FIG. 7A, a drawing of a timing diagram 700 illustrates the triggering of multiple channels 704, 706 using a master clock 702 according to an example. In an exemplary embodiment, the clock 702 triggers pulses 708 at a predetermined clock frequency. In an example, a first channel 704 can be configured to trigger a stimulation pattern 710-712 and a second channel 706 can be configured to trigger a second stimulation pattern 714-716.

As illustrated, each cycle of the stimulation pattern 710-712 of the first channel 704 is configured to be triggered by a corresponding pulse 708 of the master clock 702; i.e., at a 1-to-1 ratio. In an example, each stimulation 712 (e.g., 712a, 712b, etc.) is configured to be triggered following a specific time interval after the pulse 708 (e.g., 708*a*, 708*b*, etc.) in the corresponding stimulation 710 (e.g., 710*a*, 710*b*, etc.) ends.

As illustrated, each cycle of the stimulation pattern stimulation 714-716 is configured to be triggered by every other pulse 708 of the master clock 702; i.e., at a 2-to-1 ratio with the master clock 702. However, the triggering of each stimulation 714 (e.g., 714*a*, 714*b*, etc.) is configured to occur after a specific time delay after the corresponding master clock pulse 708 (e.g., 708*a*, 708*b*, etc.). In some embodiments, each stimulation 714 (e.g., 714*a*, 714*b*, etc.) is configured to be triggered following a specific time interval after the corresponding pulse in stimulation 712 (e.g., 712*a*, 712*b*, etc.) ends. In an example, each stimulation 714 is offset from each corresponding stimulation 712 by a synchronous delay 718. As illustrated, the synchronous delay 718 is 2 ms. However, in certain embodiments, the synchronous delay 718 can be as little as zero, causing both channels 704, 706 to trigger simultaneously depending on the master clock ratio for each channel 704, 706. Further, the synchronous delay 718 can be as much as the master clock 702 period less the combined duration of each cycle of stimulation 710-712 and each cycle of stimulation 714-718 plus the time interval between the cycles 710-712, 714-718. This delay, further to the illustrated example, may amount to up to about 10 ms.

In some implementations, the channels 704, 706 are synchronized using a master clock counter and a register per channel 704, 706. By setting each register to a number of master clock pulses 708 to trigger the respective channel 704, 706, each channel 704, 706 can be configured to be triggered when the channel register value equals the master clock pulses 708. Further to the example, the counter for each channel 704, 706 can be reset after the channel 704, 706 is triggered. In illustration, using a 6-bit counter and a 6-bit register, the trigger frequency can be as high as the master clock frequency (1:1) and as low as 1/64 of the clock frequency (64:1).

Figure 7B:
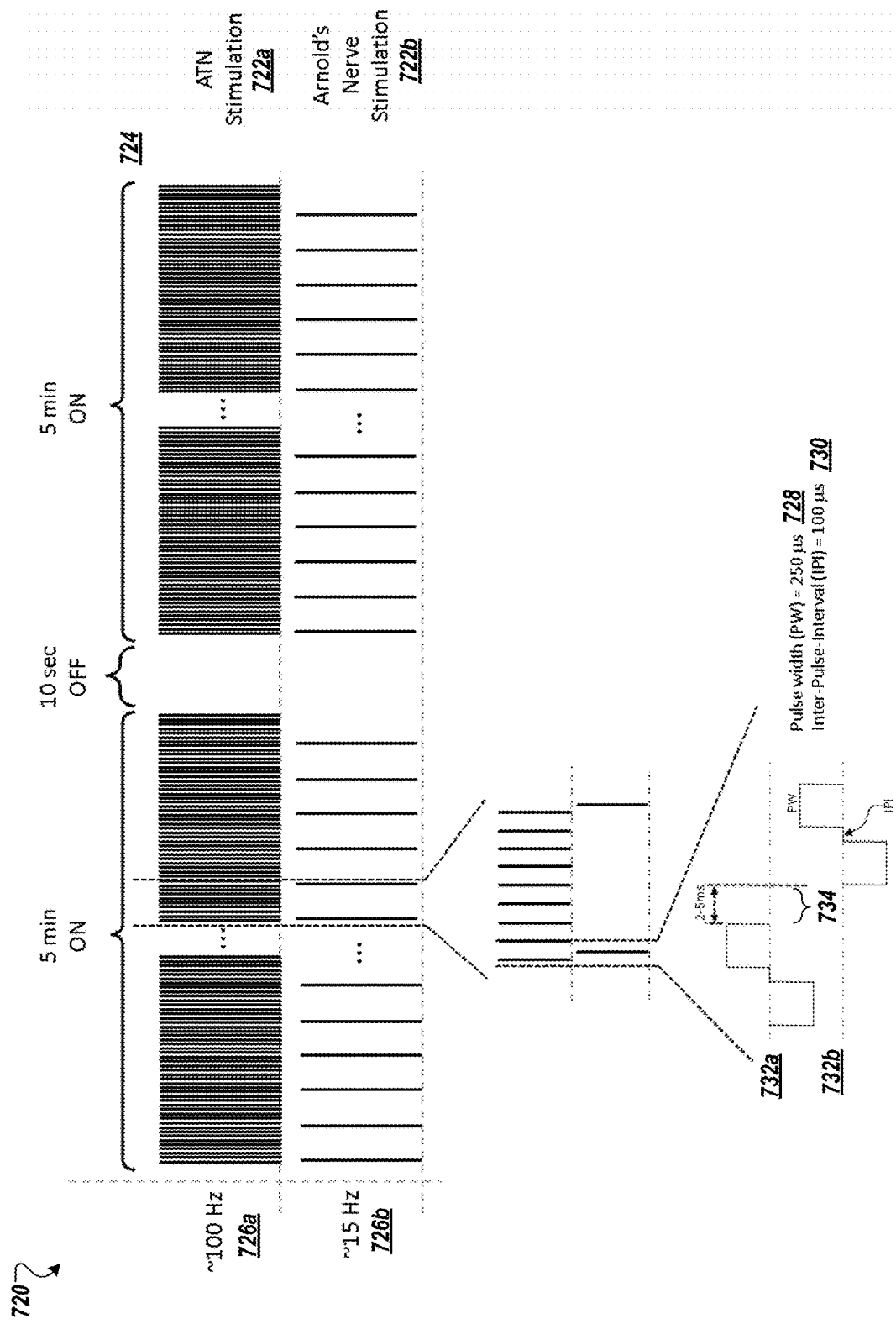

Turning to FIG. 7B, a timing diagram 720 illustrates the triggering of multiple stimulation patterns 722 (an ATN stimulation pattern 722*a* and an Arnold's Nerve stimulation pattern 722*b*) for concurrent stimulation using a neuromodulation device, such as various devices described herein. The stimulation triggering, in some embodiments, is performed using a single master clock, such as the master clock 702 of FIG. 7A. The stimulation patterns 722*a*, 722*b*, for example, may be configured to deliver a platelet enrichment therapy via the platelet priming pathway 330, as described in relation to FIG. 3A and FIG. 3B.

As illustrated, a duty cycle 724 for each of the stimulation patterns 722*a*, 722*b* is configured for five minutes of active stimulation followed by ten seconds without stimulation (e.g., a "short duration" according to Table 2, above). In other examples, the stimulation patterns 722*a*, 722*b* may be configured for four minutes of active stimulation followed by ten seconds without stimulation, four minutes of active stimulation followed by twenty seconds without stimulation, and/or four minutes of active stimulation followed by one minute without stimulation. In other embodiments, the duty cycles 722*a*, 722*b* may include different stimulation durations (e.g., a medium duration, long duration, or very long duration). While in some cases, a high duty cycle (e.g., 90% ON time) may be needed in order to exert the desired therapeutic effect, in other cases a lower duty cycle (e.g., 50% ON or even 30% ON) may be sufficient; this may depend on the specific condition of the particular user. However, given that a high enough duty cycle is selected to be effective, user preferences may be taken into account. For example, lengthier durations of stimulation may cause wearer fatigue (e.g., tedium with the sensation), while lengthier durations of pauses may be more noticeable to the wearer, which may prove to be a welcome break in sensation to some while an irritation to others. Thus, in some implementations the duty cycle is customizable to an extent based on user preferences/tolerances.

Further, the duty cycles of the stimulation patterns 722*a*, 722*b* are aligned such that no stimulations are delivered during the ten second period. Although only 10 minutes of active stimulation are illustrated (e.g., a "very short period" according to Table 3 above), in some embodiments, the duty cycles 722*a*, 722*b* may repeat for a longer period of treatment (e.g., a short period, a medium period, a long period, a very long period, or an extremely long period).

The stimulation pattern 722*a*, configured for stimulating the ATN, is delivered at approximately 100 Hz frequency 726*a* (e.g., a high frequency according to Table 5, below). A very high frequency (e.g., 150-200 Hz or above) may be used in some embodiments. Further, a pulse width 728 (e.g., a low mid-range pulse according to Table 6, below) of each triggered stimulation is 250 microseconds with an inter-pulse interval 730 of 100 microseconds.

The stimulation pattern 722*b*, configured for stimulating the Arnold's Nerve, is delivered at approximately 15 Hz frequency 726*b* (e.g., a low frequency according to Table 5, below). A mid-range frequency (e.g., 30-40 Hz or above) may be used in some embodiments. A stimulation of 5 Hz, for example, may be uncomfortable or irritating to some wearers, while higher frequency stimulations (e.g., a mid-range frequency rather than a low frequency) may be more comfortable to certain wearers. Thus, in some implementations, the stimulation frequency is customizable to an extent (e.g., within a treatment range) based on user preferences/tolerances.

The stimulation pattern 722*b* uses the same pulse width 728 and inter-pulse interval 730 as the ATN stimulation pattern 722*a*. The pulse width 728 and inter-pulse interval 730 may be varied, in particular in consideration with the trade-off between amplitude and pulse width in signaling the activation threshold (e.g., for lower amplitudes, the pulse width widens). Further, the selected pulse width 728 and inter-pulse interval 730 (e.g., the activation threshold) may depend in part on the fiber type and/or diameter of sensory fiber being targeted by the stimulation. Certain devices described herein, for example, are designed to target Aβ fibers at a current level between 1 and 5 mA. Other fibers which could be targeted for treatment include Aα and Aδ fibers, indicated in Table 4 below. Conversely, C fibers, being mostly nociceptive, would not provide as effective a treatment.

TABLE 4

Sensory Fiber Types

| Classification | Diameter | Myelin sheath | Conduction velocity |
|---|---|---|---|
| Aα | 13-20 μm | Yes | 80-120 m/s |
| Aβ | 6-12 μm | Yes | 33-75 m/s |
| Aδ | 1-5 μm | Yes | 3-30 m/s |
| C | 0.2-1.5 μm | No | 0.5-2.0 m/s |

As illustrated, a pulse timing 732*a* of the ATN stimulation pattern 722*a* is offset from a pulse timing 732*b* of the Arnold's Nerve stimulation pattern 722*b* by a gap 734 of about two to five milliseconds. Thus, the ATN stimulation pattern 722*a* is configured to be delivered concurrently with the Arnold's nerve stimulation pattern 722b without simultaneous pulse triggering between the two stimulation patterns 722a, 722b. To achieve the pulse timing, for example, the frequency of the stimulation pattern 722b may be set to 14.28 Hz (e.g., ½ the frequency of the stimulation pattern 722a).

In some embodiments in which stimulation is applied at more than one site (e.g., directed to two or more nerve branches, etc.) the stimulation duration, the frequency, the pulse width, and/or the duty cycle may differ across stimulation sites. In some embodiments, in fact, it is beneficial to use different frequencies at different stimulation sites.

Stimulation delivery may vary based upon the therapy provided by the treatment device. Frequency and/or pulse width parameters, for example, may be adjusted for one or more stimulation sites at which stimulation is being delivered.

In some embodiments, frequency and/or pulse width parameters are adjusted during therapy, for example responsive to feedback received from monitoring the patient. In some examples, feedback may be obtained using one or more sensors or other devices assessing heart rate, heart rate variability, electroencephalogram (EEG), blood pressure, and/or blood oxygen concentration.

In some embodiments, the system utilizes feedback to monitor and/or modify the therapy. The feedback may be obtained from one or more sensors capable of monitoring one or more symptoms being treated by the therapy. For example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.). In some examples, the sensors may monitor one or more of electrodermal activity (e.g., sweating), movement activity (e.g., tremors, physiologic movement), glucose level, neurological activity (e.g., via EEG), muscle activity (e.g., via EMG) and/or cardio-pulmonary activity (e.g., EKG, heart rate, blood pressure (systolic, diastolic, and/or mean)). Imaging techniques such as MRI and fMRI could be used to adjust the therapy in a clinical setting for a given user. In other embodiments, imaging of pupillary changes (e.g., pupillary dilation) using, for example a common cellular phone and/or smart-glass glasses could be used to provide feedback to make therapy adjustments. In some implementations, one or more sensors are integrated into the earpiece and/or concha apparatus. One or more sensors, in some implementations, are integrated into the pulse generator. For example, periodic monitoring may be achieved through prompting the wearer to touch one or more electrodes on the system (e.g., electrodes built into a surface of the pulse generator) or otherwise interact with the pulse generator (e.g., hold the pulse generator extended away from the body to monitor tremors using a motion detector in the pulse generator). In further implementations, one or more sensor outputs may be obtained from external devices, such as a fitness computer, smart watch, or wearable health monitor.

Optical techniques have been used to assess thrombin concentration (see Martínez-Pérez, Paula, et al. "Continuous detection of increasing concentrations of thrombin employing a label-free photonic crystal aptasensor." Micromachines 11.5 (2020): 464.). It is expected that the thrombin concentration would increase following the stimulation therapies described herein; thus thrombin concentrations may be measured and applied by the devices and/or systems described herein to assess the effect of the therapy and adjust delivery parameters. Thrombin concentration measurements, further to the example, may be assessed using blood from the wound, and the resulting measurements may be delivered to the treatment device and/or system to modulate therapy application.

In another example, a microfluidics chip may be used as a sensor system for actively monitoring coagulation in real-time (see Lei, Kin Fong, et al. "Real-time electrical impedimetric monitoring of blood coagulation process under temperature and hematocrit variations conducted in a microfluidic chip." PLOS One 8.10 (2013): e76243.). Electrical impedance measurements collected via the microfluidics chip, further to the example, may be analyzed to assess the effect of the therapy in real-time and adjust as needed.

In yet another example, a "lab on a chip" concept can be used to monitor and/or control therapy application. A closed-loop neuromodulation of hemostasis can be achieved with "lab on a chip" microfluidics technology. For example, a drop of blood collected from a lancet-induced finger stick could be collected in a capillary tube and then placed on a test strip that is pre-loaded with bioreceptors that selectively recognize and bind to a biomarker of interest. The bioreceptors are immobilized on a surface of a component of the test strip, and binding of the biomarker to the bioreceptor generates a signal that can be detected by a device engineered to receive that test strip and detect the signal. Biomarkers of interest include, for example, thrombin or thrombin-antithrombin III complex. The bioreceptors can be antibodies, synthetic chemicals, or engineered biological derivatives (e.g., nucleic acids, proteins or enzymes). The signal can be detected through various means including electrical, mechanical, thermal, piezoelectric, or optical. Examples of optical sensing include spectral analysis at specific wavelengths of light, such as a streptavidin-peroxidase enzymatic reaction that generates a yellow color, the intensity of which is directly proportional to the concentration of the biomarker being analyzed. The device that accepts the test strip and reads the signal can use microfluidics to wash away unbound material, or may be operable in a complete sample.

In an additional example, as shown amongst others, by Murphy and colleagues (Murphy, Peter R., et al. "Pupil diameter covaries with BOLD activity in human locus coeruleus." Human brain mapping 35.8 (2014): 4140-4154.), activity in the locus coeruleus can be indirectly measured by pupillometry. As stated earlier, activity at the LC can drive activity in the sympathetic pathway leading to activation of the spleen and, as such, pupillometry can not only be use assess the response to therapy but it can also be used to control its delivery. There are several portable automated pupilometers available (e.g., NPi®-200, Neuroptics Inc. Irvine, CA, USA) which can be used (e.g., small modifications) to automatically send pupil diameter information treatment devices and/or systems and described herein. Additionally, as discussed above, imaging of pupillary changes (e.g., pupillary dilation) captured by a common portable computing device such as a cellular phone and/or smart-glass glasses could be used monitor pupil diameter.

The monitoring used may be based, in part, on a treatment setting. For example, EEG monitoring is easier in a hospital setting, while heart rate monitoring may be achieved by a sensor such as a pulsometer built into the earpiece or another sensor built into a low budget health monitoring device such as a fitness monitoring device or smart watch. Further, microfluidics chip and lab-on-a-chip monitoring may be more practical in a hospital or clinical setting, while pupil dilation may be monitored with ease in a variety of environments.

In an illustrative example, feedback related to electrodermal activity could be used to monitor and detect a speed or timing of a symptom and/or therapeutic outcome. In an example, the electrodermal activity could be sensed by electrodes on the therapeutic earpiece device. In another example, electrodermal activity could be detected by electrodes on another portion of the body and communicated to the system. In some embodiments the electrodermal electrode can be such that it detects specific substances in the skin (e.g., cortisol) via electrochemical means.

In some implementations, the system can further include one or more motion detectors, such as accelerometers or gyroscopes, that can be used gather information to modulate the therapy. In an example, the one or more motion detectors are configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In an aspect, feedback from glucose monitoring can be used to modulate the therapy.

In yet other implementations, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert a patient/caregiver if therapy is not being adequately delivered and if the treatment device is removed.

In some embodiments, sensor data may be monitored to determine if and when to initiate a particular therapy. For example, one or more blood tests may be automatically or semi-automatically conducted (e.g., on a periodic basis) to monitor for differences in a subject's coagulation pathway functionality. The tests, for example, may be manually activated and automatically analyzed. As mentioned earlier, the coagulation pathways are normally divided into three: the intrinsic, extrinsic, and common pathways. Different tests are commonly used to assess the function of both intrinsic and extrinsic pathways. For example, a test known as activated partial thromboplastin time (aPTT), also known as partial thromboplastin time (PPT), can be used to assess the function of coagulation via the intrinsic and common coagulation pathways. As such, the aPPT test evaluates coagulation factors XII, XI, IX, VIII, X, V, II, and I. For example, someone with a coagulation deficiency such as hemophilia will have a long or elevated PTT. However, because various embodiments of the blood management therapies described herein enhance platelet-driven coagulation in a manner that is independent or quasi-independent from coagulation factors, PTT could be shortened by the therapies even in hemophilic people. Another test also assessing the same pathways as the PTT is the activated clotting time (ACT) test. Thus, PTT (or ACT) could be used to assess when to apply neurostimulation therapy. On the other hand, prothrombin time (PT) is generally used to test coagulation via the extrinsic and common coagulation pathways; thus, PT assesses the function of coagulation factors VII, X, V, II, and I. In another example, PT can used to assess the effects of the therapy and thus to determine when to reinitiate the stimulation therapy. PT, as well as PTT and ACT can be assessed via various handheld devices available on the market today (e.g. Coag-Sense® PT meter from Coag-Sense, Inc., https://coag-sense.com/, CL1000 (from EasyDiagnosis, https://www.easydiagnosis.com/CL1000.html). The PTT, PT, and/or ACT measurements, for example, may be automatically (e.g., through a wireless connection) delivered to a treatment device and/or system (e.g., cloud-based analytics engine) as described herein, for analysis in determining how to control therapy delivery.

In some embodiments, stimulation pulses are delivered in pulse patterns. Individual pulses in the pattern may vary in frequency and/or pulse width. Patterns may be repeated in stimulation cycles. The pulse pattern, for example, may be designed in part to ramp up stimulation, establishing a comfort level in the wearer to the feel of the stimulation. In another example, the pulse pattern may be designed in part to alternate stimulation between stimulation sites where two or more sites are being stimulated during therapy. In examples involving multiple stimulation sites, the stimulation pattern may be designed such that stimulating frequencies are not the same in all sites at which stimulation is being delivered.

In some embodiments involving electrical stimulation utilizing either percutaneous or transcutaneous (i.e., non-penetrating) electrodes, the stimulation frequencies vary within a set of ranges. For example, the stimulation frequencies applied in a stimulation pattern may include a first or low frequency within a range of about 1 to 30 Hz, a second or mid-range frequency within a range of about 30 to 70 Hz, a third or high frequency within a range of about 70 to 150 Hz; and/or a fourth or very high frequency within a range of about 150 to 300 Hz.

TABLE 5

Electrical Therapy: Frequency Table
Electrical therapy: Frequency Table

| Frequency designation | Range in Hz |
|---|---|
| Low frequency | 1-30 |
| Mid-range frequency | 30-70 |
| High frequency | 70-150 |
| Very high frequency | 150-300 |

In one embodiment, a stimulation frequency is varied between 2 Hz and 100 Hz. In yet another embodiment, the pulse width can be adjusted from between 20 and 1000 microseconds to further allow therapy customization. Stimulation frequency is an important differentiator between neural networks; for example, using a high frequency has been shown to be beneficial in activating the desired trigeminal system features; in contrast, a low frequency is preferred in activating the desired vagal features. Thus, in a preferred embodiment, a combination of low frequency and high frequency is applied respectively to activate vagal and trigeminal branches in accordance with various embodiments described herein. In yet another embodiment, a variable frequency (e.g., stimulating at a non-constant frequency) can be used at one or more of the electrodes. The variable frequency can be a sweep, and/or a random/pseudo-random frequency variability around a central frequency (e.g., 15 Hz+/−1.5 Hz, or 100 Hz+/−10 Hz). Varying the stimulation frequency in a random or pseudo-random way can help to prevent neural accommodation.

When using electrical stimulation, different combinations of pulse widths can be used at each electrode. Pulse widths, in some examples, may range from one or more of the following: first or short pulse widths within a range of about 10 to 50 microseconds, or more particularly between 10 to 20 microseconds, 20 to 30 microseconds, 30 to 40 microseconds, 40 to 50 microseconds; second or low mid-range pulse widths within a range of about 50 to 250 microseconds, or more particularly between 50 to 70 microseconds, 70 to 90 microseconds, 90 to 110 microseconds, 110 to 130 microseconds, 130 to 150 microseconds, 150 to 170 microseconds, 170 to 190 microseconds, 190 to 210 microseconds, 210 to 230 microseconds, or 230 to 250 microseconds; third or high mid-range pulse widths within a range of about 250 to 550 microseconds, or more particularly between 250 to 270 microseconds, 270 to 290 microseconds, 290 to 310 microseconds, 310 to 330 microseconds, 330 to 350 microseconds, 350 to 370 microseconds, 370 to 390 microseconds, 390 to 410 microseconds, 410 to 430 microseconds, 430 to 450 microseconds, 450 to 470 microseconds, 470 to 490 microseconds, 490 to 510 microseconds, 510 to 530 microseconds, or 530 to 550 microseconds; fourth or long pulse widths within a range of about 550 to 1000 microseconds, or more particularly between 550 to 600 microseconds, 600 to 650 microseconds, 650 to 700 microseconds, 700 to 750 microseconds, 750 to 800 microseconds, 800 to 850 microseconds, 850 to 900 microseconds, 900 to 950 microseconds, or 950 to 1000 microseconds; and/or a fifth or very long pulse widths within a range of about 1000 to 4000 microseconds or more particularly between 1000 to 1250 microseconds, 1250 to 1500 microseconds, 1500 to 1750 microseconds, 1750 to 2000 microseconds, 2000 to 2250 microseconds, 2250 to 2500 microseconds, 2500 to 2750 microseconds, 2750 to 3000 microseconds, 3000 to 3250 microseconds, 3250 to 3500 microseconds, 3500 to 3750 microseconds, 3750 to 4000 microseconds. Different embodiments can use different ranges of pulse widths at one or more of the electrodes. The selection of the stimulation pulse width depends on the desired target fiber as well as the output intensity. For example, given a similar intensity, activation of C type fibers generally requires a longer pulse width than activation of a myelinated Aβ fiber. In a preferred embodiment, the use of a low mid-range pulse is used in order to preferably activate myelinated fibers.

TABLE 6

Electrical therapy: Pulse Width Table
Electrical Therapy: Pulse Width Table

| Pulse width designation | Range in microseconds |
|---|---|
| Very short pulse | 10-50 |
| Short pulse | 50-150 |
| Low mid-range pulse | 151-350 |
| High mid-range pulse | 351-550 |
| Long pulse | 551-1000 |
| Very long pulse | 1001-4000 |

Activity on the VEF can be modulated by electrical stimulation at various sites. For example, the vagus nerve ascends inside the carotid sheath along the neck (e.g., cervical vagus) where it can be non-invasively stimulated in a transcutaneous way, for example using patch electrodes or a device such as the one described by U.S. Pat. No. 10,207,106 to Simon et al. The cervical vagus can also be stimulated invasively using an implanted electrode powered externally, or using a fully implantable system such as the system described in U.S. Pat. No. 8,571,654 to Libbus et al. The implantable system, for example, may provide low frequency stimulation (e.g., 1 to 30 Hz) to the cervical vagus and/or descending vagal pathways. These same invasive/implantable methods can be used to stimulate the splenic nerve and thus increase spleen activity. Other methods of stimulation can be used such as, in some examples, ultrasound, which can also be used to directly activate the spleen (see, e.g., U.S. Patent Application Publication No. 2011/0190668 to Mishelevich), or light (see, e.g., U.S. Pat. No. 8,562,658 to Shoham et al.).

Activity on the VEF can also be modulated by stimulating the auricular branch of the vagus nerve (ABVN) and/or by stimulating a branch of the trigeminal nerve. Each of these pathways activate neurons in the Nucleus of the Solitary Track (NTS) which directly and indirectly increases VEF activity. Trigeminal nerves approach the subcutaneous region at several locations in the face; for example, the auriculotemporal nerve (ATN), the Supraorbital nerve, Supratrochlear nerve, Infratrochlear nerve, Palpebral branch of lacrimal nerve, External nasal nerve, Infraorbital nerve, Zygomaticofacial nerve, Zygomaticotemporal nerve, Mental nerve, and Buccal nerve are potential trigeminal targets to deliver transcutaneous stimulation. A device placing electrodes such that any of these branches is stimulated can be used to increase the coagulation potential via activation of the VEF. For example, a device such as the one described by U.S. Pat. No. 10,207,106 to Simon et al. could be utilized to stimulate a branch of the vagus nerve. In a similar manner, the device described by U.S. Pat. No. 8,914,123 to Rigaux can be used to stimulate a branch of the trigeminal nerve. Further, although cumbersome, both devices could be used simultaneously or in an alternating manner to elicit a vagal, a trigeminal, or a trigemino-vagal response. The ABVN can be stimulated at the auricle, the preferential targets for this purpose being the cymba concha, the concha, the tragus and/or inside the ear canal, as well as behind the ear in or around the mastoid canaliculus (McS); a.k.a. Arnold's canal. The ATN can be stimulated in or around the auricle; for example immediately rostral to the auricle on top of and/or above the temporomandibular joint (TMJ). The ABVN as well as the trigeminal nerve branches can be activated individually, simultaneously, or sequentially, such as in an interleaved manner. Further, these nerves can be stimulated invasively using percutaneous electrodes (e.g., as described by U.S. Pat. No. 8,942,814 to Szeles) or as in U.S. Patent Application Publication No. 2018/0200522 to Taca Jr.) or non-invasively using transcutaneous electrodes (e.g., as described by U.S. Pat. No. 11,351,370 to Covalin et al., incorporated herein by reference in its entirety).

Turning to FIG. 6A and FIG. 6B, in a preferred embodiment, stimulation may be provided transcutaneously using an auricular stimulation device 600. The auricular stimulation device 600 is shown having electrodes 602, 604, 606, and 608. The electrodes 602, 604, 606, and 608, for example, may be configured to form corresponding circuits 610a and 610b according to an example. In an example, equivalent circuit 610a may be formed by electrode 602 and electrode 606 which are configured to stimulate tissue portion 620. In this example, tissue portion 620 is positioned to target the cymba conchae region which is enervated by branches of the auricular branch of the vagus nerve and the region behind the ear which is enervated by branches of the great auricular nerve and branches of the lesser occipital nerve. In an example, equivalent circuit 610b may be formed by electrode 604 and electrode 608 which are configured to stimulate tissue portion 622. In this example, tissue portion 622 may be positioned to target the region rostral to the ear under which the Auriculotemporal nerve transmits and gives out branches, as well as the region behind the ear which is enervated by branches of the great auricular nerve and branches of the lesser occipital nerve.

In an example, the tissue portion 620 can be the concha, the cybma concha, or a portion of both, which allows for ABVN stimulation and is stimulated at approximately 5 Hz or at 15 Hz, or at 30 Hz. In an example, the tissue portion 620 can be disposed in a region of the trigeminal nerve which is stimulated at approximately 80 Hz, or at 100 Hz or at 120 Hz or at 150 Hz.

In an example, equivalent circuit 610a is stimulated by a first channel and equivalent circuit 610b is stimulated by a second channel.

Turning to FIG. 6C and FIG. 6D, in some embodiments, stimulation may be provided transcutaneously using the electrodes 642a, 642b, and 642c of the auricular stimulation device 630. The electrodes 642a, 642b, and 642c, for example, may be configured to form corresponding circuits 650a and 650b.

In a first example, equivalent circuit 650a may be formed by electrode 642b and electrode 642c which are configured to stimulate tissue portion 652a. In this example, tissue portion 652a may be positioned to target the ATN in or around the area rostral to the auricle in proximity to the TMJ. For example, the equivalent circuit 650a may be designed to deliver stimulations to modulate activity in the VEF.

In a second example, equivalent circuit 650b may be formed by electrode 642a and electrode 642c which are configured to stimulate tissue portion 652b. In this example, tissue portion 652b may be positioned to modulate activity in the VEF by stimulating the AVBN in or around the McS.

In yet another example, to achieve a synergetic outcome, both the AVBN and the ATN are stimulated respectively in or around the McS and in or around the area rostral to the auricle in proximity to the TMJ. In this scenario, for example, both the AVBN and the ATN may be stimulated approximately at the same time in an interleaved manner. In illustration, each of electrodes 642a and 642b may be multiplexed with electrode 642c to form a circuit and forced current on to tissue 652a and tissue 652b in an alternating fashion. In another example, the AVBN and the ATN may be stimulated simultaneously.

In some embodiments, equivalent circuit 650a is stimulated by a first channel and equivalent circuit 650b is stimulated by a second channel.

Figure 6F:
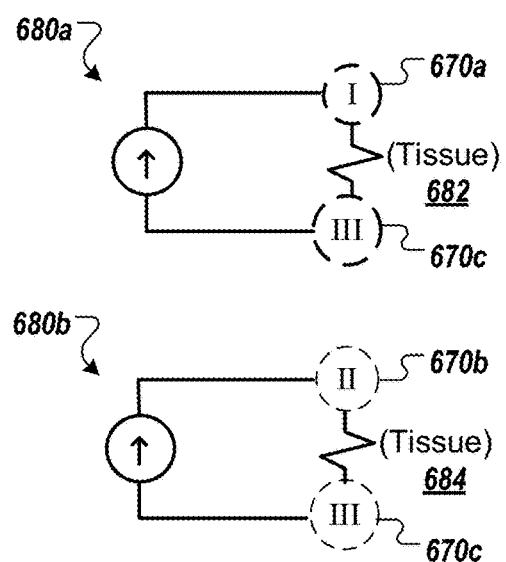

Turning to FIG. 6E and FIG. 6F, the auricular stimulation device 660 is shown having electrodes 670a, 670b, and 670c. The electrodes 670a, 670b, and 670c, for example, may be configured to form corresponding circuits 680a and 680b according to an example. In an example, equivalent circuit 680a may be formed by electrode 670a and electrode 670c which are configured to stimulate tissue portion 682. In this example, tissue portion 682 may be positioned to target the cymba conchae region which is enervated by branches of the auricular branch of the vagus nerve (e.g., positioned for stimulation by the first electrode 670a) and the region behind the ear (e.g., positioned for stimulation by the third electrode 670c) which is enervated by branches of the great auricular nerve and branches of the lesser occipital nerve. In a second example, equivalent circuit 680b may be formed by electrode 670b and electrode 670c which are configured to stimulate tissue portion 684. In this example, tissue portion 684 may be positioned to target the region rostral to the ear (e.g., positioned for stimulation by the second electrode 670b) which is enervated by the auriculotemporal nerve as well as the region behind the ear (e.g., positioned for stimulation by the third electrode 670c) which is enervated by branches of the great auricular nerve and branches of the lesser occipital nerve.

In some embodiments, the tissue portion 682 is a tissue region of the concha, the cymba concha, or a portion of both, which is stimulated at approximately 5 Hz or at 15 Hz, or at 30 Hz. In some embodiments, the tissue portion 684 is disposed in a region of the trigeminal nerve which is stimulated at approximately 80 Hz, or at 100 Hz or at 120 Hz or at 150 Hz.

In some embodiments, equivalent circuit 682 is stimulated by a first channel and equivalent circuit 684 is stimulated by a second channel. The first and second channels may be activated simultaneously and/or in an interleaved manner.

In some embodiments, electrical stimulation therapy for bleeding management as described herein is performed using splenic nerve stimulation. In other embodiments, the spinal root (sometimes called dorsal root ganglion or DRG) making the thoracic greater splanchnic nerve can be the stimulation target (a.k.a. the splanchnic DRG). In further embodiments, the celiac ganglia could be targeted for stimulation. These neural structures, as well as the spleen directly, for example, may be stimulated transcutaneously using ultrasound (e.g., focus or confocal ultrasound/high intensity ultrasound). In another example, an implantable electrode or device may be used to stimulate these neural structures (i.e., splenic nerve, celiac ganglion, DRG) as well as the spleen. The implantable mechanism, further to the example, may be configured to provide low frequency stimulation (e.g., 1-30 Hz) when activated. Activation may be achieved through programming (e.g., periodic activation), external triggering (e.g., through a wireless signal), and/or external powering (e.g., by bringing an external inductively-coupled power source within range of an inductively charged implantable mechanism). With external triggering, for example, treatment may be timed based upon a patient's need, which can, for example, reserve power in a battery operated device. Each therapeutic activation of the spleen or splenic nerve, for example, may involve short trains of pulses, such as turning stimulation on for a short period of time (e.g., 0.5, 1, 2, or 5 seconds, etc.) followed by a rest period of at least the same duration (e.g., 0.5, 1, 2, or 5 seconds, etc.) or up to about 5 times longer than the on duration (e.g., up to about 2.5, 5, 10, or 25 seconds, etc.).

Example Human Studies Involving Non-Invasive Stimulation Using an Auricular Neurostimulation Device FIG. 8A through FIG. 8E demonstrate results of three human studies using a dual nerve, dual frequency approach in a non-invasive manner. Using this novel approach, the inventors were able, for the first time, to enhance hemostasis both in healthy humans as well as in humans suffering from platelet disfunction. In all three experiments, the inventors obtained relevant and clinically meaningful results showing a clear enhancement in the hemostasis process.

In one experiment, blood loss was assessed during a clinical study in which subjects in a chronic condition needing constant dialysis underwent a dialysis port removal procedure. Subjects were randomly divided between a sham group and an active group. The subjects in both groups were fitted with an ear-mounted neurostimulation device such as those described in the present disclosure; however, only the active group received neurostimulation therapy as described herein.

The therapy provided to the active group consisted of 30 minutes of stimulation prior to the surgical dialysis port removal procedure. In particular, 30 Hz and 100 Hz stimulation was transcutaneously delivered in and around the auricle (transcutaneous auricular stimulation—tAN), respectively to skin in close proximity to AVBN and trigeminal nerve branches.

The study demonstrated a marked difference in the amount of blood lost between the two groups. As illustrated in a graph 800 FIG. 8A, the blood lost by the participants in the sham group 802 was on average close to four times (367%) the amount of blood lost by the participants in the active group 804. As illustrated, the sham group 802 lost an estimated blood volume of around 37-38 ml, while the subjects in the active group 804 lost an estimated blood volume of around 11-12 ml. This is a remarkable outcome given that the participants suffer from platelet disfunction.

In a second human study, prothrombin time (PT) was measured before and after stimulation was applied to healthy human participants. PT assesses the speed at which coagulation occurs and thus plays a significant role in the amount of blood loss following an injury. In this experiment, PT was measured from a blood sample taken from the participants before any stimulation was delivered. Next, the subjects were fitted with an ear-mounted neurostimulation device such as those described in the present disclosure, and a stimulation protocol similar to that described in relation to the timing diagram 720 of FIG. 7B was applied to all subjects for fifteen minutes (e.g., a short duration). In the study, a first stimulation pattern having a frequency of 100 Hz was directed to the ATN and a second stimulation pattern having a frequency of 30 Hz was directed to the Arnold's Nerve. Following the stimulation session, a new blood sample was obtained from each participant and PT was assessed from the new blood sample.

Figure 8A:
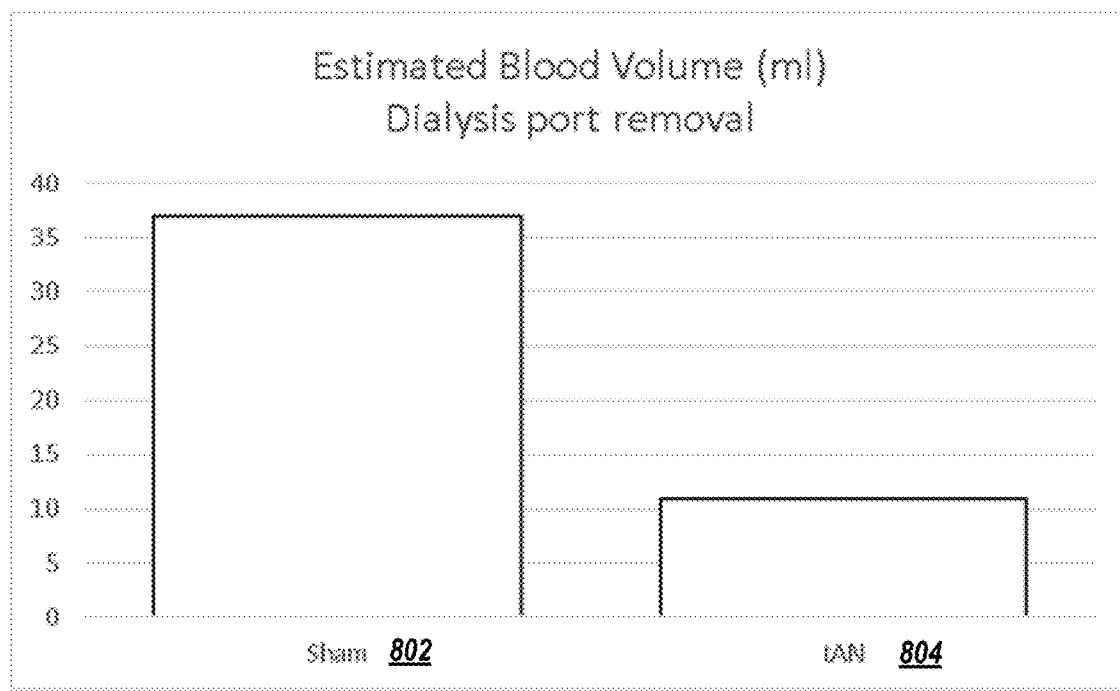
FIG. 8A through 8E are graphs demonstrating results of stimulating humans according to embodiments of the present disclosure.
Figure 8B:
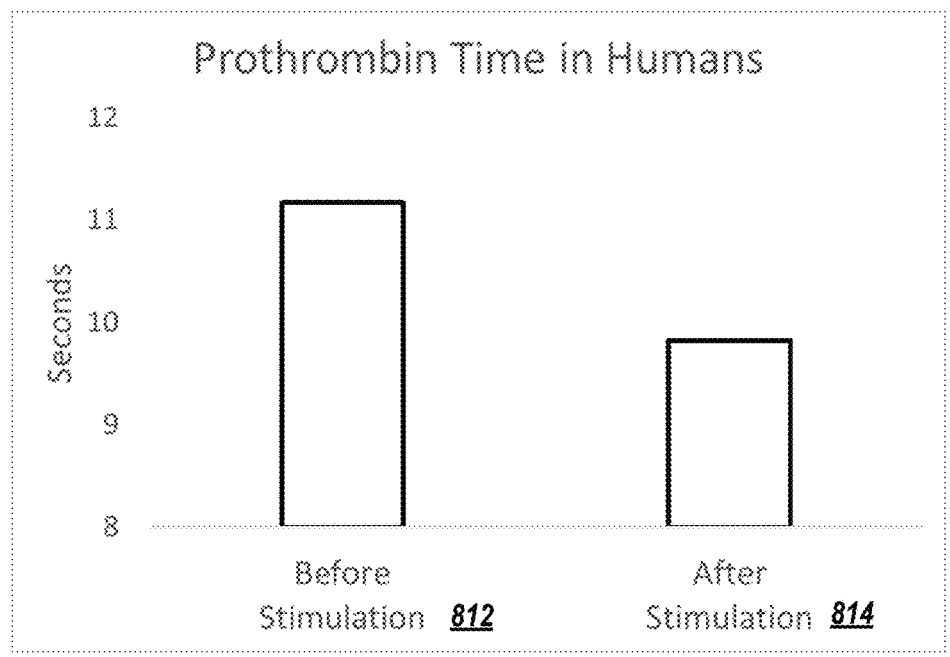

Turning to FIG. 8B, a graph 810 demonstrates a difference in human prothrombin time prior to stimulation 812 (e.g., about 11.2 seconds) as compared to after stimulation 814 (e.g., about 9.8 seconds). This represents a 12% (std 0.013) improvement in the coagulation speed (i.e., increasing the coagulation potential). Worth noting is that all subjects had the same qualitative response, and a very similar quantitative response, as can be seen by the standard deviation (STD) and coefficient of variation (CV) in Table 7 below. In the study, PT was measured using whole blood via fingertip lancet both prior to the onset of stimulation and about one minute post cessation of stimulation.

TABLE 7

Human Study Results: Prothrombin Time
Prothrombin Time in seconds

|  | BEFORE | AFTER |
| --- | --- | --- |
| Mean | 11.175 | 9.825 |
| STD | 0.789 | 0.640 |
| CV | 7.06% | 6.51% |

Figure 8C:
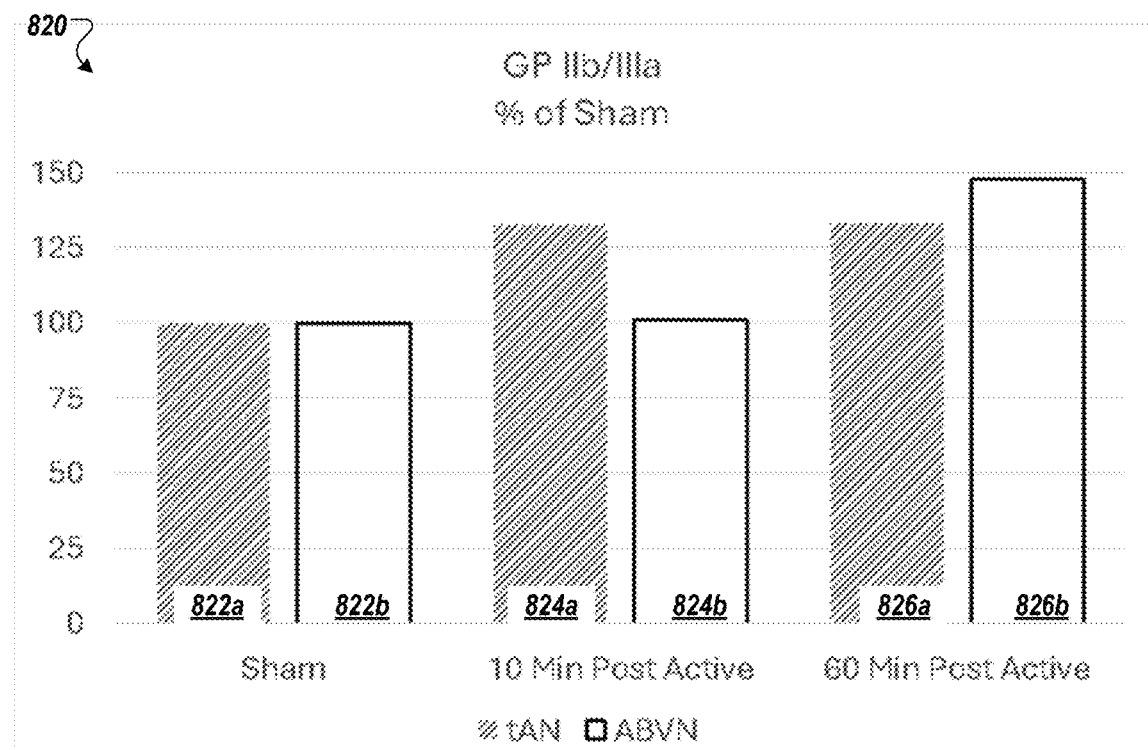
Figure 8D:
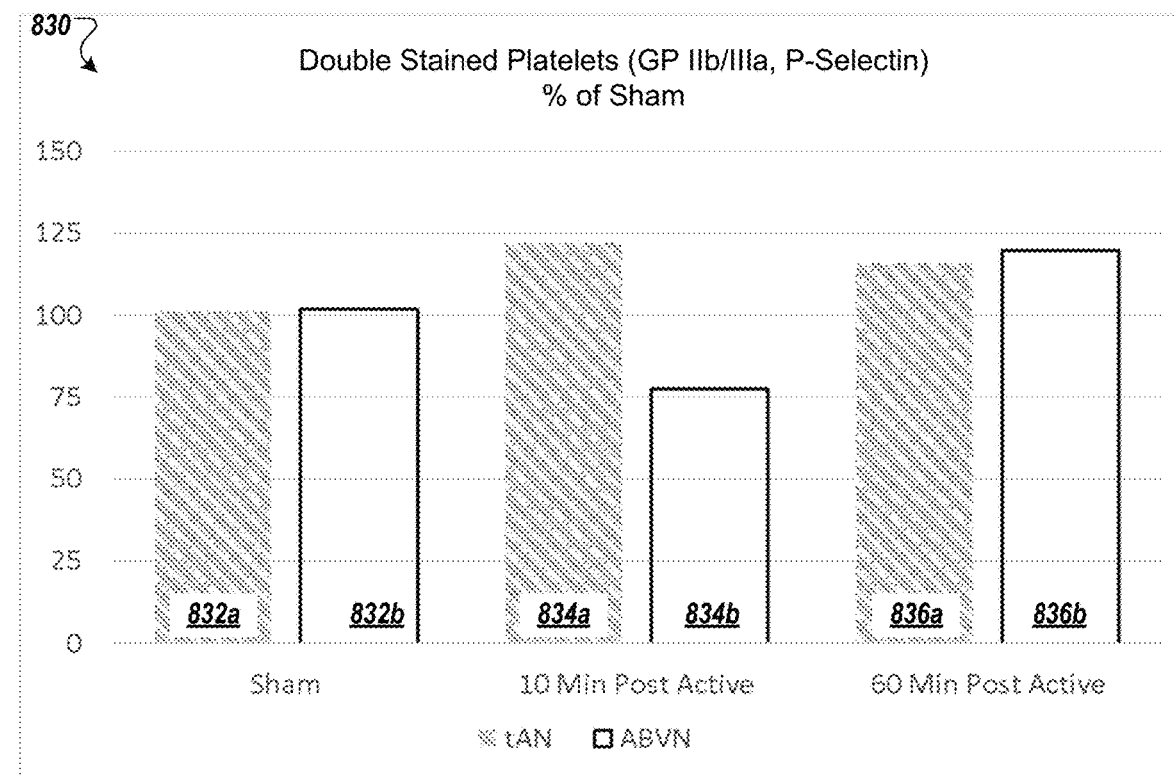
Figure 8E:
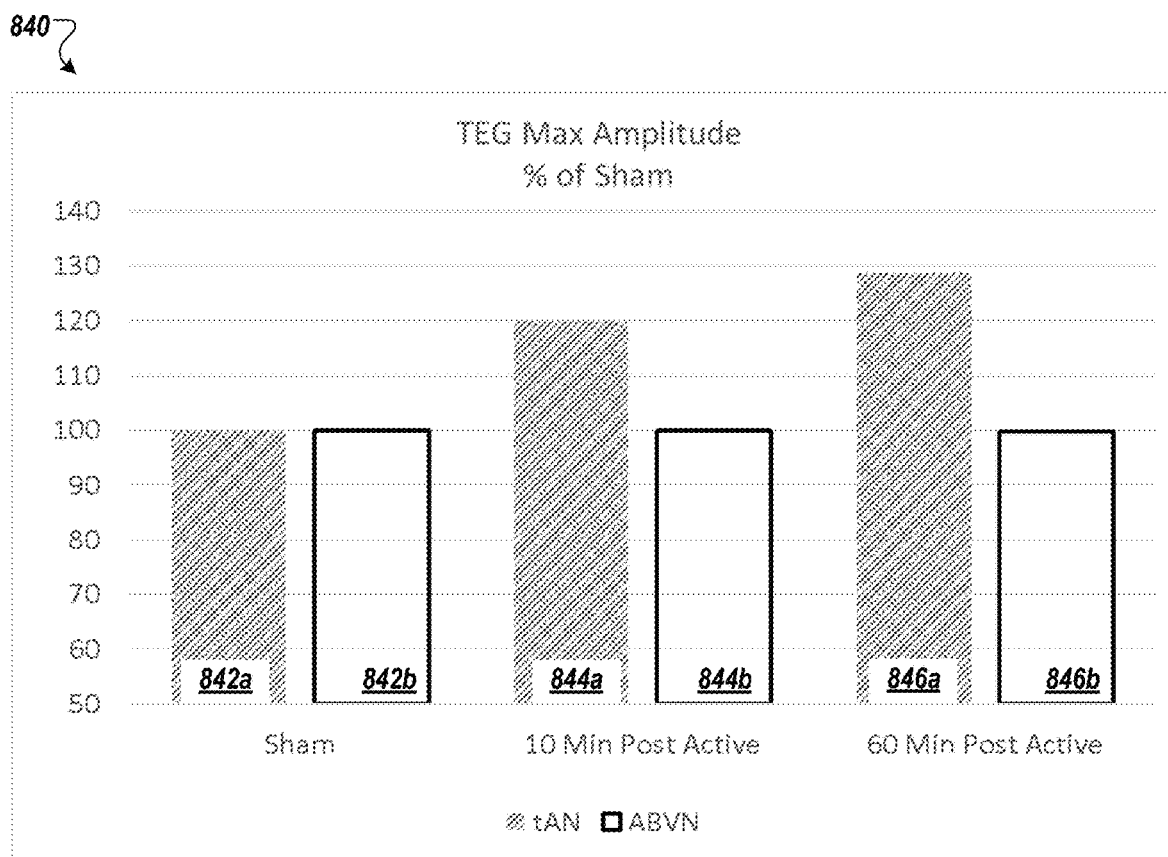

FIGS. 8C, 8D, and 8E present results achieved through a third study involving healthy human subjects divided into two groups (ABVN and tAN groups). All participants in both groups were fitted with an ear-mounted neurostimulation device such as those described herein, and all participants underwent a sham stimulation session followed by an active stimulation session. In all cases baseline measurements were taken prior to the sham measurements. Analysis of the data demonstrated no significant differences between the baseline and the sham measurements; thus, only the sham measurements are provided herein.

For the third study, the ABVN group received stimulation therapy as described herein on the auricle skin at a location adjacent or in close proximity to an area enervated by the ABVN; in particular at the cymba concha. The tAN group received stimulation therapy as described herein, both on the auricle skin at a location adjacent or in close proximity to an area enervated by the ABVN (in particular at the cymba concha) and in an area adjacent or in close proximity to where the auriculotemporal nerve surfaces. Additionally, both groups received a "sham" stimulation with the electrodes located at the same locations as when stimulation was actually applied (active stimulation). The only difference between active and sham stimulation was that during the sham stimulation period, stimulation intensity was set to zero; that is, no electrical current was delivered during the sham stimulation period.

Both groups showed an increase in hemostatic activity. The results were qualitatively and, early on, quantitatively distinct between the groups. Experiments assessed, amongst other things, the change in the surface expression of two key molecules, Glycoprotein (GP) IIb/IIIa and P-Selectin. Some platelets show exclusively an increase in one of these molecules while other platelets showed an increase in both molecules (double stained). Turning to a graph 820 of FIG. 8C, the sham results 822a, 822b establish a comparison point. As illustrated in sixty minute post-active measurements 826a, 826b, both groups demonstrated an increase of Glycoprotein (GP) IIb/IIIa expression on the platelet surface. However, the GP IIb/IIIa increase in the ABVN group was slower, lacking significant evidence of efficacy in an initial measurement period 824b taken ten minutes after the stimulation therapy. Conversely, the initial tAN measurements 824a were substantially identical to the sixty minute post active measurements 826a.

A similar response was obtained when looking at the amount of platelets that showed a change simultaneously in both P-Selectin and GP IIb/IIIa surface expression; this is illustrated in graph 830 of FIG. 8D. As illustrated, both groups demonstrated an increase in cells expressing both P-Selectin and GP IIb/IIIa 836a, 836b although, as compared to the sham measurements 832a, 832b, the tAN group response 834a, 836a exhibited faster, while the ABVN group response 834b, 836b did not register an increase until the later sixty minute measurements.

Clot retraction is greatly influenced by the presence of the GP IIb/IIIa receptor on the platelet surface. Clot retraction assists in healing the wound by bringing the separated edges of the wound closer and closer together until the wound is healed. Thus, by promoting changes to the GP IIb/IIIa receptor, subjects in both groups are anticipated to enjoy the benefit of accelerated time to heal.

In addition, turning to FIG. 8E, using thromboelastography (TEG) to analyze coagulation profiles, the maximum density of blood clots (TEG MA) was markedly increased in the tAN group, but not in the ABVN group. As illustrated, in comparison with sham results 842a, 842b, at ten minutes after active stimulation, the tAN group results 844a demonstrated an average increase in TEG MA of approximately 20%. Further, one hour after active stimulation ceased, the average increase in the tAN group results 846a showed an increase of nearly 30%. The individuals represented in the tAN group all demonstrated at least a 10% increase in TEG-MA by the time of the 60 minute analysis, while a majority of subjects demonstrated at least a 20% increase by the time of the 60 minute analysis. An increase in clot density makes the clot stronger and more capable of stopping bleeding faster. Conversely, individuals suffering from a low TEG MA (e.g., having thrombocytopenia, thrombocytopathia, etc.) would typically be treated with a platelet transfusion to manage bleeding, since there is no pharmaceutical solution available to increase clot density. Thus, according to initial results and without being bound to a theory, the inventors anticipate that the electrical stimulation therapies described herein provide the benefit of enhancing platelet-mediated coagulation. In other words, individual platelets are enhanced to perform better in coagulating than prior to stimulation.

Figure 9:
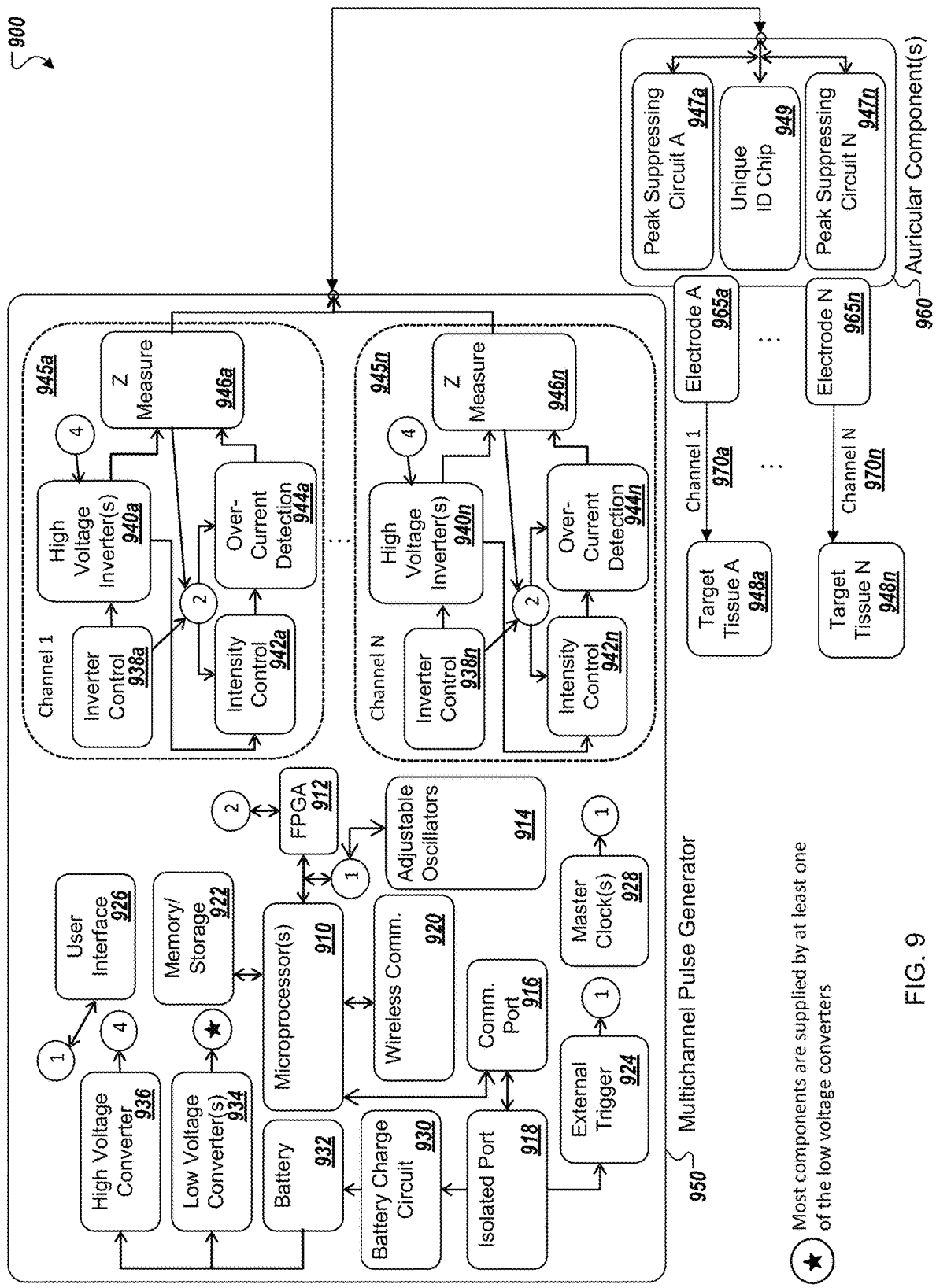
FIG. 9 is a block diagram of components of an example pulse generator in communication with an example auricular therapy device.

Turning to FIG. 9, a block diagram 900 of example components of a pulse generator 950 in communication with example components of an auricular component 960 is shown. The multichannel pulse generator circuit 950, in some embodiments, has at least one microcontroller or a microprocessor 910 with at least one core. When multiple microcontrollers or multiple cores are present, for example, one may control the wireless communication 920 and other core(s) may be dedicated to control the therapy. In some implementations, a low power programmable logic circuitry (e.g., field programmable gate array (FPGA) or programmable logic device (PLD)) 912 is also provided. For example, the microcontroller 910 may be configured to switch into a low power mode as frequently as possible while the programmable logic circuitry 912 controls therapy delivery.

In some embodiments, an inverter circuit 945*a-n* is used to generate biphasic/bipolar pulses. In some embodiments, one inverter circuit 945*a-n* is used per channel 970*a-n*, while in other embodiments, a single inverter circuit 945 is used for multiple channels 970*a-n*. Each channel 9*a-n*, for example, may target a different anatomical area (e.g., tissue region) 948*a-n*. A high voltage compliance (e.g., >50V, in other embodiments >70V, and yet in others >90V) may be used to ensure there is enough margin on the electrical potential to generate current demanded by the intensity control 942*a-n* of each inverter circuit 945*a-n* by providing one or more high voltage inverters 940*a-n* per inverter circuit 945*a-n*. In order to enhance safety, in some embodiments, an over current detection circuit 944*a-n* is provided in each inverter circuit 945*a-n*. In some embodiments, an impedance measuring circuit 946*a-n* is provided in each inverter circuit 945*a-n*. The impedance measuring circuit 946*a-n*, for example, may support tracking impedance over time to identify failure of sufficient therapy delivery. In some examples, therapy delivery may be compromised when the electrodes are not in contact or in good contact with the target tissue 948*a-n*, when a cable or connector between the multichannel pulse generator 950 is disconnected from one of the auricular component(s) 960, or where the electrodes have deteriorated or are defective. Monitoring impedance over time provides the added advantage that the condition of the contact electrode can be followed; thus allowing the controller to alert the user when the contact electrodes are close to their end of life or no longer viable. The FPGA 912 may control the inverter circuits 945*a-n* and receive feedback from an inverter control component 938*a-n*.

In some implementations, a battery 932 is used to power the pulse generator 950. The battery 932, for example, may power components of the pulse generator 950 and/or the auricular component(s) 960 via a one or more low voltage converters 934. Further, the pulse generator 950 may include a high voltage converter 936, coupled to one or more high voltage inverters 940*a*-940*n*, for delivery electrical stimulation therapy via the one or more channels 945*a-n*.

In some embodiments, an isolated port 918, such as a universal serial bus (USB) is used to charge the battery 932. In other embodiments, charging of the battery is accomplished wirelessly using induction coupling (not shown). The battery 932 may be charged via battery charge circuit 930.

In some implementations, the isolated port 918 is used to communicate with the microcontroller(s) 910 (e.g., via a communications port 916). The communication can be both ways, such that instructions or entire new code can be uploaded to the microcontroller(s) 910 and information stored in a memory 922 may be downloaded. In some embodiments, the memory 922 or additional memory can be added to the circuitry as an external component (e.g., in wireless or wired communication with the pulse generator 950). For example, the isolated port 918 (e.g., USB) may be used to connect memory to the pulse generator 950. In other embodiments, at least portions of the memory 922 may be internal to the microcontroller(s) 910. In some embodiments, the FPGA 912 may also have internal memory.

In some embodiments, an external trigger circuit 924 is included, such that the stimulation can be started and/or stopped via an external signal. In some embodiments, the external trigger signal can be passed through the isolated port 918; in yet other embodiments a modified USB configuration (i.e., not using the standard USB pin configuration) can be used to pass the trigger signal. Using a modified USB configuration will force a custom USB cable to be used, thus ensuring that an external trigger cannot be provided by mistake using an off-the-shelf USB cable. In a further example, the external trigger signal may be wirelessly transmitted (e.g., by Bluetooth) from a separate source.

In some embodiments, a hardware user interface is provided for interacting with the multichannel pulse generator 950 via user interface circuitry 926. In an example, the user interface circuitry 926 can include of buttons, LEDs, haptic (e.g., piezoelectric) devices such as buzzers, and/or a display, or a combination of any of them. In some embodiments, the user interface circuitry 926 includes signal processing components for interpreting user interface commands delivered via an external device (e.g., through the wireless communications 920). The external device, in some examples, may be a smart phone app, a tablet computer, or a medical monitoring device (e.g., in a hospital setting).

In some embodiments, an external master clock 928 is used to drive the microcontroller(s) 910 and/or the FPGA 912. In other embodiments the clock(s) of the components can be internal or integrated or co-packaged with the microcontroller(s) 910 and/or the FPGA 912. In some embodiments, one or more oscillators, including in some cases adjustable oscillators 914 are used to set pulse parameters such as, for example, frequency and/or pulse width.

In some embodiments, the auricular component 960 is made from a thin flex PCB or printed electronics, such that it is light weight and can be easily bent to accommodate different anatomies. In some embodiments, the auricular component 960 has more than one channel. The auricular component 960, or each channel thereof, may include a peak suppressing circuit 947*a-n* and electrodes 965*a-n* to contact the skin at the location of the target tissue 948*a-n*. In some embodiments, the auricular component(s) 960 includes a unique chip identifier or unique ID chip 949. The unique ID chip can be used to track usage as well as to prevent other non-authorized circuits from connecting to the multichannel pulse generator 950. At least one auricular component(s) 960 is connected to the multichannel pulse generator 950.

In some embodiments, the auricular component 960 is made from a thin flex PCB or printed electronics, such that it is light weight and can be easily bent to accommodate different anatomies. In some embodiments, the auricular component 960 has more than one channel. The auricular component 960, or each channel thereof, may include a peak suppressing circuit 947a-n and electrodes 965a-n to contact the skin at the location of the target tissue 948a-n. In some embodiments, the auricular component(s) 960 includes a unique chip identifier or unique ID chip 949. The unique ID chip can be used to track usage as well as to prevent other non-authorized circuits from connecting to the multichannel pulse generator 950. At least one auricular component(s) 960 is connected to the multichannel pulse generator 950.

Figure 13:
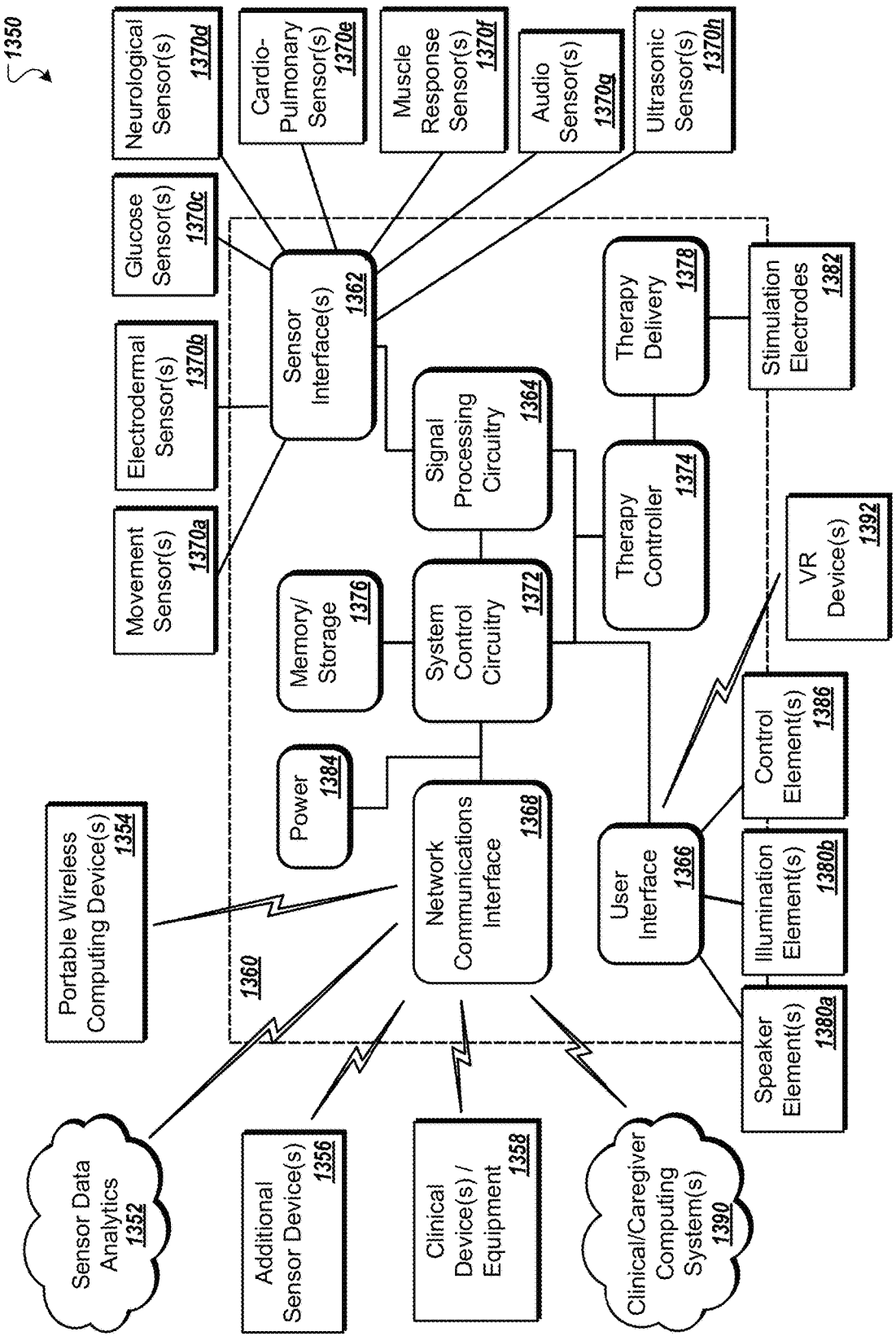
FIG. 13 illustrates an example system including a treatment device, sensor(s), and sensor signal conditioning and/or analysis circuitry.

In some embodiments, methods and systems of the present disclosure use feedback to monitor and/or modify the therapy. Turning to FIG. 13, an environment 1350 and system 1360 for using feedback in neurostimulation is illustrated. The environment 1350 and/or the system 1360 may incorporate elements of various treatment devices described herein, such as the treatment device 600 of FIG. 6A, the treatment device 630 of FIG. 6C, and/or the treatment device 660 of FIG. 6E. Further, the environment 1350 may include peripheral devices 1354, 138, 1356, 1390 and/or a network system 1532. Additionally, the system 1360 may include aspects of a multichannel pulse generator, described in detail below. The environment 1350 and system 1360, for example, may be used to analyze sensor data in real-time, allowing for closed loop neurostimulation based on feedback data related to the wearer of a neurostimulation device. In another example, feedback monitoring can be used to alert the patient, a caregiver, and/or a clinical resource regarding therapy progress and/or a problem with the therapy. For example, a caregiver or clinician may be contacted, at clinical/caregiver computing system(s) 1390, in the event that therapy is not being adequately delivered and/or if the treatment device has been removed.

In some implementations, the system 1360 is activated at least in part by initiating delivery of power via power control circuitry 1384 to the system 1360. One or more control elements 1386, for example, may provide the ability for a wearer or patient to activate the system 1360 and/or to set initial therapeutic parameters. In certain embodiments, therapy may be remotely activated and/or adjusted through an external device, such as a portable computing device 1354.

In some implementations, one or more sensor interfaces 1362 of the system 1360 obtain feedback from one or more sensors 1370. Various sensors 1370, for example, may be provided for monitoring one or more symptoms being treated by the therapy, such as, in some examples, symptoms of stress and/or anxiety, pain, nausea, fatigue, inflammation, and/or disorientation/dizziness. In another example, certain sensors 1370 may be provided to monitor for activities or actions of the wearer to coordinate therapeutic stimulation with the activity/action. In some examples, the sensors 1370 may include one or more movement sensors 1370a (e.g., motion sensors, accelerometers, and/or gyroscopes) for monitoring movement activity (e.g., tremors, physiologic movement), one or more electrodermal sensors 1370b including, in some cases, electrochemical sensors for monitoring electrodermal activity (e.g., sweating, cortisol, etc.), one or more glucose sensors 1370c for monitoring glucose level, one or more neurological sensors 1370d for monitoring neurological activity (e.g., via electroencephalogram (EEG) sensing electrodes), one or more cardio-pulmonary sensors 1370e for monitoring cardio-pulmonary activity (e.g., electrocardiogram (EKG) sensing electrodes, heart rate sensor(s), blood pressure (systolic, diastolic and mean) sensor(s), etc.), and/or muscle response sensor(s) 1370f for monitoring muscle response activity (e.g., electromyography (EMG) sensors). The sensors 1370, in another example, may include one or more audio sensors 1370g (e.g., microphones, bone conduction microphones, vibrational sensors, etc.) for obtaining sound signals (e.g., verbalizations and/or utterances, breathing sounds, heart sounds, etc.). In an additional example, the sensors 1370 may include one or more ultrasonic sensors 1370h for measuring deep tissue signals such as, in some examples, central blood pressure, cerebral blood flow velocity (CBFV), heart rate, and/or cardiac output.

The sensors 1370 may be in wired and/or wireless communication with the sensor interface(s) 1362 of the system 1360. Certain sensors 1370, for example, may be integrated into the earpiece and/or concha apparatus of an ear-mounted neurostimulation devices such as various devices described in the present disclosure. One or more sensors 1370, in another example, may be integrated into a pulse generator for neurostimulation therapy delivery. Further to the example, periodic monitoring may be achieved through prompting the wearer to touch one or more electrodes on the system 1360 (e.g., electrodes built into a surface of the pulse generator) or otherwise interact with a component of the system 1360 such as the pulse generator (e.g., hold the pulse generator extended away from the body to monitor tremors using a motion detector in the pulse generator). The prompting, for example, may be supplied via a user interface 1366 by one or more speaker elements 1380a (e.g., a verbal command) and/or one or more illumination element(s) 1380b (e.g., an LCD display, LED display, 7-segment digital display, and/or LED indicator(s) next to printed information on a surface of the system 1360).

In some implementations, the user interface 1366 is used to deliver a portion of the therapy to the wearer. For example, the system 1360 may coordinate neurostimulation therapy with a Virtual Reality (VR) device 1392. The VR device 1392, in some examples, may deliver audio, visual, and/or haptic output coinciding with the goals of a particular therapy. In example, to reduce stress and anxiety, the system may configure the VR device 1392 to provide relaxing audio and/or visual output to the wearer during neurostimulation therapy. In another example, to overcome PTSD, phobias, cravings, and/or other addiction-related triggers, the VR device 1392 may be configured to present triggering audio and/or visual content during neurostimulation therapy. Although illustrated as being a separate VR device 1392, in other embodiments, neurostimulation electrodes are built into the VR device (e.g., a VR headset) as a virtual reality-enabled neurostimulation therapy device.

In some implementations, feedback data gathered by the system 1360, such as sensor feedback, may be supplied by a pulse generator to one or more of the peripheral devices 1354, 1390. The feedback, for example, may include sensor signals related to symptoms of the patient being treated by the system 1360. A clinical user monitoring sensor metrics related to these signals may manually adjust the delivery of therapy accordingly using the one or more adjustable controls provided by the application. Further, in some implementations, the feedback may be used by one of the peripheral devices 1354, 1390 to generate a notification for review by the patient, a caregiver, or a clinician. The notification, for example, may include a low power notification, a device removed notification, or a malfunction notification. In an illustrative example, the system 1360 may monitor impedance measurements allowing closed loop neurostimulation. The notifications regarding removal or malfunction, for example, may be issued upon determining that the impedance measurements are indicative of lack of a proper contact between one or more electrodes of the treatment device and tissue on or surrounding the patient's ear. The notifications, for example, may be delivered to the patient and/or one or more third parties via an application executing on one of the peripheral devices 1354, 1390. For example, the application may issue an audible alarm, present a visual notification, or generate a haptic output on the peripheral device 1354, 1390. Further, in some embodiments, the application may issue a notification via a communication means, such as sending an email, text message, or other electronic message to one or more authorized users, such as a patient, caregiver, and/or clinician.

Conversely, in some implementations, a cloud platform having sensor data analytics 1352 accessible via the network may receive the feedback, review present metrics, and relay instructions to the pulse generator (e.g., via a Wi-Fi network or indirectly via a local portable device 1354). The pulse generator, in a further example, may gather feedback from one or more fitness monitor and/or health monitor devices 1354, 1390, analyze the feedback, and determine whether to adjust treatment accordingly.

In other implementations, the pulse generator is included in the auricular component of a treatment device; that is, the pulse generator and auricular component may be co-located such that the need for an extension cable to connect them is not necessary. The auricular component and pulse generator may be wirelessly connected to an electronic device (for example a personal computer, a tablet or a phone) 1354, 1390 and/or to a remote server 1352. In turn, in some embodiments, the electronic device 1354, 1390 is also wirelessly connected to the remote server 1352.

In some implementations, the system 1360 includes at least one isolated port for wired communication with the peripheral device(s) 1354, 1390. The isolated port, in some examples, may be a universal serial bus (USB) connection (e.g., a mini-USB connection, a micro-USB connection, a USB-C port, etc.), an Ethernet port, or a Serial ATA (SATA) connector. The isolated port, for example, may be included in the pulse generator for updating a software version running on the pulse generator or for reprogramming treatment settings of the pulse generator. The isolated port(s) may be connected to the network communications interface 1368 for enabling communications between a peripheral device 1354, 1390 and the system 1360 via the isolated port. The network communications interface 1368 may couple the isolated port to the system control circuitry 1372. For example, the network communications interface 1368 may establish a direct (e.g., wired) communication link with one of the peripheral device(s) 1354, 1390 to transfer data from a memory 1376 to the peripheral device 1354, 1390.

Further, a wireless radio frequency (RF) antenna (e.g., transmitter or transmitter/receiver), in some implementations, is included in the network communications interface 1368. The RF antenna can be in wireless communication with the peripheral device(s) 1354, 1358 directly or via the network. The RF antenna, in combination with processing circuitry for generating wireless communications may function as a broadcast antenna, providing information to any RF receiver in a receiving region of the system 1360. For example, the RF antenna may broadcast sensor data, sensor metrics, alerts, alarms, or other operating information for receipt by one or more peripheral devices 1354, 1390. In other implementations, the RF antenna, in combination with additional processing circuitry, may establish a wireless communication link with a particular peripheral device 1354, 1390. The wireless communication link, in some embodiments, is a secure wireless communication link (e.g., HIPAA-compliant) for sharing patient data with the peripheral device(s) 1354, 1390. The wireless communication link may be used to receive control settings from a peripheral device 1354, 1390 for controlling the functionality of the pulse generator, for example.

In some implementations, sensor data is received via a network communications interface 1368 from the one or more portable wireless computing devices 1354. In some examples, sensor elements of a common smart phone, smart glasses, smart rings, and/or smart watch (e.g., accelerometer, gyroscope, microphone, image sensor (e.g., cameras), heart rate monitor, oxygen saturation, blood pressure, glucose sensor, etc.) may be used by an application designed to interoperate with the system 1360 to supply sensor data to the system 1360. In illustration, imaging (e.g., video) of pupillary changes (e.g., pupillary dilation) may be captured by a smart phone or smart glasses and used by the system 1360 as feedback for making therapy adjustments. The pupillometry measurements, for example, can be used as a measure of attention, alertness, or wakefulness (or the lack thereof). Thus, the feedback may be used to adjust therapy to maintain a desired level of attention, alertness, and/or wakefulness.

In some implementations, sensor data is received via the network communications interface 1368 from one or more additional sensor devices 1356. The additional sensor devices 1356, in some examples, can include fitness monitors and/or activity trackers (e.g., for providing data similar to that collected by the movement sensor(s) 1370$a$, the electrodermal sensor(s) 1370$b$, and/or the cardio-pulmonary sensor(s) 1370$e$, home health monitoring devices (e.g., digital smart blood pressure cuffs for providing data similar to that collected by the cardio-pulmonary sensor(s) 1370$e$, digital smart thermometers, etc.), and/or remote patient monitoring devices (e.g., glucometer for providing data similar to that collected by the glucose sensor(s) 1370$c$, pulse oximeter, wearable heart monitors such as a Holter monitor for providing data similar to that collected by the cardio-pulmonary sensor(s) 1370$e$, etc.).

Sensor data, in some implementations, is received via the network communications interface 1368 from one or more clinical devices and/or equipment 1358. In illustration, imaging techniques such as magnetic resonance imaging (MRI) and/or functional MRI (fMRI) could be used to adjust the therapy in a clinical setting for a given user. In other examples, data similar to that collected by the neurological sensor(s) 1370$d$, cardio-pulmonary sensor(s) 1370$e$, glucose sensor(s) 1370$c$, and/or muscle response sensor(s) 1370$f$ may be provided by various clinical equipment 1358.

In some embodiments, the type of monitoring used by the system 1360 and/or reliance on (e.g., trust in) various incoming sensor data may be based, in part, on a treatment setting. For example, neurological data captured by sensors such as the neurological sensor(s) 1370$d$ may be easier to capture in a hospital setting, while certain cardio-pulmonary data captured by sensors such as the cardio-pulmonary sensor(s) 1370$e$ (e.g., heart rate monitoring) may be achieved by capturing signals from a pulsometer built into the earpiece or another sensor (e.g., additional sensor devices 1356) built into a low budget health monitoring device such as a fitness monitoring device or smart watch.

In some implementations, the sensor interface(s) 1362 collects signals from the sensor(s) 1370 and provides the signals to signal processing circuitry 1364. The signal processing circuitry 1364, for example, may include one or more filters (e.g., a bandpass filter), amplifiers, and/or other circuitry to remove noise, isolate valid incoming signals, and/or increase signal strength. In some embodiments, the signal processing circuitry 1364 converts an analog signal to digital signal components.

In some implementations, sensor signals from the sensors 1370, portable wireless computing device(s) 1354, additional sensor device(s) 1356 and/or clinical device(s)/equipment 1358 are provided to system control circuitry 1372 for data analysis. The system control circuitry 1372, in some examples, may perform thresholding, pattern analysis, and/or variation over time analysis to recognize physiological, biological, and/or physical behaviors of a wearer of the therapeutic stimulation device corresponding to adjustments in treatment. For example, sensor data may be collected in a memory or temporary data storage region 1376 for analyzing sensor data over a predetermined period of time. The period of time may differ, in some examples, based on the type of therapy provided, the type of data analyzed, and/or the therapeutic goal. The adjustments in treatment, in some examples, can include initiating treatment, ceasing treatment, and/or adjusting one or more treatment parameters (e.g., voltage, frequency, stimulation pattern, stimulation location(s), etc.).

In some implementations, the system control circuitry 1372 provides sensor data to an external sensor data analytics system 1352 via the network communications interface 1368. The sensor data analytics system 1352, in some examples, can include an edge router, a cloud computing platform, and/or one or more networked servers configured to analyze sensor data to identify circumstances that trigger an adjustment in treatment. The analysis, in some embodiments, involves biometric fingerprint analysis where the physiological, biological, and/or physical behaviors captured in the sensor data are analyzed in view of baseline or historic physiological, biological, and/or physical behaviors of the particular wearer.

In some implementations, based on analysis of the sensor data by the system control circuitry 1372 and/or the sensor data analytics system 1352, therapy parameter adjustments are provided to a therapy controller 1374 for adjusting stimulation parameters delivered via therapy delivery circuitry 1378 (e.g., pulse generator circuitry) to a set of stimulation electrodes 1382. Therapy delivery circuitry 1378 and stimulation electrodes 1382 are discussed in greater detail above with reference to FIG. 9.

In a first illustrative example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.).

In another illustrative example, feedback related to electrodermal activity could be used to monitor and detect the speed or timing of a symptom and/or therapeutic outcome. In an example, the electrodermal activity could be sensed by electrodermal sensors 1370*b*. For example, an electrodermal patch with one or more electrodermal sensors 1370*b* can be used to estimate the individual's stress levels by assessing cortisol levels in sweat.

In an example, the one or more movement detectors 1370*a* may be configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In another example, movement and movement serial combinations can be used to assess the outcome of a training protocol aimed at restoring performance of these movements.

In a further example, feedback from glucose sensors 1370*c* can be used to modulate the therapy. People suffering from diabetes 2 lack the ability to control glucose levels, and vagal stimulation has been shown to decrease hyperglycemia. Therefore, assessing glucose levels can be used to trigger stimulation to increase glycemic control.

In an additional example, neurological sensor(s) 1370*d* and/or cardio-pulmonary sensors 1370*e* may be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In a further illustrative example, feedback signals collected by the muscle response sensor(s) 1370*f* may be analyzed to trigger stimulation during physical movement recovery, such as arm movement recovery. For arm movement recovery, multiple muscle response sensors 1370*f* can be arranged in a sleeve such as the NeuroLife® EMG Sleeve provided by Battelle Memorial Institute of Norwell, Massachusetts.

In a final illustrative example, attention, alertness, and/or wakefulness can be assessed by the ultrasonic sensor(s) 1370*h* by measuring cerebral blood flow velocity (CBFV). In such an example, CBFV can be used as feedback to adjust therapy.

In some implementations, the sensor data analytics system 1352 collects historic sensor data and treatment parameters across a population of patients and applies the collected data to performing machine learning analysis to refine therapeutic protocols and parameters at an individual level. This, for example, can lead to faster and/or a higher function recovery. Following a stroke or a TBI, in an illustrative example that may be used in a hospital setting, such as in the Intensive Care Unit (ICU) or the Neonatal Intensive Care Unit (NICU), data collected via sensors 1370 such as, in some examples, heart rate (ECG), arterial oxygen saturation (SpO2), arterial blood pressure (in some cases using an arterial catheter), central venous pressure, core temperature, blood glucose level, breathing rate and/or volume, urine output, and/or cardiac output sensors, may be analyzed and applied in automatically directing and/or adjusting neuromodulatory treatment. In further examples, the sensor data may provide insight regarding osmolarity, serum electrolytes, and/or blood gases (arterial) that, in turn, could assist in making determinations when automatically directing and/or adjusting the neuromodulatory treatment. The sensor data, in some examples, may be analyzed for evidence of a comfort level of the patient (e.g., indicators of potential pain and/or stress in the patient), evidence of inflammation, and/or evidence of ischemic processes (e.g., evidence of build-up of metabolic waste).

Figure 14:
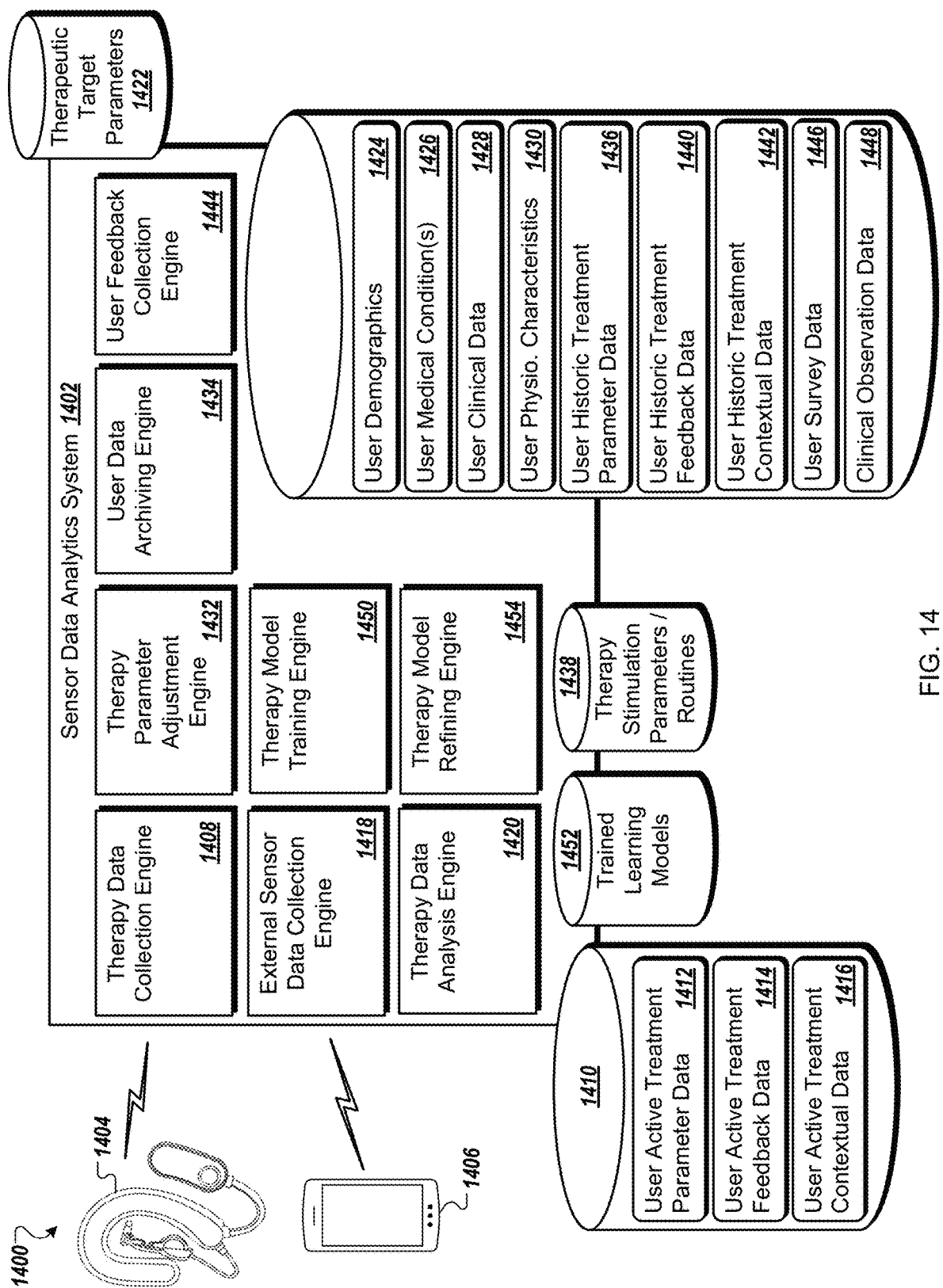
FIG. 14 is a block diagram of an example sensor data analytics system for delivering neurostimulation therapy that is customized to the wearer.

In some implementations, the sensor data analytics system 1352 applies machine learning and/or artificial intelligence (AI) analysis to refine therapy sessions to deliver more efficacious and/or more efficient treatment. Turning to FIG. 14, an example sensor data analytics system 1402 and platform environment 1400 obtains data from neurostimulation systems (e.g., devices and/or pulse generators) 1404 and/or computing devices 1406 and analyzes the data to confirm therapeutic goals are being met and/or to automatically refine therapeutic parameters to improve on the effectiveness of the present therapy.

In some embodiments, the sensor data analytics system 1352 includes a therapy data collection engine 1408 configured to collect data from the neurostimulation systems 1404 and associate the data with individual users. The therapy data collection engine 1408, in some examples, may collect, in relation to each user of each neurostimulation system 1404 and store the data to a computer-readable data storage region (user data store) 1410. The user data, in some examples, can include active treatment parameter data 1412 (e.g., stimulation pattern(s), frequenc(ies), identification of a particular therapeutic routine, identification of a particular therapeutic setting, etc.), active treatment feedback data 1414 (e.g., sensor data collected by the neurostimulation system 1404 and/or one or more other sensor devices in communication with the neurostimulation system 1404), and/or active treatment contextual data 1416 (e.g., geographic location, time of day, day of week, ambient temperature, velocity/acceleration of wearer, ambient noise level, etc.).

In some implementations, an external sensor data collection engine 1418 collects sensor data obtained by one or more devices external to the neurostimulation systems 1404 and in communication with the sensor data analytics system 1402. The devices, in some examples, can include fitness-monitoring devices (e.g., Fitbit, Apple Watch, or Garmin Smartwatch) and/or health-monitoring devices (e.g., a glucose meter, a holter monitor, an electrocardiogram (EKG) monitor, or an electroencephalogram (EEG) monitor). In further examples, the external devices may include clinical patient monitoring and/or management devices (e.g., brain monitoring, capnography monitoring, cerebral/somatic oximetry, pulse oximetry, localized and/or corporeal temperature management, etc.).

In some implementations, a therapy data analysis engine 1420 analyzes the user data stored to the user data store 1410 to gauge efficacy of ongoing and/or recently completed therapy. Evidence of efficacy, for example, may be based on a set of therapeutic target parameters 1422 associated with a given therapy. The therapy data analysis engine 1420, for example, may compare the user active treatment feedback data 1414 to threshold values and/or target ranges of values. In another example, the therapy data analysis engine 1420 may compare a duration of each symptom, as evidenced through sensor data, to a threshold duration prior to reduction or cessation of symptom. In some embodiments, the therapeutic target parameters 1422 may be clinician-adjustable such that a clinician may customize the target parameters based on a particular patient. In certain embodiments, different sets of therapeutic target parameters 1422 are provided based on, in some examples, user demographics 1424 (e.g., age, gender, etc.), user medical conditions 1426 (e.g., diagnosed diseases and/or disorders), and/or user clinical data 1428 (e.g., weight, body mass index (BMI), smoking status, drug use status, pregnancy status, etc.). In further embodiments, the therapeutic target parameters 1422 are adjusted based on user physiological characteristics 1430 (e.g., baselines or typical physiological patterns exhibited by the particular wearer).

In some implementations, the therapy analysis engine 1420, based on a difference between the therapeutic target parameters 1422 and the user active treatment feedback data 1414, provides parameter deltas and/or other feedback information to a therapy parameter adjustment engine 1432 to determine a set of adjusted treatment parameters. The set of adjusted treatment parameters may include one or more device settings (e.g., frequenc(ies), pattern(s), repetition(s), etc.). In one illustration involving repeated rehabilitation exercises, the stimulation duration may be systematically varied such that, using movement sensors (including for example, triaxial accelerometers and/or gyroscopes), a rate of improvement versus stimulation duration following triggering can be established. The steps for varying stimulation, for example, may be stored as therapy stimulation parameters and/or routines 1438. Stimulation duration may be automatically adjusted in order to increase the success rate and/or accelerate the recovery of a particular function.

In the example illustration of motor skill recovery training for a stroke patient, based at least in part on the user active treatment feedback data 1414 corresponding to a current activity or rehabilitative exercise, the therapy parameter adjustment engine 1432 may determine a next therapeutic routine and/or stimulation parameters. For example, upon sufficiency of performance of a current task, the therapy parameter adjustment engine 1432 may provide the neurostimulation system 1404 with instructions for a next task. The next task, in some examples, may be more challenging, exercise a different muscle group, and/or focus on linking learned skills into a series performance. The next task may be selected, for example, from a hierarchy or series of tasks stored as part of the therapy stimulation parameters and/or routines 1438.

In some embodiments, the therapy stimulation parameters and/or routines 1438 include one or more priming routines to be applied to a wearer of the neurostimulation systems 1404 prior to beginning therapeutic stimulation, such as a motor skills training session or PTSD recovery session. In illustration, neurostimulation for priming, or preparing cognitive pathways for a therapeutic/training session, may begin at least 1 minute, between 1 minute and 10 minutes, up to 30 minutes, and/or within an hour or so of the therapeutic training session. In another example, a priming routine may be introduced into the middle of a larger therapy routine involving multiple stages or phases of treatment. In a first illustration, therapeutic stimulation may be paired with an activity in a first training phase to, for example, develop new pathways to recover specific functions. In a second, priming, phase, priming stimulation may be used for general cognition boosting, for example while performing a motor skill routine that encompasses multiple functions (e.g., a combination of multiple movements/tasks). In a second illustration, therapeutic stimulation may be paired with exposure to stimulating input (e.g., aural, visual, and/or haptic, etc.) in a first training phase to, for example, overcome adverse reactions. In a second, priming, phase, priming stimulation may be used for general emotional well-being enhancement, for example while taking a break between stimulating input exposure.

In some implementations, the sensor data analytics system 1402 provides the adjusted treatment parameters to the corresponding neurostimulation system 1404, directly or via another computing device 1406. A user data archiving engine 1434 may also archive the user active treatment parameter data 1412 to capture the treatment parameters, prior to adjustment, as user historic treatment parameter data 1436. The adjusted treatment parameters, further, may be added or replace the prior version of the user active treatment parameter data 1412 corresponding to the subject neurostimulation system 1404.

In some implementations, the user data archiving engine 1434 collects the user data stored to the user data store 1410 for archival as corresponding user historic treatment parameter data 1436, user historic treatment feedback data 1440, and/or user historic treatment contextual data 1442. The user data archiving engine 1434, in some embodiments, de-identifies at least a portion of the archived user data 1436, 1440, and/or 1442 for use in big data analysis across multiple users of neurostimulation systems 1404.

In some implementations, in addition to automatically acquired sensor data and/or contextual data, a user feedback collection engine 1444 collects information from wearers of the neurostimulation systems 1404 and/or clinicians working with the wearers regarding the experience of using the neurostimulation system 1404. The user feedback collection engine 1444, for example, may collect user survey data 1446 regarding the wearer's experience during and/or after therapy. For example, the user may have a user interface with the neurostimulation device 1404 and/or a corresponding software application executing on one of the computing devices 1406 to submit feedback regarding the experience. The wearer feedback, in some examples, may include information regarding a stimulation comfort level, an improvement of symptoms level, and/or a comfort of wearing level. The feedback may be provided, in some examples, on a numeric scale or on a descriptor scale that is linked to a numeric scale (e.g., excellent, good, so-so, not great, unpleasant). In another example, the wearer may submit feedback regarding distress (symptoms not improving/seem worse, stimulation causing significant discomfort, etc.) in real-time that the therapy parameter adjustment engine 1432 can take into account when determining adjusted therapeutic parameters.

In some embodiments, the user feedback collection engine 1444 collects clinical observation data 1448 regarding clinicians' experiences in working with patients during therapy and/or who have been prescribed therapy. The clinical observation data 1448, in some examples, may include outcomes information (e.g., reduction or cessation in prescribed medication), diagnosis adjustment information (e.g., severity of a disorder), and/or progress information (e.g., relative recovery of capabilities).

In some embodiments, a therapy model training engine 1450 accesses the archived user historic treatment parameter data 1436, user historic treatment feedback data 1440, user historic treatment contextual data 1442, user survey data 1446 and/or clinical observation data 1448 across a population of wearers of neurostimulation systems 1404 over a period of time (e.g., one month, three months, half a year, one year, etc.) to develop one or more trained learning models 1452. The therapy model training engine 1450, for example, may apply machine learning and/or artificial intelligence to derive promising therapy stimulation parameters and/or routines, such as the therapy stimulation parameters and/or routines 1438. The therapy model training engine 1450, for example, may identify those therapy parameters, treatment schedules, and/or contextual parameters (e.g., setting, timing, etc.) associated with successful treatment. The trained learning models 1452 may include one or more models per treatment type (e.g., therapeutic regimen directed to treat a particular disease, disorder, symptom(s), etc.), per diagnoses (e.g., comorbidity such as smoking status, mental health diagnosis such as depression or PTSD), and/or per user demographic (e.g., age, gender, etc.), and/or per user type (e.g., military, athlete, etc.). The trained learning models 1452, for example, may be designed predict, based on user demographics 1424, user medical condition(s) 1426, and/or user clinical data 1428, beneficial therapy stimulation parameters and/or routines 1438 for the particular patient.

In some implementations, after initially training the trained learning models 1452, upon collecting further user historic data 1436, 1440, and/or 1442, user survey data 1446, and/or clinical observation data 1448, a therapy model refining engine 1454 updates the trained learning models 1452 using the new learning data. The therapy model refining engine 1454, for example, may refine the trained learning models 1452 on a periodic basis or ongoing as new data is collected by the sensor data analytics system 1402.

Although the sensor data analytics system 1402 is illustrated as being separate from the neurostimulation system 1404, in some embodiments, portions of the sensor data analytics system 1402 is included within the neurostimulation system 1404 and/or in a computing device 1406 in direct (e.g., wired or short rage wireless transmission range, etc.) communication with the neurostimulation system 1404. For example, to swiftly adapt ongoing neurostimulation therapy based on sensor feedback, portions of the functionality of the therapy data analysis engine 1420 may execute in real-time or near real-time on equipment local to the wearer.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations. The hardware logic may be synthesized on a reprogrammable computing chip such as a field programmable gate array (FPGA), programmable logic device (PLD), or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the pulse generator 950 of FIG. 9, the system 1360 of FIG. 13, and/or the sensor data analytics system 1402 of FIG. 14 to perform various methods and algorithms described above. Further, the processing circuitry and stored instructions may enable the peripheral device(s) 1354, 1390 of FIG. 13 to perform various methods and algorithms described above.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi, Bluetooth, Zigbee, or another wireless form of communication.

The computing device, such as the peripheral device(s) 1354, 1390 of FIG. 13, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

A sound controller, in some embodiments, is also provided in the computing device, such as the peripheral device(s) 1354, 1390 of FIG. 13, to interface with speakers/microphone thereby providing audio input and output.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Certain functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein.

The systems described herein may communicate with the cloud computing environment through a secure gateway. In some implementations, the secure gateway includes a database querying interface, such as the Google BigQuery platform.

In some implementations, an edge server is used to transfer data between one or more computing devices and a cloud computing environment according to various embodiments described herein. The edge server, for example, may be a computing device configured to execute processor intensive operations that are sometimes involved when executing machine learning processes, such as natural language processing operations. An edge server may include, for example, one or more GPUs that are capable of efficiently executing matrix operations as well as substantial cache or other high-speed memory to service the GPUs. An edge server may be a standalone physical device. An edge server may be incorporated into other computing equipment, such as a laptop computer, tablet computer, medical device, or other specialized computing device. Alternatively or additionally, an edge server may be located within a carrying case for such computing equipment. An edge server, in a further example, may be incorporated into the communications and processing capabilities of a mobile unit such as a vehicle or drone, or may otherwise be located within the mobile unit.

In some implementations, the edge server communicates with one or more local devices to the edge server. The edge server, for example, can be used to move a portion of the computing capability traditionally shifted to a cloud computing environment into the local environment so that any computation intensive data processing and/or analytics required by the one or more local devices can run accurately and efficiently. In some embodiments, the edge server is used to support the one or more local devices in the absence of a connection with a remote computing environment. The edge server may be configured to communicate with the one or more local devices directly or via a network. For instance, the edge server can include a private wireless network interface, a public wireless network interface, and/or a wired interface through which the edge server can communicate with the one or more local devices. In some embodiments, certain local devices may be configured to communicate indirectly with the edge server, for example via another local device. Further, the edge server may be configured to communicate with a remote computing (e.g., cloud) environment via one or more public or private wireless network interfaces. The device interoperating with the edge server, for example, may share processing functionality with the edge server via one or more APIs implemented by the processes.

The systems described herein may include one or more artificial intelligence (AI) neural networks for performing automated analysis of data. The AI neural networks, in some examples, can include a synaptic neural network, a deep neural network, a transformer neural network, and/or a generative adversarial network (GAN). The AI neural networks may be trained using one or more machine learning techniques and/or classifiers such as, in some examples, anomaly detection, clustering, and/or supervised and/or association. In one example, the AI neural networks may be developed and/or based on a bidirectional encoder representations for transformers (BERT) model by Google of Mountain View, CA.

The systems described herein may communicate with one or more foundational model systems (e.g., artificial intelligence neural networks). The foundational model system(s), in some examples, may be developed, trained, tuned, fine-tuned, and/or prompt engineered to evaluate data inputs such as sensor inputs collected by the system 1060 and/or the sensor data analytics system 1352 of FIG. 13 and/or sensor inputs collected by the sensor data analytics system 1402 of FIG. 14. The foundational model systems, in some examples, may include or be based off of the generative pre-trained transformer (GPT) models available via the OpenAI platform by OpenAI of San Francisco, CA (e.g., GPT-3, GPT-3.5, and/or GPT-4) and/or the generative AI models available through Azure OpenAI or Vertex AI by Google of Mountain View, CA (e.g., PaLM 2).

Certain foundational models may be fine-tuned as AI models trained for performing particular tasks required by the systems described herein. Training material, for example, may be submitted to certain foundational models to adjust the training of the foundational model for performing types of analyses described herein.

Multiple foundational model systems may be applied by the systems and methods described herein depending on context. The context, for example, may include type(s) of data, type(s) of response output desired (e.g., at least one answer, at least one answer plus an explanation regarding the reasoning that lead to the answer(s), etc.). In another example, the context can include user-based context such as demographic information, entity information, and/or product information. In some embodiments, a single foundational model system may be dynamically adapted to different forms of analyses requested by the systems and methods described herein using prompt engineering.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions, and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for increasing coagulation potential in a subject, the method comprising:
positioning at least one electrode at a location on or through skin of the subject such that each electrode of the at least one electrode is provided in electrical communication with nerve structures i) of or leading to an auriculotemporal nerve or ii) of or leading to an auricular branch of a vagus nerve; and
delivering an electrical neurostimulation therapy by
for each respective electrode of the at least one electrode in electrical communication with nerve structures of or leading to the auriculotemporal nerve, applying a first stimulation pattern within a frequency range from 70 to 150 Hertz, via the respective electrode, and/or
for each electrode of the at least one electrode in electrical communication with nerve structures of or leading to the auricular branch of the vagus nerve, applying a second stimulation pattern within a frequency range from 5 to 30 Hertz, via the respective electrode;
wherein the electrical neurostimulation therapy is configured to stimulate neural pathways leading to enervation of a spleen of the subject, thereby the coagulation potential in the subject.

2. The method of claim 1, wherein the electrical neurostimulation therapy is delivered repeatedly, on a periodic basis, to treat a chronic condition.

3. The method of claim 2, wherein the chronic condition is a chronic coagulation deficiency in the subject.

4. The method of claim 3, wherein the chronic coagulation deficiency is one of hemophilia A, hemophilia B, hemophilia C, or von Willebrand Disease.

5. The method of claim 1, wherein the electrical neurostimulation therapy is delivered prior to and/or during a surgical procedure to at least partially overcome an effect of an anticoagulant medication in a system of the subject.

6. The method of claim 1, the electrical neurostimulation therapy is delivered prior to and/or during a medical procedure having a substantial likelihood of causing bleeding.

7. The method of claim 6, wherein the electrical neurostimulation therapy is delivered to reduce a likelihood of blood transfusion and/or to reduce a volume required for the blood transfusion.

8. The method of claim 6, wherein the electrical neurostimulation therapy is delivered to reduce a volume of blood loss in circumstance of postpartum hemorrhage.

9. The method of claim 1, wherein the electrical neurostimulation therapy is configured to create a transient increase in the coagulation potential of the subject.

10. The method of claim 1, wherein the electrical neurostimulation therapy is delivered to treat abnormal uterine bleeding (AUB), heavy menstrual bleeding (HMB), and/or menorrhagia.

11. The method of claim 10, wherein the AUB, HMB, and/or menorrhagia results from a bleeding disorder.

12. The method of claim 1, wherein the electrical neurostimulation therapy is delivered as a preventative treatment or a prophylactic treatment.

13. The method of claim 12, wherein the electrical neurostimulation therapy is configured as the prophylactic treatment to minimize bleeding in individuals with a bleeding disorder.

14. The method of claim 13, wherein the bleeding disorder is one of hemophilia A, hemophilia B, hemophilia C, or von Willebrand Disease.

15. The method of claim 1, wherein the electrical neurostimulation therapy is delivered prior to and/or during a military operation.

16. The method of claim 1, wherein the electrical neurostimulation therapy increases a rate of thrombin production at or near an injury site of the subject.

17. A system for increasing coagulation potential of a subject, the system comprising:
an auricular stimulation device comprising
at least one therapeutic electrode, each respective therapeutic electrode of the at least one therapeutic electrode configured to be aligned with a region of skin of the subject for placing the respective therapeutic electrode in electrical communication with nerve structures i) of or leading to an auriculotemporal nerve, and/or ii) of or leading to an auricular branch of a vagus nerve; and
pulse generating circuitry configured to deliver an electrical neurostimulation therapy via the at least one therapeutic electrode by
for each respective electrode of the at least one therapeutic electrode in electrical communication with nerve structures of or leading to the auriculotemporal nerve, generating a first stimulation pattern within a frequency range from 70 to 150 Hertz for stimulating the auriculotemporal nerve via the respective electrode, and/or
for each respective electrode of the at least one therapeutic electrode in electrical communication with nerve structures of or leading to the auricular branch of the vagus nerve, generating a second stimulation pattern within a frequency range from 5 to 30 Hertz for stimulating the auricular branch of the vagus nerve via the respective electrode;
wherein the electrical neurostimulation therapy is configured to stimulate neural pathways leading to enervation of a spleen of the subject, thereby increasing the coagulation potential of the subject.

18. The system of claim 17, wherein the electrical neurostimulation therapy is applied prior to and/or during a surgical procedure.

19. The system of claim 18, wherein the electrical neurostimulation therapy is applied to reduce a likelihood of blood transfusion and/or to reduce a volume required for the blood transfusion.

20. The system of claim 17, wherein the electrical neurostimulation therapy is configured to create a transient increase in the coagulation potential of the subject.

21. The system of claim 17, wherein the electrical neurostimulation therapy is further configured to increase a rate of thrombin production at or near an injury site of the subject.

22. The system of claim 21, wherein the injury site comprises at least one of a penetrating injury or a non-compressible injury.

23. The system of claim 22, wherein the non-compressible injury is gastrointestinal bleeding.

\* \* \* \* \*